US012275002B2

United States Patent
Ghoniem et al.

(10) Patent No.: US 12,275,002 B2
(45) Date of Patent: Apr. 15, 2025

(54) METHANE UPGRADE TO ETHANE AND ETHYLENE WITHIN CERAMIC MEMBRANE REACTORS

(71) Applicant: MASSACHUSETTS INSTITUTE OF TECHNOLOGY, Cambridge, MA (US)

(72) Inventors: Ahmed Ghoniem, Winchester, MA (US); Bilge Yildiz, Cambridge, MA (US); Georgios Dimitrakopoulos, Boston, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 17/243,219

(22) Filed: Apr. 28, 2021

(65) Prior Publication Data

US 2022/0370988 A1 Nov. 24, 2022

(51) Int. Cl.
| | | |
|---|---|---|
| *B01J 37/03* | (2006.01) | |
| *B01J 23/10* | (2006.01) | |
| *B01J 23/78* | (2006.01) | |
| *B01J 35/59* | (2024.01) | |
| *B01J 35/70* | (2024.01) | |
| *B01J 37/08* | (2006.01) | |
| *C01G 49/00* | (2006.01) | |
| *C07C 2/84* | (2006.01) | |

(52) U.S. Cl.
CPC ............... *B01J 23/78* (2013.01); *B01J 23/10* (2013.01); *B01J 35/59* (2024.01); *B01J 37/031* (2013.01); *C01G 49/009* (2013.01); *C07C 2/84* (2013.01); *C07C 2523/10* (2013.01); *C07C 2523/78* (2013.01)

(58) Field of Classification Search
CPC . B01J 23/10; B01J 23/78; B01J 35/065; B01J 37/031; C01G 49/009; C07C 2/84; C07C 2523/10; C07C 2523/78
See application file for complete search history.

(56) References Cited

U.S. PATENT DOCUMENTS 9,610,565 B2    4/2017   Ghose et al.

OTHER PUBLICATIONS

Schucker et al. ("Oxidative Dehydrogenation of Ethane to Ethylene in an Oxygen-Ion-Transport-Membrane Reactor: A Proposed Design for Process Intensification." Ind. Eng. Chem. Res. 2019, 58, 7989-7997) (Year: 2109).*
He et al. ("Zr doped BaFeO3-σ as a robust electrode for symmetrical solid oxide fuel cell." International Journal of Hydrogen Energy 44.60 (2019): 32164-32169 (Year: 2019).*
Czuprat et al., "Oxidative Coupling of Methane in a BCFZ Perovskite Hollow Fiber Membrane Reactor," Industrial & Engineering Chemistry Research, vol. 49, No. 21, pp. 10230-10236, Apr. 2010.

(Continued)

*Primary Examiner* — Jonathan Miller
*Assistant Examiner* — Jason Y Chong
(74) *Attorney, Agent, or Firm* — Nields, Lemack & Frame, LLC

(57) ABSTRACT

A ceramic membrane for oxidative coupling of methane can include a perovskite oxide and catalyst material on a surface of the membrane.

12 Claims, 34 Drawing Sheets

(56) References Cited

OTHER PUBLICATIONS

Dimitrakopoulos et al., "Hydrogen and Ethylene Production through Water-Splitting and Ethane Dehydrogenation Using BaFe0.9Zr0.103-o Mixed-Conductors," ECS Transactions, vol. 80, No. 9, pp. 181-190, Aug. 2017.

Lu et al., "Oxidative Coupling of Methane over SrO/La2O3 Catalyst in an Oxygen-Permeable Separation Membrane Reactor," Catalysis Letters, vol. 151, No. 6, pp. 1805-1809, Nov. 2020.

U.S. Department of Energy, "Ethylene via Low Temperature Oxidative Coupling of Methane," Advanced Manufacturing Office, two pages, Aug. 2016.

Zhang et al., "Methane Oxidative Coupling to C2 Hydrocarbons over Lanthanum promoted Barium Catalysts," Applied Catalysis, vol. 62, Iss. 1, pp. L29-L33, Jun. 1990.

\* cited by examiner

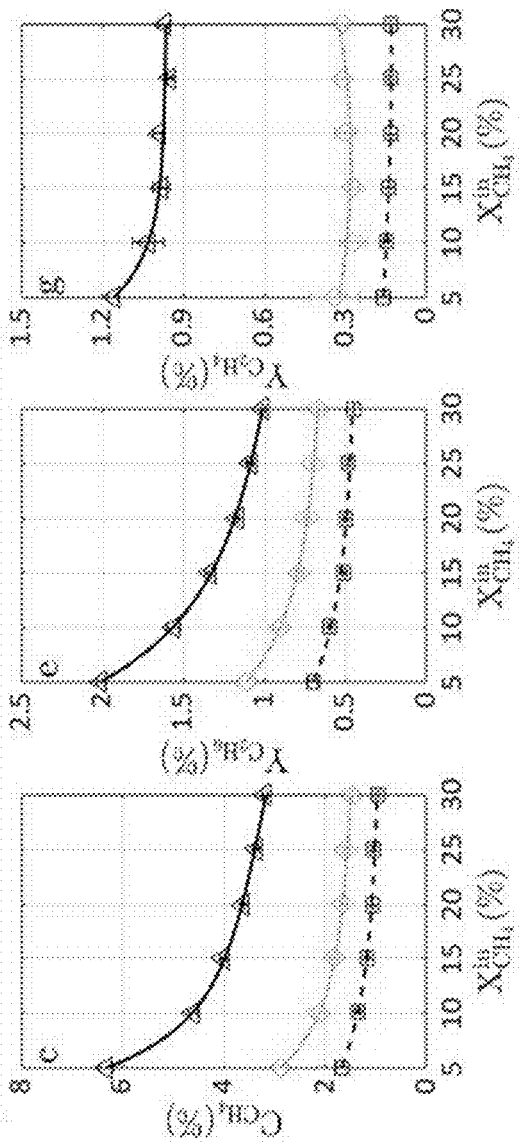
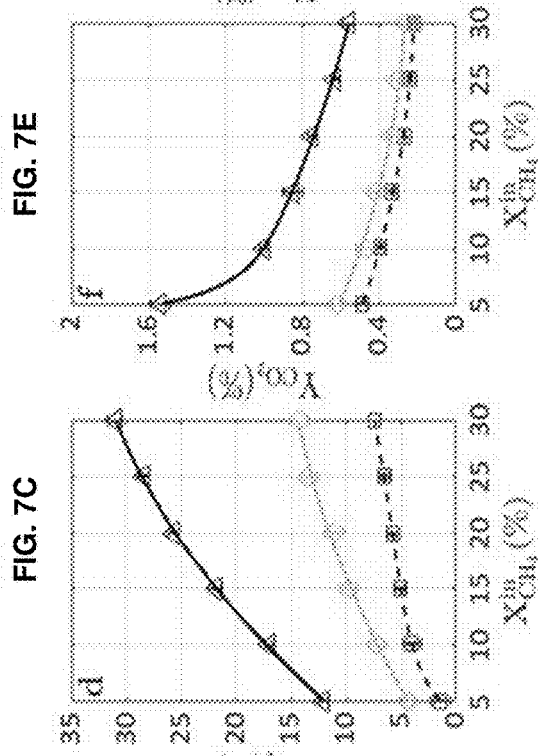
FIG. 7A  FIG. 7B  FIG. 7C  FIG. 7D
FIG. 7E  FIG. 7F  FIG. 7G  FIG. 7H

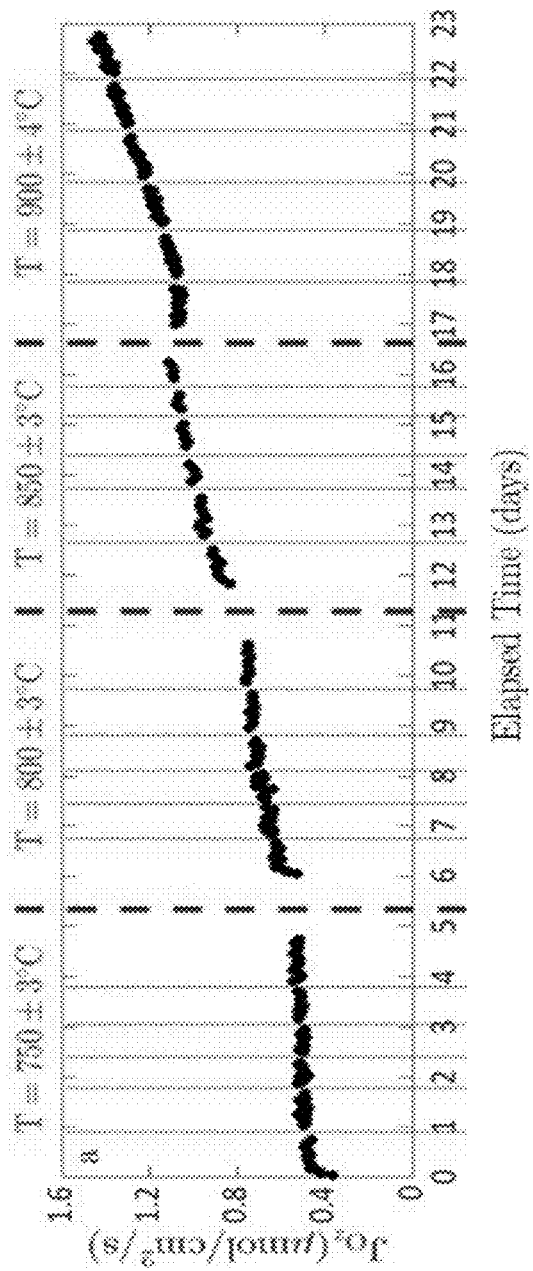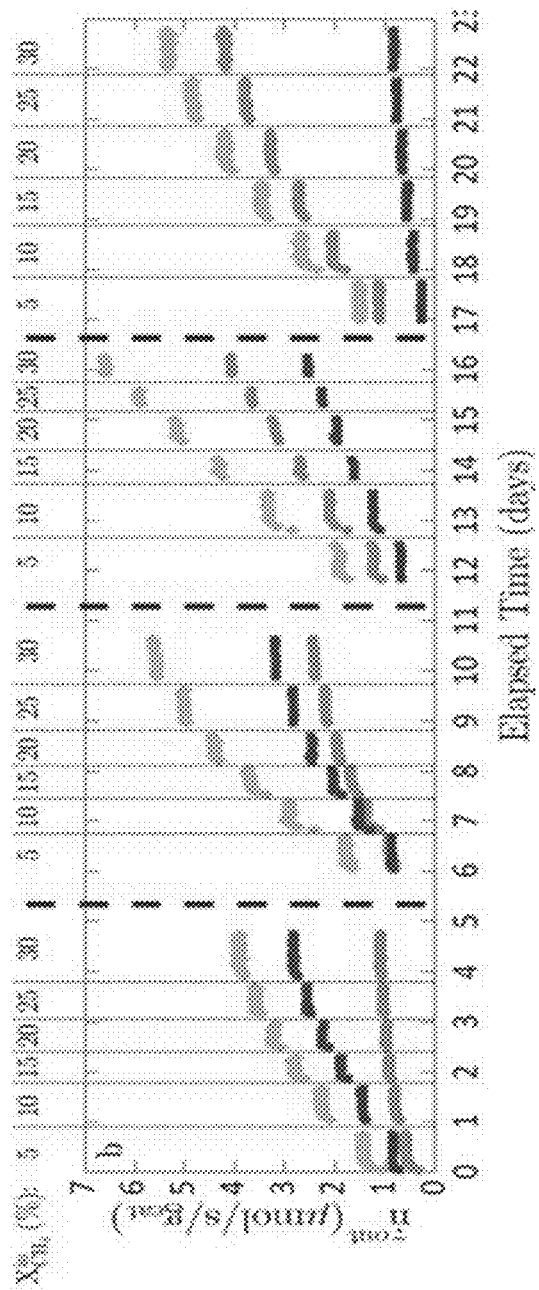
FIG. 8A
FIG. 8B

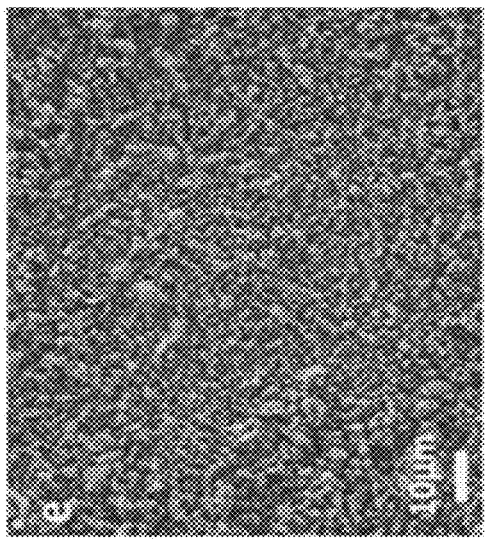
FIG. 10A
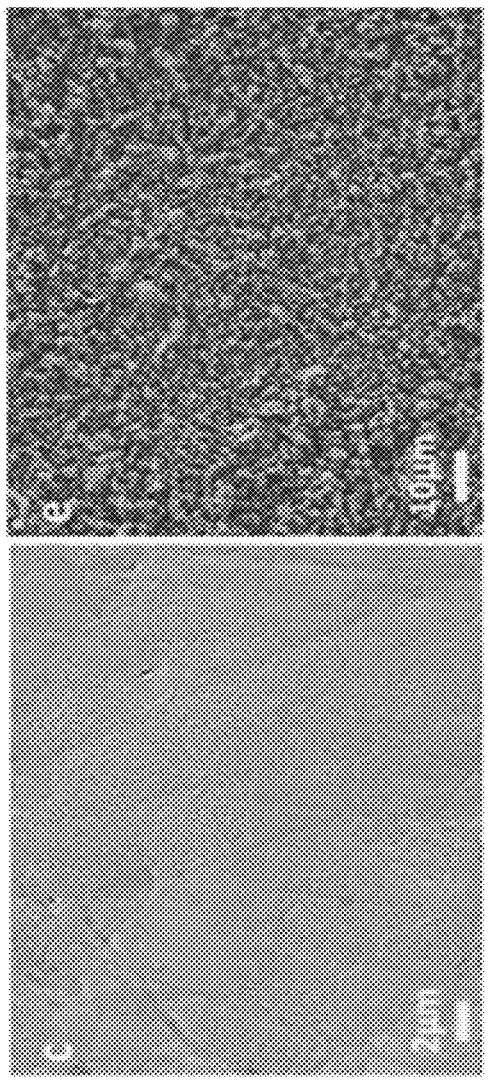
FIG. 10C
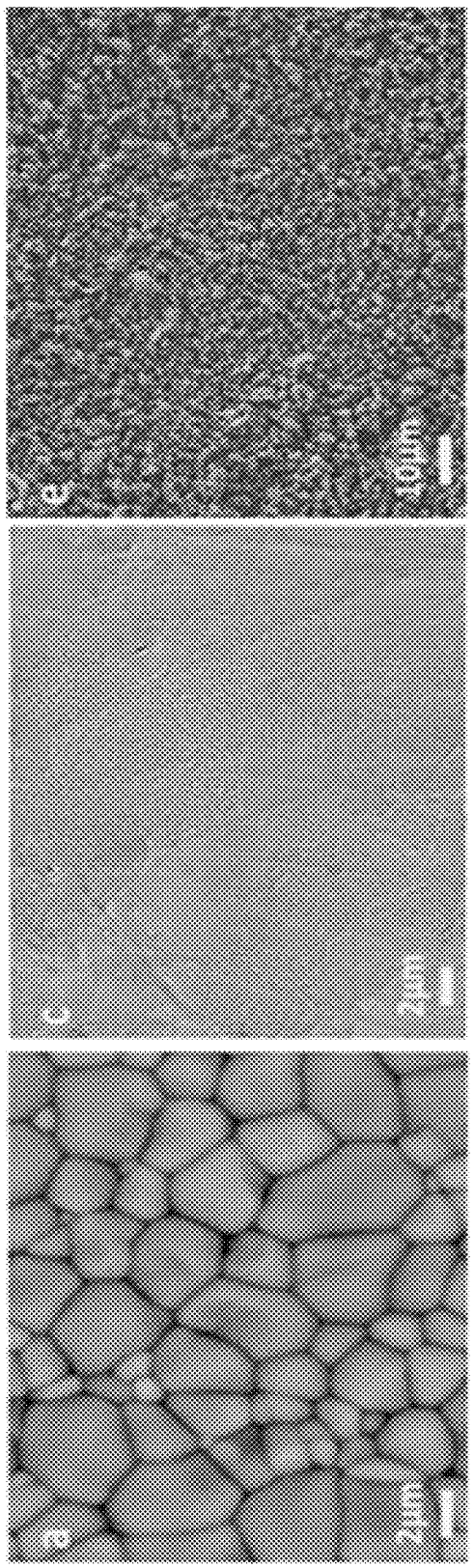
FIG. 10E
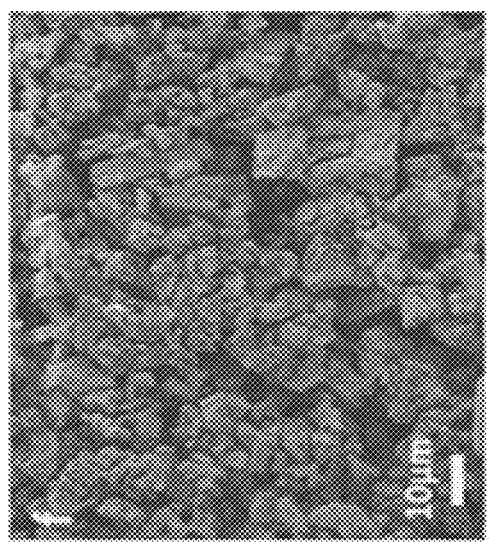
FIG. 10B
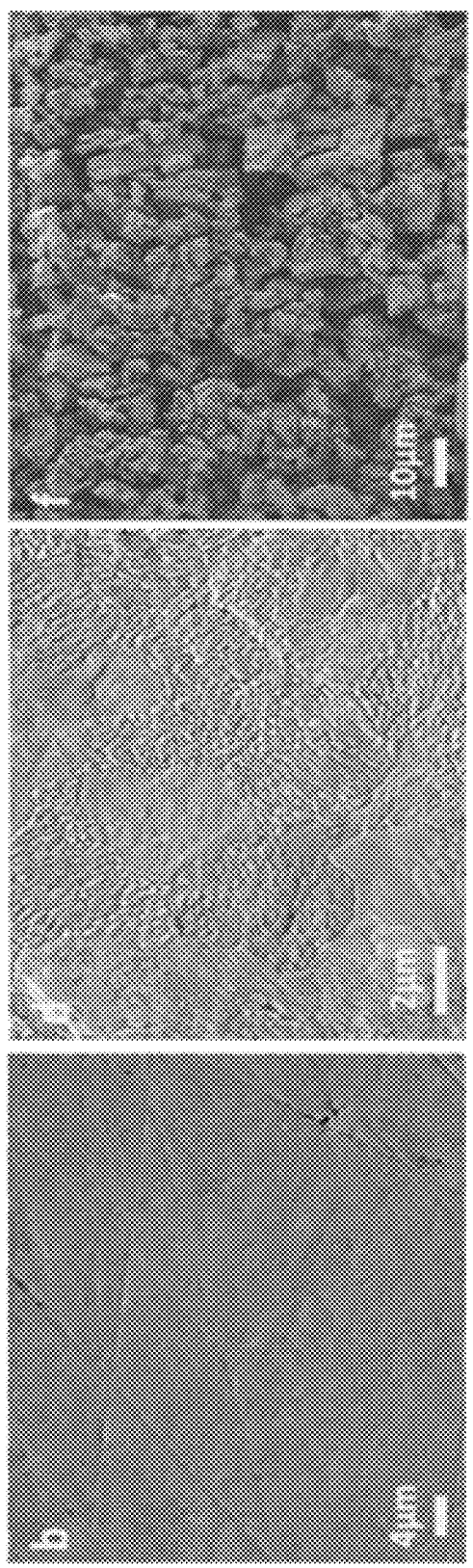
FIG. 10D
FIG. 10F

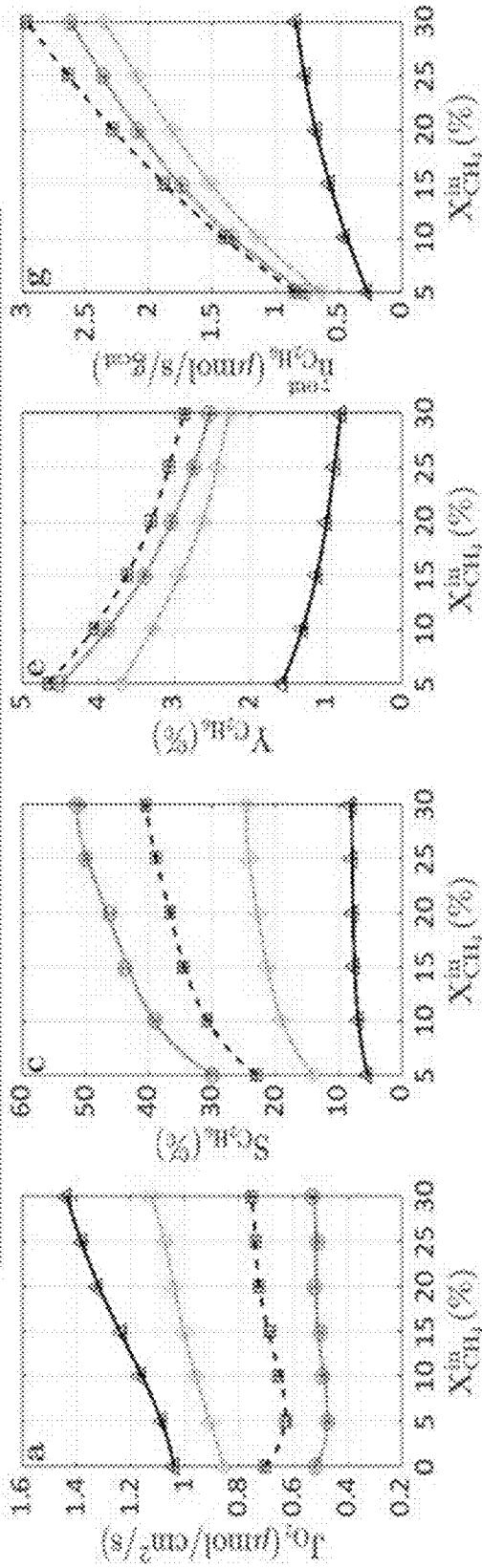
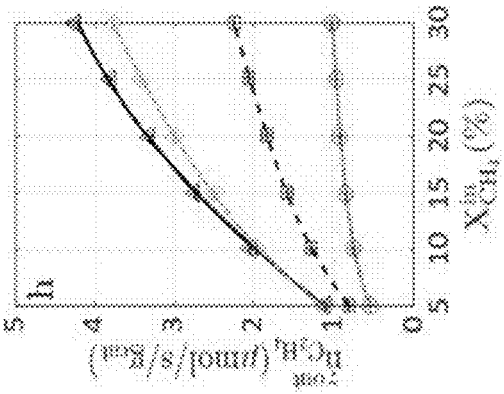
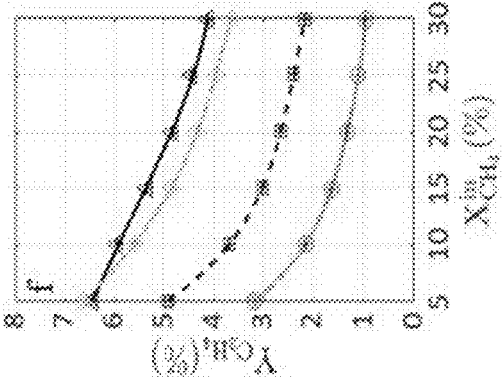
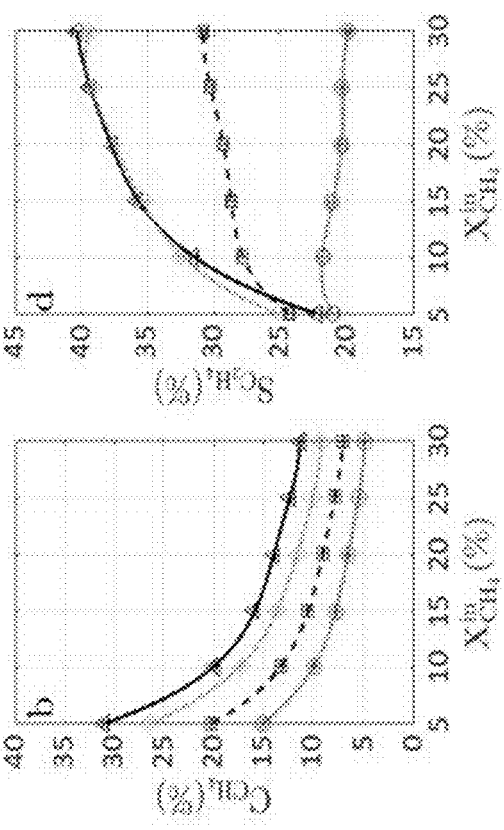
FIG. 11A FIG. 11B FIG. 11C FIG. 11D FIG. 11E FIG. 11F FIG. 11G FIG. 11H

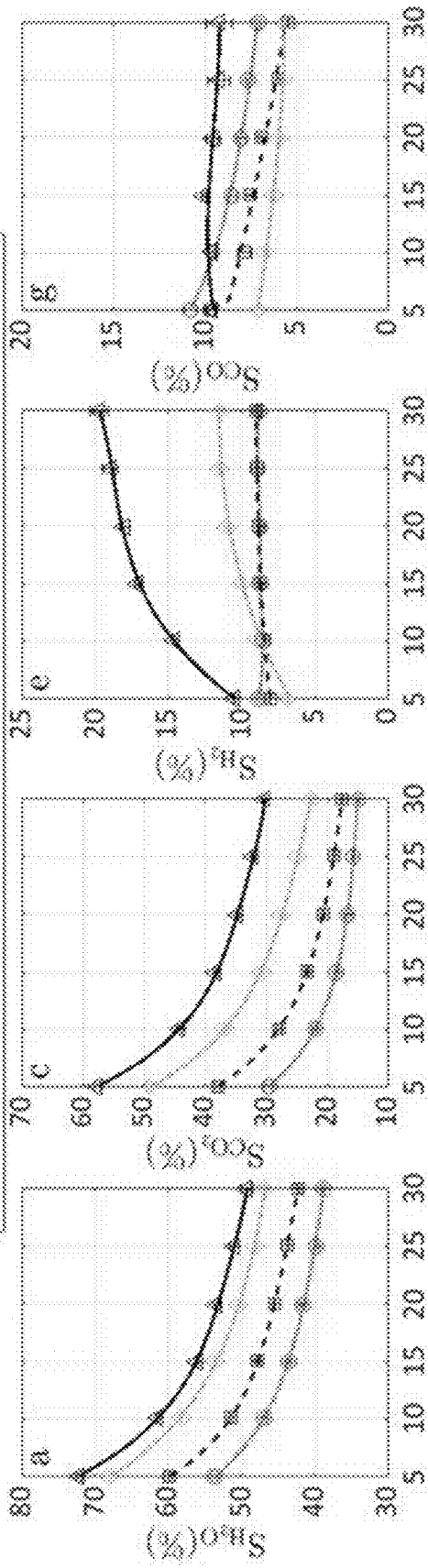
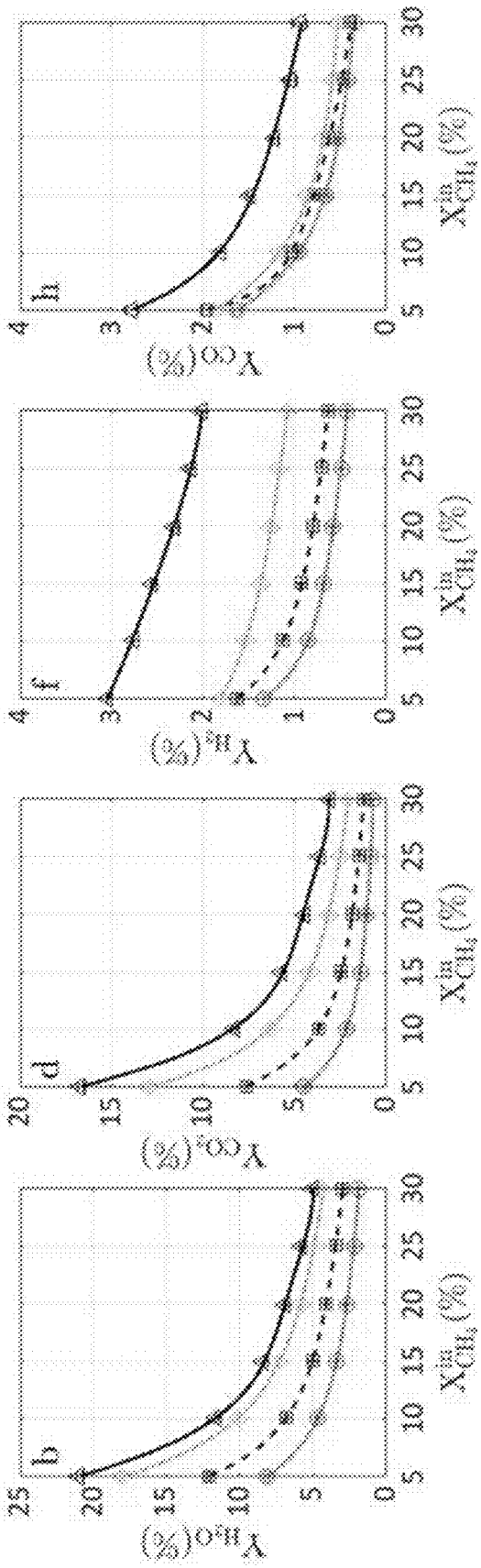

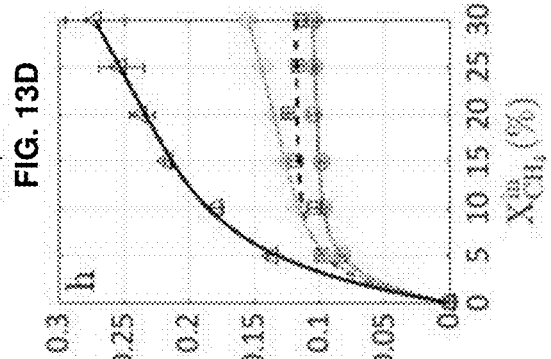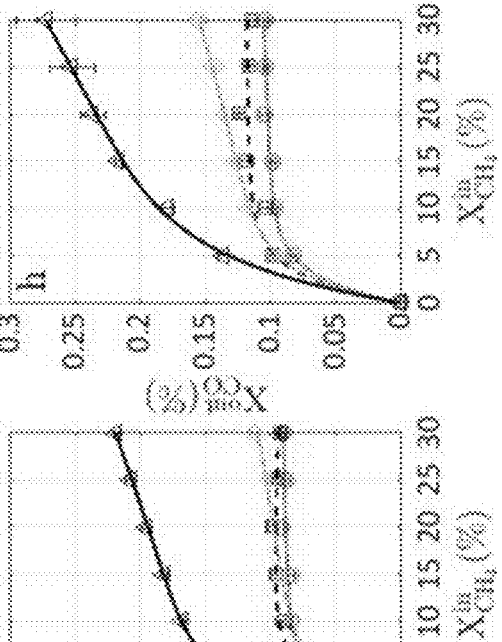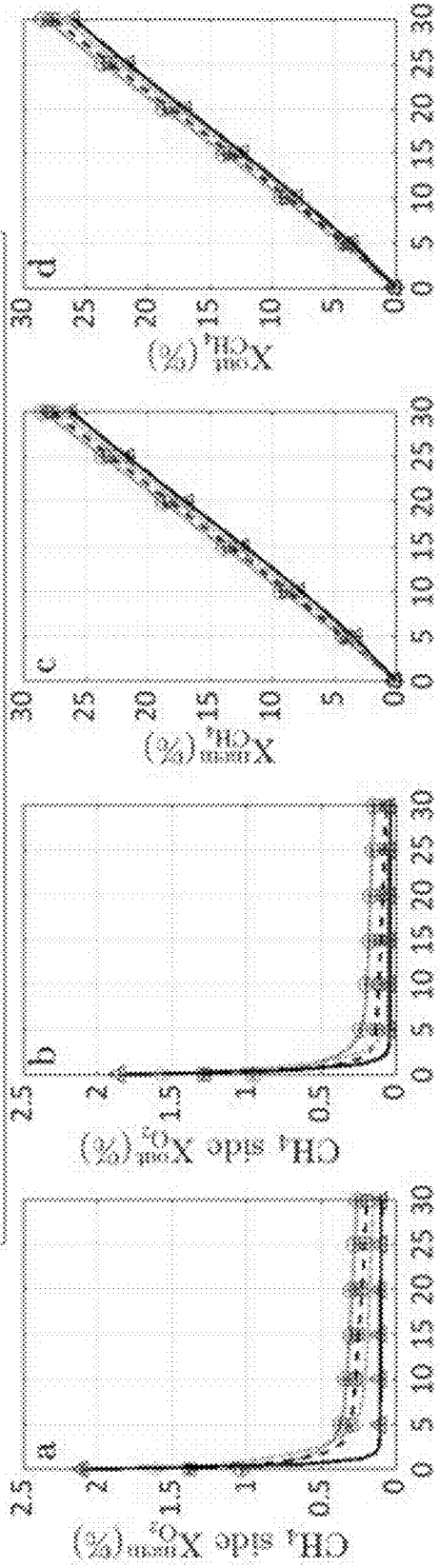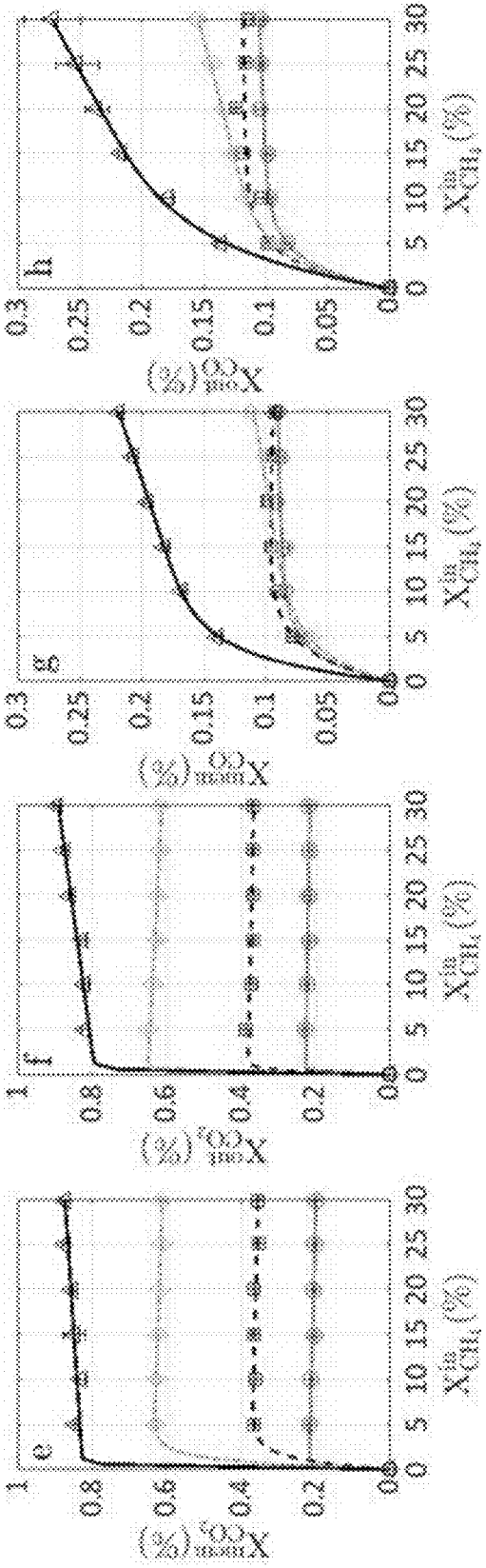
FIG. 13A  FIG. 13B  FIG. 13C  FIG. 13D
FIG. 13E  FIG. 13F  FIG. 13G  FIG. 13H

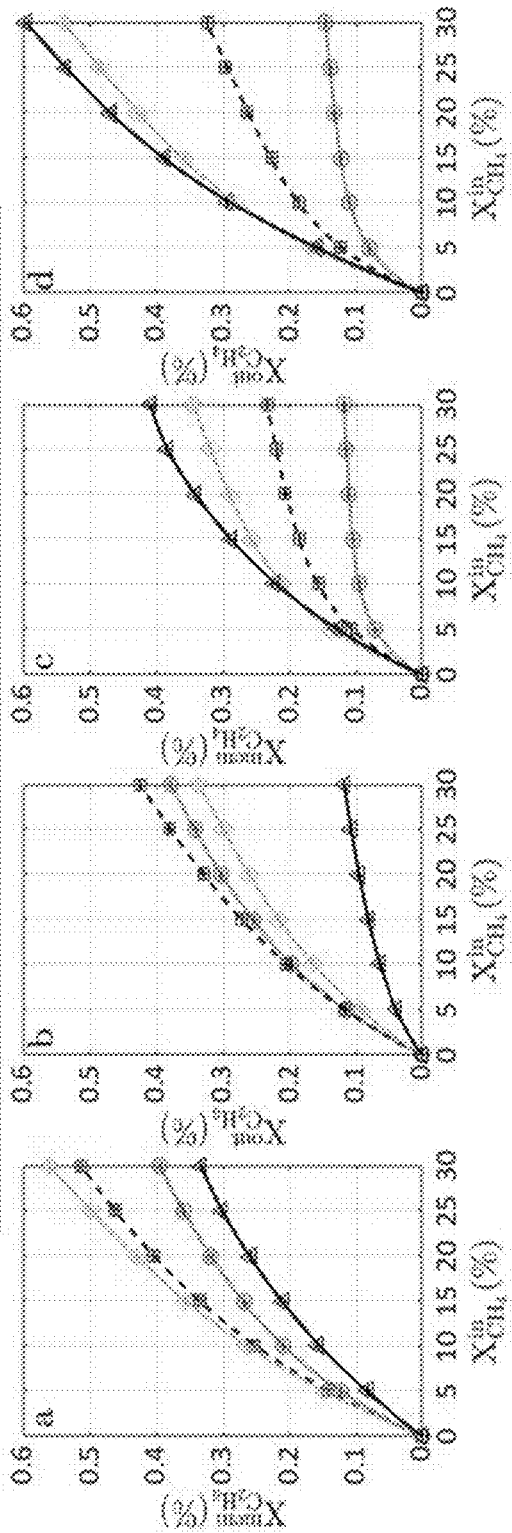
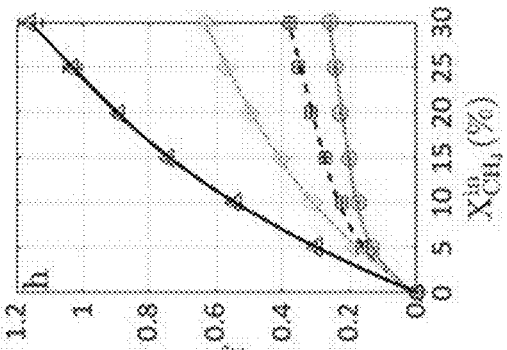
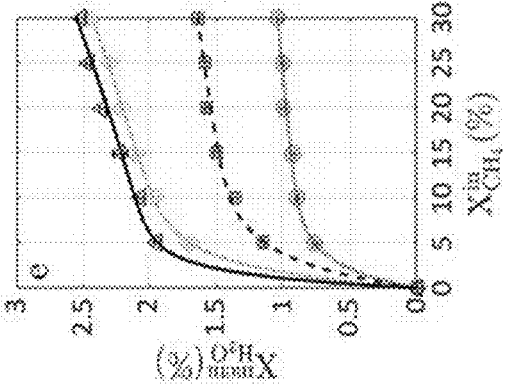
FIG. 14A FIG. 14B FIG. 14C FIG. 14D
FIG. 14E FIG. 14F FIG. 14G FIG. 14H

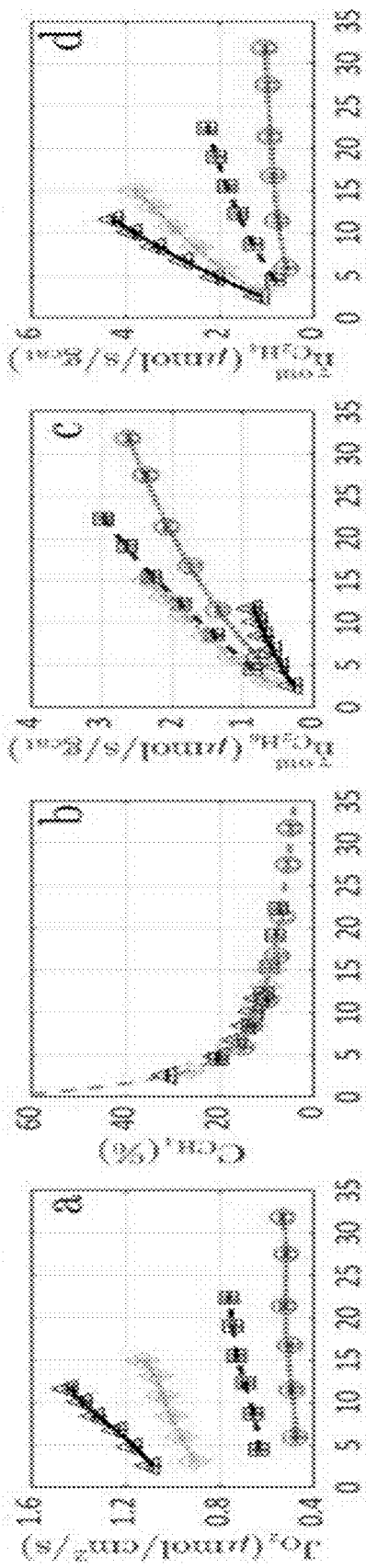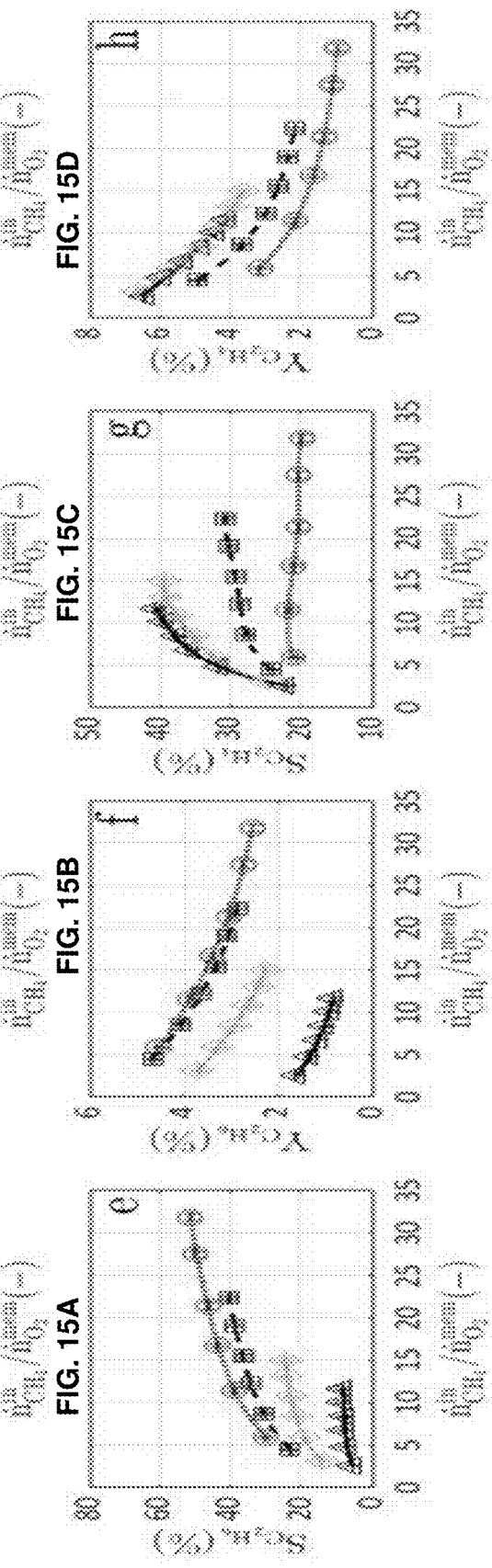
FIG. 15A  FIG. 15B  FIG. 15C  FIG. 15D
FIG. 15E  FIG. 15F  FIG. 15G  FIG. 15H

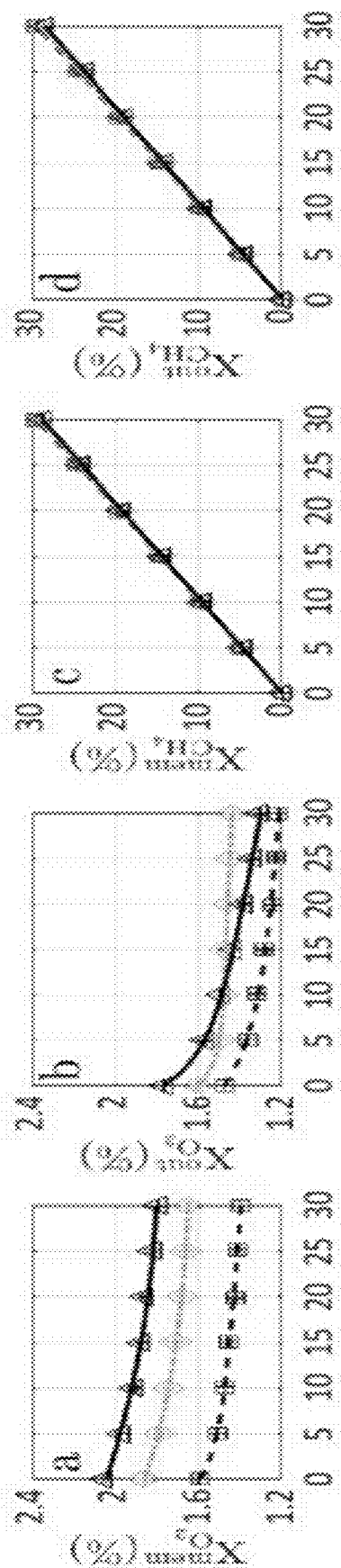
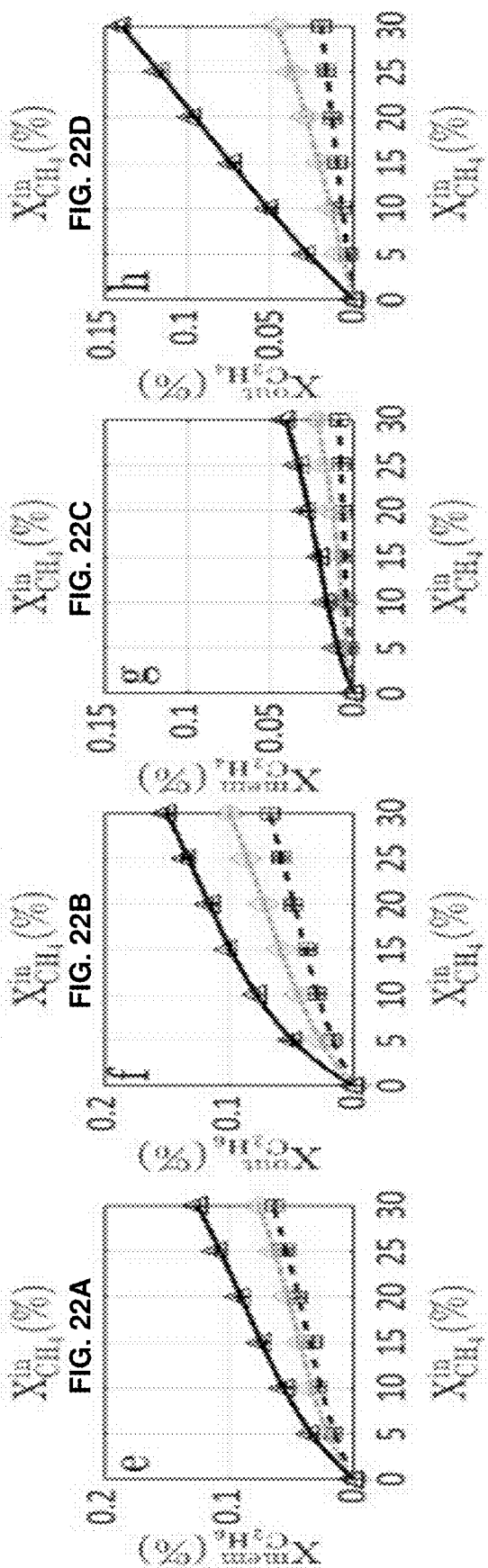
FIG. 22A  FIG. 22B  FIG. 22C  FIG. 22D
FIG. 22E  FIG. 22F  FIG. 22G  FIG. 22H

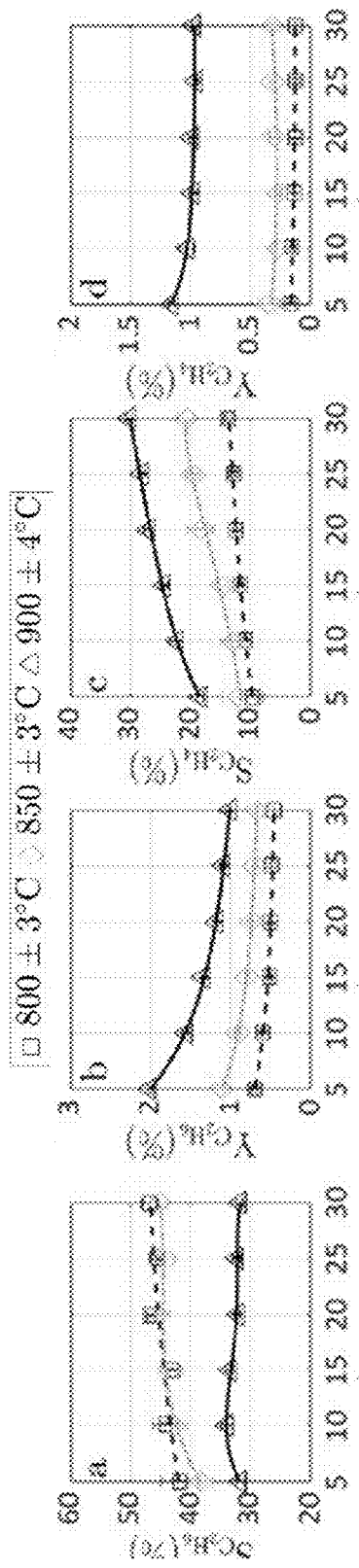
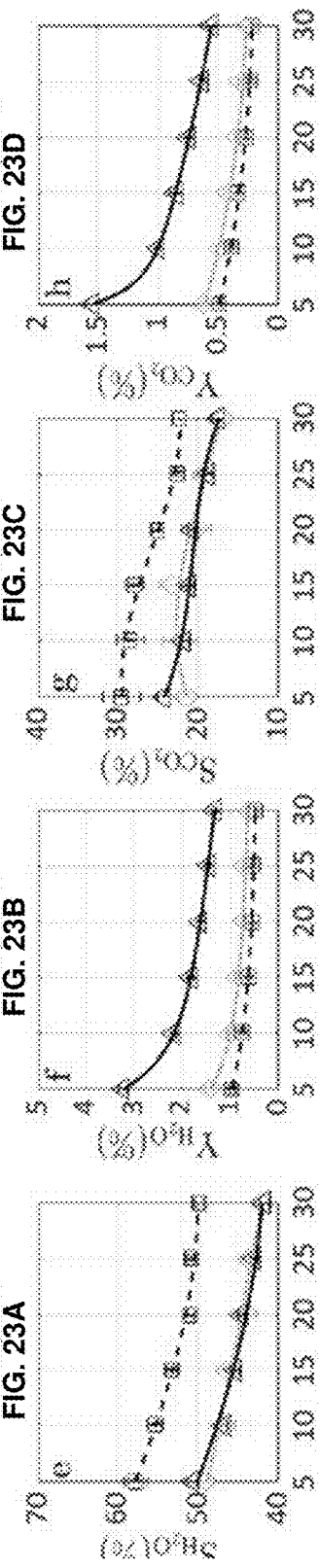
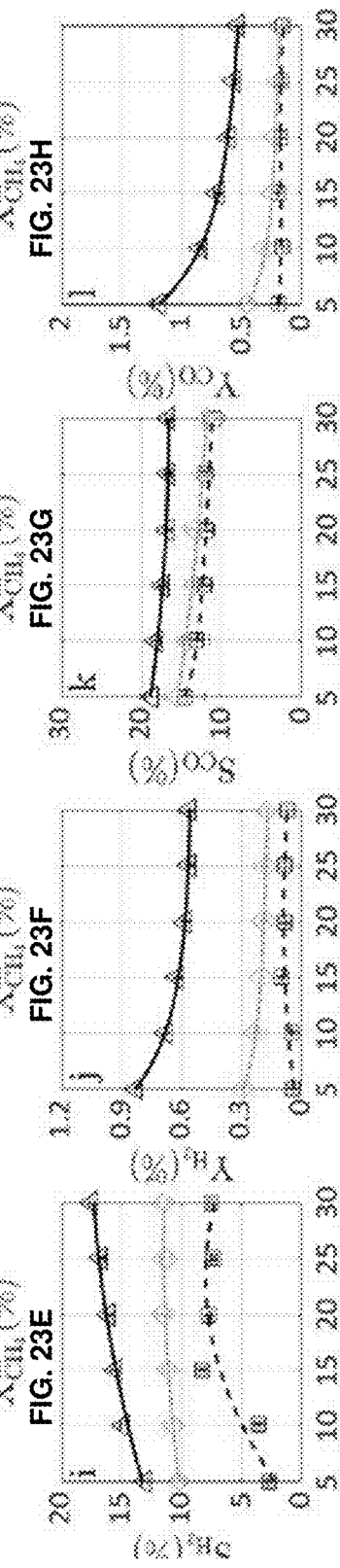
FIG. 23A  FIG. 23B  FIG. 23C  FIG. 23D
FIG. 23E  FIG. 23F  FIG. 23G  FIG. 23H
FIG. 23I  FIG. 23J  FIG. 23K  FIG. 23L

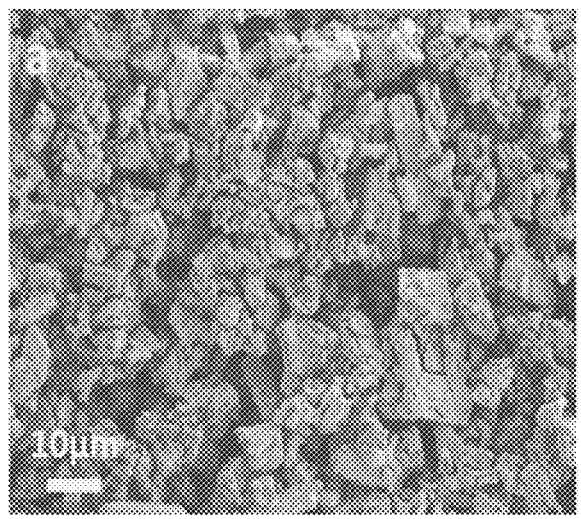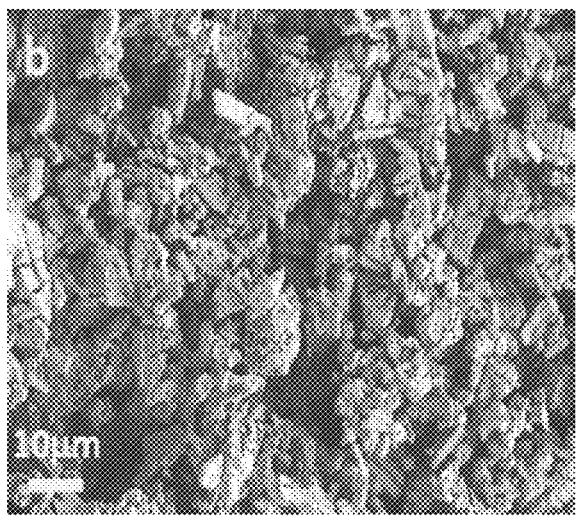
After OCM measurements
Calcined in ambient air (T=1025°C, 24h)
FIG. 25A  FIG. 25B
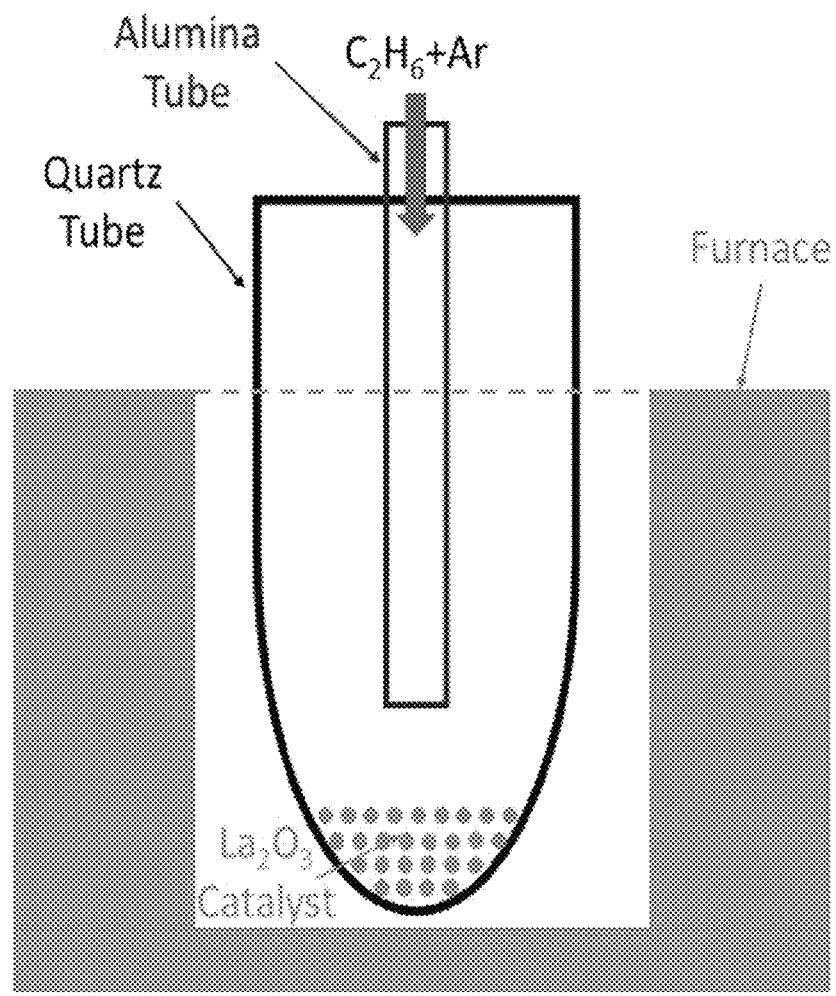
FIG. 26

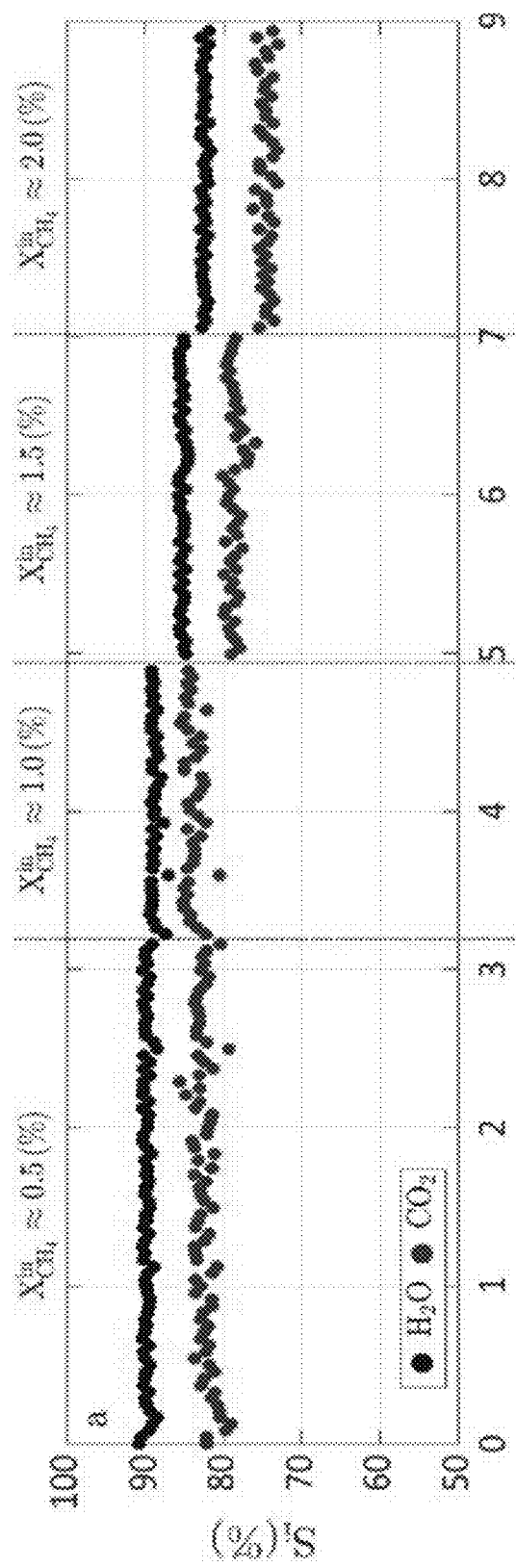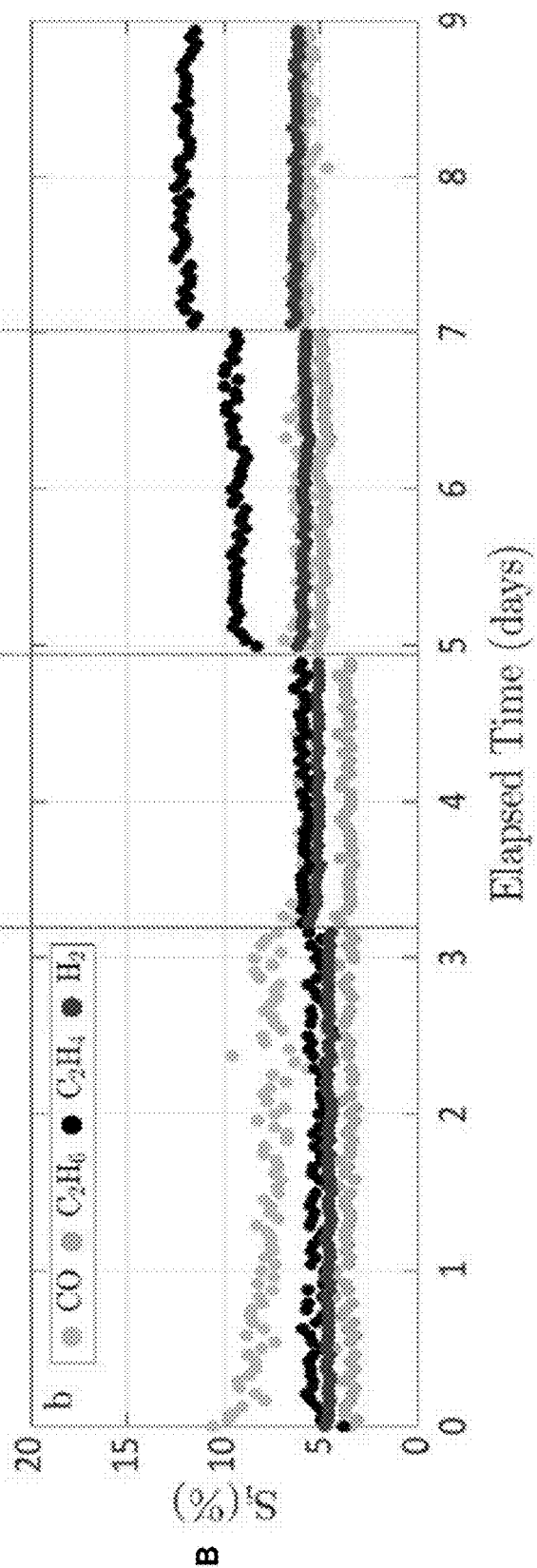
FIG. 28A
FIG. 28B

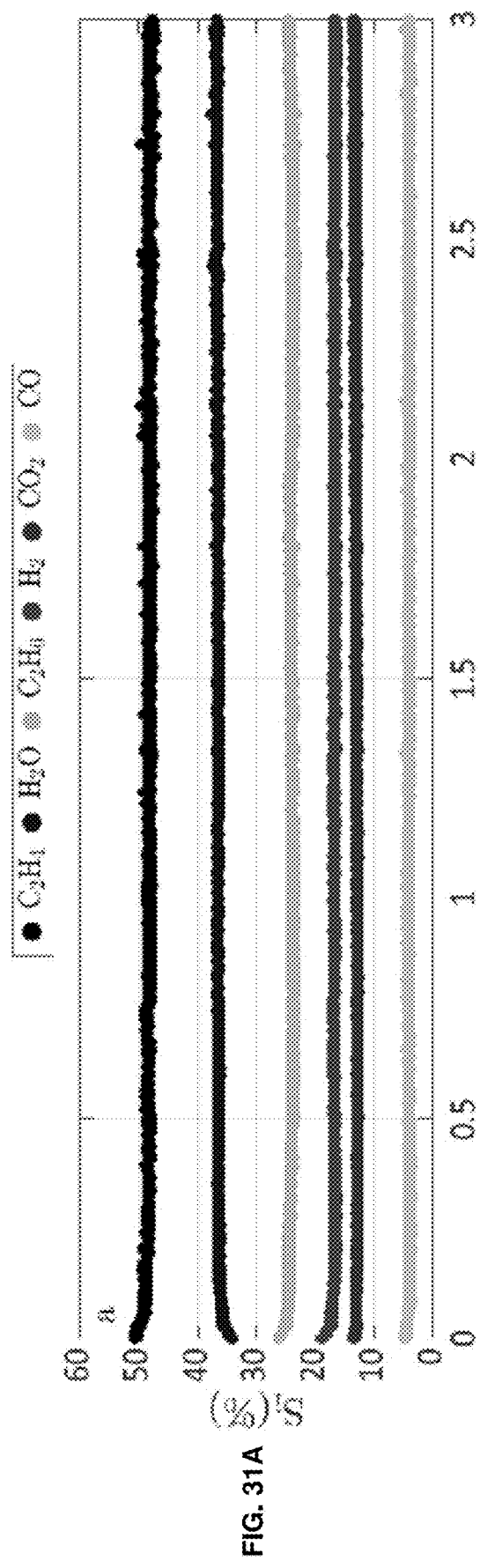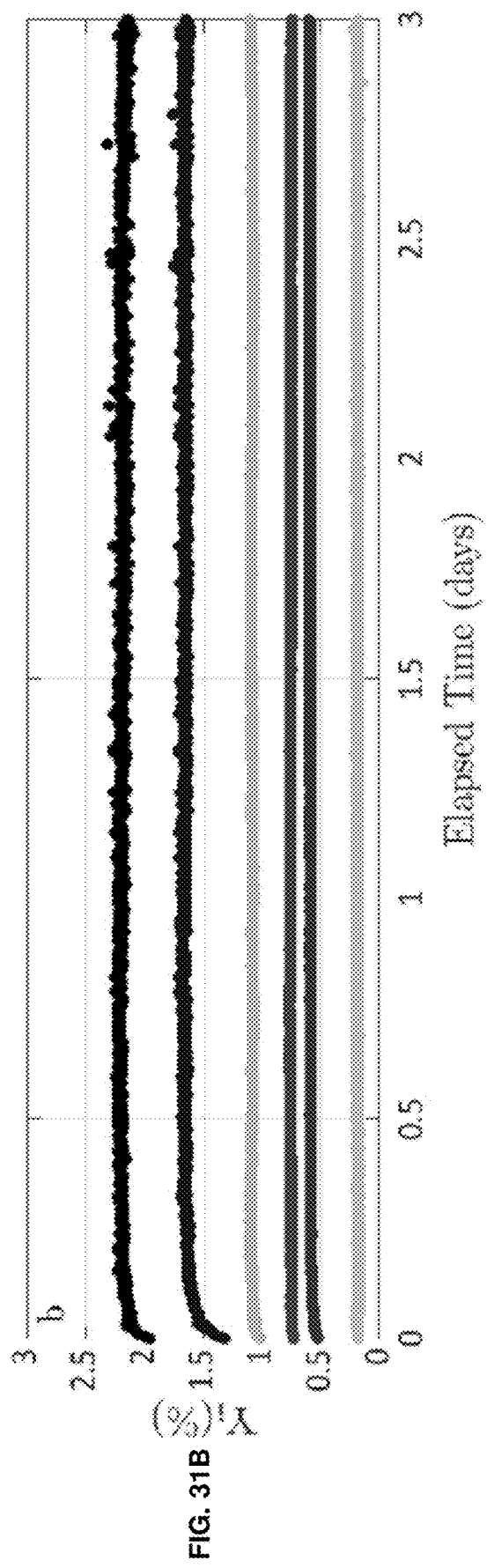
FIG. 31A
FIG. 31B

METHANE UPGRADE TO ETHANE AND ETHYLENE WITHIN CERAMIC MEMBRANE REACTORS

TECHNICAL FIELD

This invention relates to catalytic ceramic membranes based on mixed ionic and electronic conducting materials and their use in the oxidative coupling of methane to produce ethane and ethylene.

BACKGROUND

Perovskite oxides are important enablers of a number of technological applications, including oxygen ion and proton conducting membranes; in chemical looping as oxygen carriers; in solid oxide fuel or electrolysis cells as electrodes and as catalysts for several oxidation and reduction reactions.

$C_2H_4$ is one of the most important commodity chemicals worldwide with a 2018 global production of ~185 million metric tons (MMT). (See ref. 1) During 2019, the production of $C_2H_4$ in the United States (US) was the highest among other chemicals and plastics reaching ~32 MMT. (See ref. 2) Its high demand is related primarily to its use as a building block in the production of polymers, such as polyethylene and polyvinyl chloride. (See ref. 3) Other uses of $C_2H_4$ include the synthesis of intermediate chemical compounds and its utilization as a plant hormone in agriculture. (See ref. 3) Given its high demand, projections reveal that the global $C_2H_4$ production could rise to ~260 MMT by 2023 (see ref. 4) and in the long term to ~290 MMT by 2030. (See ref. 1) The price of $C_2H_4$ is relatively high and can exhibit significant fluctuations during a calendar year. For example, the $C_2H_4$ contract price in the US during 2019 ranged between $530-650 per metric ton driven by monthly changes in the $C_2H_4$ demand and production and by variations in the feedstock price. (See ref. 5)

SUMMARY

In one aspect, a ceramic membrane can include a perovskite oxide having the formula $BaBO_{3-\delta}$, wherein B is Fe or Zr, or mixtures thereof, and $\delta$ is 0 to 0.6. The perovskite oxide can be synthesized by wet chemical methods.

The ceramic membrane can include a catalytic metal distributed on a surface of the perovskite oxide of the membrane.

In another aspect, a reactor can include a housing having a first chamber and a second chamber, the first chamber and the second chamber separated by a membrane including the ceramic membrane described herein, the first chamber configured for a first gas flow and the second chamber configured for a second gas flow.

In another aspect, a method of manufacturing $C_2$ hydrocarbons can include contacting a first gas including oxygen with a first surface of a ceramic membrane described herein; and contacting a second gas including methane with oxygen passing through the ceramic membrane with a catalytic material, thereby generating a $C_2$ hydrocarbon. The catalytic material can be downstream of the ceramic membrane or in contact to the surface of the ceramic membrane. For example, when the catalytic material is downstream of the ceramic membrane, the catalytic material can be in the form of a powder creating a fixed-bed type configuration. When the catalytic material is in contact to the surface of the ceramic membrane, the catalytic material can be in the form of a porous electrode or a powder creating a fixed-bed type configuration. For example, a method of manufacturing $C_2$ hydrocarbons can include contacting a first gas including oxygen with a first surface of the ceramic membrane comprising a perovskite oxide having the formula $BaBO_{3-\delta}$, wherein B is Fe or Zr, or mixtures thereof, and $\delta$ is 0 to 0.6 and contacting a second gas including methane with oxygen passing through the ceramic membrane with a lanthanum oxide catalyst, opposite the first surface, thereby generating $C_2$ hydrocarbons. In certain circumstances, the $C_2$ hydrocarbon can include ethane or ethylene.

In another aspect, a method of making a perovskite oxide can include dissolving a barium salt, an iron salt, and a zirconium salt in a solvent to form a precursor solution, adjusting the pH of the precursor solution to form a mixture, drying the mixture to form an ash, and calcining the ash to form the perovskite oxide.

In certain circumstances, B can be a mixture of Fe and Zr. For example, the mixture of Fe and Zr can be between 1% and 20% Zr, preferably between 2% to 15% Zr.

In certain circumstances, the perovskite oxide can have a unit cell lattice constant of 4.022 Å or greater.

In certain circumstances, the perovskite oxide can be $BaFe_{0.9}Zr_{0.1}O_{3-\delta}$.

In certain circumstances, $\delta$ can be 0 to 0.6, preferably 0.1 to 0.55, or more preferably 0.15 to 0.5

In certain circumstances, the perovskite oxide can be $BaFe_{0.9}Zr_{0.1}O_{2.56}$.

In certain circumstances, the perovskite oxide can be made by a wet chemical process.

In certain circumstances, the membrane can include a lanthanum oxide catalyst on a surface of the perovskite oxide of the membrane.

In certain circumstances, the lanthanum oxide catalyst can be substantially free of other metals. For example, the lanthanum oxide catalyst can be substantially free of strontium or calcium. In another example, the lanthanum oxide catalyst can be substantially free of lanthanum hydroxides, lanthanum carbonates, or combinations thereof. In certain circumstances, the lanthanum oxide catalyst can be modified. For example, the lanthanum oxide catalyst can include alkaline earth metals, transition metals or lanthanides.

In certain circumstances, the $C_2$ hydrocarbons can include $C_2H_6$ and $C_2H_4$. In certain circumstances, $C_2H_4$ can be favored over $C_2H_6$ In certain circumstances, the $C_2$ hydrocarbons can include $C_2H_2$.

In certain circumstances, the method of manufacturing $C_2$ hydrocarbons can include heating a reactor including the ceramic membrane to a temperature between 650° C. and 1100° C., preferably between 700° C. and 900° C.

In certain circumstances, in the method of making a perovskite oxide, the precursor solution can include citric acid and a chelating agent. The chelating agent can be a multidendate ligand, such as ethylenediaminetetraacetic acid.

In certain circumstances, in the method of making a perovskite oxide, the ash can be calcined at 800° C. to 1000° C.

In certain circumstances, the method of making a perovskite oxide can include sintering the perovskite oxide at 1250° C. or less.

Other aspects, embodiments, and features will be apparent from the following description, the drawings, and the claims.

BRIEF DESCRIPTION OF THE DRAWINGS

FIGS. 3B and 3D are subplots that zoom into the 2θ range of 29-33° to highlight the peak shift between the two patterns.

FIG. 4A shows weight percentage during the heating step, FIG. 4B shows weight percentage during equilibration at 1000° C. for 3 h, FIG. 4C shows Δδ during the heating step, and FIG. 4D shows Δδ during equilibration at 1000° C. for 3 h.

FIGS. 5A-5B depict XRD patterns of: (FIG. 5A) as-received $La_2O_3$ powder and (FIG. 5B) as-received $La_2O_3$ powder after heat-treatment in ambient air at 800° C. for 2 h. Blue circles correspond to $La(OH)_3$ peaks (ICDD 04-016-2506). Note that a logarithmic y-axis is used to increase the visibility of the $La(OH)_3$ peaks.

FIGS. 7A-7H depict performance of BFZ91 as a function of T and $X^{in}_{CH4}$ in the absence of $La_2O_3$. (FIG. 7A) $J_{O2}$, (FIG. 7B) $CH_4$ side $X^{mem}_{O2}$, (FIG. 7C) $C_{CH4}$, (FIG. 7D) $C_{O2}$, (FIG. 7E) $Y_{C2H6}$, (FIG. 7F) $Y_{CO2}$, (FIG. 7G) $Y_{C2H4}$, and (FIG. 7H) $Y_{CO}$. Marker-line equivalence: (1) T=800±3° C.: squares-dashed line, (2) T=850±3° C.: diamond-dashed dotted line, and (3) T=900±4° C.: triangles-solid line. Lines are guides to the eye. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.67 mm.

FIGS. 8A-8B depict long-term OCM measurements of BFZ91 with $La_2O_3$ powder on the $C_4$ side. (FIG. 8A) $J_{O2}$ (black) as a function of time and (FIG. 8B) $\tilde{n}^{out}_{C2H4}$ (orange), $\tilde{n}^{out}_{C2H6}$ (pink) and $\tilde{n}^{out}_{C2}=\tilde{n}^{out}_{C2H6}+\tilde{n}^{out}_{C2H4}+\tilde{n}^{out}_{C2H2}$ (green) as a function of time. Red dashed lines correspond to increases in the reactor temperature while blue dotted lines correspond to instants of $X^{in}_{CH4}$ change. Measurements were conducted every 1 h. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.68 mm, while the thickness of the $La_2O_3$ catalyst layer was 1.5 mm.

FIGS. 9A-9B depict XRD patterns of: (FIG. 9A) as-prepared and used BFZ91 pellet and (FIG. 9B) as-received and used $La_2O_3$ catalyst. Patterns correspond to the long-term measurements reported in FIGS. 8A-8B.

FIGS. 10A-10F depict SEM images of BFZ91 and $La_2O_3$: (FIG. 10A) as-prepared BFZ91 pellet prior to polishing, (FIG. 10B) as-prepared BFZ91 pellet after polishing and prior to any measurements, (FIG. 10C) air side of the BFZ91 pellet after the end of the OCM measurements with $La_2O_3$, (FIG. 10D) $CH_4$ side of the BFZ91 pellet after the end of the OCM measurements with $La_2O_3$, (FIG. 10E) as-purchased $La_2O_3$ powder, and (FIG. 10F) $La_2O_3$ powder after the end of the OCM measurements.

FIGS. 11A-11H depict steady-state OCM measurements of BFZ91 with $La_2O_3$ as a function of T and $X^{in}_{CH4}$ in (FIG. 11A) $J_{O2}$, (FIG. 11B) $C_{CH4}$, (FIG. 11C) $S_{C2H6}$, (FIG. 11D) $S_{C2H4}$, (FIG. 11E) $Y_{C2H6}$, (FIG. 11F) $Y_{C2H4}$, (FIG. 11G) $\tilde{n}_{C2H6}$, and (FIG. 11H) $\tilde{n}_{C2H4}$. Marker-line equivalence: (1) T=750±3° C.: circles-dotted line, (2) T=800±3° C.: squares-dashed line, (3) T=850±3° C.: diamonds-dashed dotted line, and (4) T=900±4° C.: triangles-solid line. Lines are guides to the eye. The thickness of the membrane was 0.68 mm, while the thickness of the $La_2O_3$ catalyst layer was 1.5 mm.

FIGS. 12A-12H depict steady-state OCM measurements of BFZ91 with $La_2O_3$ as a function of T and $X^{in}_{CH4}$ in (FIG. 12A) $S_{H2O}$, (FIG. 12B) $Y_{H2O}$, (FIG. 12C) $S_{CO2}$, (FIG. 12D) $Y_{CO2}$, (FIG. 12E) $S_{H2}$, (FIG. 12F) $Y_{H2}$, (FIG. 12G) $S_{CO}$, and (FIG. 12H) $Y_{CO}$. Marker-line equivalence: (1) T=750±3° C.: circles-dotted line, (2) T=800±3° C.: squares-dashed line, (3) T=850±3° C.: diamonds-dashed dotted line, and (4) T=900±4° C.: triangles-solid line. Lines are guides to the eye. The thickness of the membrane was 0.68 mm, while the thickness of the $La_2O_3$ catalyst layer was 1.5 mm.

FIGS. 13A-13H depict steady-state species mole fractions near the $CH_4$ side of the BFZ91 membrane (measured using an alumina micro-probe) and at the outlet as a function of T and $X^{in}_{CH4}$. (FIG. 13A) $CH_4$ side $X^{mem}_{O2}$, (FIG. 13B) $CH_4$ side $X^{out}_{O2}$, (FIG. 13C) $X^{mem}_{CH4}$, (FIG. 13D) $X^{out}_{CH4}$, (FIG. 13E) $X^{mem}_{CO2}$, (FIG. 13F) $X^{out}_{CO2}$, (FIG. 13G) $X^{mem}_{CO}$, and (FIG. 13H) $X^{out}_{CO}$. Marker-line equivalence: (1) T=750±3° C.: circles-dotted line, (2) T=800±3° C.: squares-dashed line, (3) T=850±3° C.: diamonds-dashed dotted line, and (4) T=900±4° C.: triangles-solid line. Lines are guides to the eye. The thickness of the membrane was 0.68 mm, while the thickness of the $La_2O_3$ catalyst layer was 1.5 mm.

FIGS. 14A-14H depict steady-state species mole fractions near the $CH_4$ side of the BFZ91 membrane (measured using an alumina microprobe) and at the outlet as a function of T and $X^{in}_{CH4}$. (FIG. 14A) $X^{mem}_{C2H6}$, (FIG. 14B) $X^{out}_{C2H6}$, (FIG. 14C) $X^{mem}_{C2H4}$, (FIG. 14D) $X^{out}_{C2H4}$, (FIG. 14E) $X^{mem}_{H2O}$, (FIG. 14F) $X^{out}_{H2O}$, (FIG. 14G) $X^{mem}_{H2}$, and (FIG. 14H) $X^{out}_{H2}$. Marker-line equivalence: (1) T=750±3° C.: circles-dotted line, (2) T=800±3° C.: squares-dashed line, (3) T=850±3° C.: diamonds-dashed dotted line, and (4) T=900±4° C.: triangles-solid line. Lines are guides to the eye. The thickness of the membrane was 0.68 mm, while the thickness of the $La_2O_3$ catalyst layer was 1.5 mm.

FIGS. 15A-15P depict selected performance metrics as a function of T and $\dot{n}^{in}_{CH4}/\dot{n}^{mem}_{O2}$: (FIG. 15A) $J_{O2}$, (FIG. 15B) $C_{CH4}$ ($y=51.01e^{-0.491x}+18.13e^{-0.04458x}$, $R^2=0.9921$), (FIG. 15C) $\tilde{n}^{out}_{C2H6}$, (FIG. 15D) $\tilde{n}^{out}_{C2H4}$, (FIG. 15E) $S_{C2H6}$, (FIG. 15F) $Y_{C2H6}$, (FIG. 15G) $S_{C2H4}$, (FIG. 15H) $Y_{C2H4}$, (FIG. 15I) $S_{H2O}$ ($y=43.95e^{-0.3387x}+54.71e^{-0.01155x}$, $R^2=0.9797$), (FIG. 15J) $Y_{H2O}$ ($y=46.16e^{-0.5083x}+9.798e^{-0.05599x}$, $R^2=0.9932$), (FIG. 15K) $S_{CO2}$ ($y=90.35e^{-0.6219x}+42.36e^{-0.04034x}$, $R^2=0.9279$), (FIG. 15L) $Y_{CO2}$ ($y=65.08e^{-0.7467x}+9.065e^{-0.09846x}$, $R^2=0.9859$), (FIG. 15M) $S_{H2}$, (FIG. 15N) $Y_{H2}$, (FIG. 15O) $S_{CO}$, and (FIG. 15P) $Y_{CO}$. Marker-line equivalence: (1) T=750±3° C.: circles-dotted line, (2) T=800±3° C.: squares-dashed line, (3) T=850±3° C.: diamonds-dashed dotted line, and (4) T=900±4° C.: triangles-solid line. When the data collapse on the same curve, the curve is plotted using a pink dashed line; see the caption of each subplot for the corresponding equation and the goodness of fit.

(FIG. 16A) $J_{O2}$ (black) as a function of time and $X^{in}_{CH4}$, (FIG. 16B) $C_{CH4}$ (red) and $C_{O2}$ (purple) as a function of time and $X^{in}_{CH4}$, and (FIG. 16C) $ñ^{out}_{C2H6}$ (pink), $ñ^{out}_{C2H4}$ (orange), and $ñ^{out}_{C2}$ (green) as a function of time in and $X^{in}_{CH4}$. Blue dotted lines correspond to instants of $X^{in}_{CH4}$ change. Measurements were conducted every 1 h. During the experiment, ambient air was flowing in the air side at $\dot{Q}_{air}$=200 sccm, while $CH_4$—Ar mixtures with $\dot{Q}^{total}_{air}$=100 sccm were introduced in the $CH_4$ side. The thickness of the membrane was 0.66 mm, while the thickness of the $La_2O_3$ catalyst layer was 1.5 mm.

(FIG. 17A) $J_{O2}$ (black) and $C_{CH4}$ (red) as a function of time and (FIG. 17B) $ñ^{out}_{C2H6}$ (pink), $ñ^{out}_{C2H4}$ (orange), and $ñ^{out}_{C2}$ (green) as a function of time in. Measurements were conducted every 4 min. During the experiment, ambient air was flowing in the air side at $\dot{Q}_{air}$=200 sccm while pure $CH_4$ with $\dot{Q}_{CH4}$=100 sccm was introduced in the $CH_4$ side. The thickness of the membrane was 0.66 mm, while the thickness of the $La_2O_3$ catalyst layer was 1.5 mm.

FIGS. 21A-21B depict XRD patterns of: (FIG. 21A) the uncalcined BFZ91 powder (i.e. raw ash), and (FIG. 21B) the BFZ91 powder calcined at 950° C. for 4 h.

FIGS. 22A-22P depict species mole fractions near the membrane and at the outlet as a function of T and $X^{in}_{CH4}$ for a BFZ91 membrane operating without $La_2O_3$. (FIG. 22A) $X^{mem}_{O2}$, (FIG. 22B) $X^{out}_{O2}$, (FIG. 22C) $X^{mem}_{CH4}$, (FIG. 22D) $X^{out}_{CH4}$, (FIG. 22E) $X^{mem}_{C2H6}$, (FIG. 22F) $X^{out}_{C2H6}$, (FIG. 22G) $X^{mem}_{C2H4}$, (FIG. 22H) $X^{out}_{C2H4}$, (FIG. 22I) $X^{mem}_{H2O}$, (FIG. 22J) $X^{out}_{H2O}$, (FIG. 22K) $X^{mem}_{CO2}$, (FIG. 22L) $X^{out}_{CO2}$, (FIG. 22M) $X^{mem}_{H2}$, (FIG. 22N) $X^{out}_{H2}$, (FIG. 22O) $X^{mem}_{CO}$, and (FIG. 22P) $X^{out}_{CO}$. Marker-line equivalence: 1) T=800±3° C.: squares-dashed line, 2) T=850±3° C.: diamonds-dashed dotted line, and 3) T=900±4° C.: triangles-solid line. Lines are guides to the eye. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.67 mm.

FIGS. 23A-23L depict species selectivity and yields as a function of T and $X^{in}_{CH4}$ for a BFZ91 membrane operating without $La_2O_3$. (FIG. 23A) $S_{C2H6}$, (FIG. 23B) $Y_{C2H6}$, (FIG. 23C) $S_{C2H4}$, (FIG. 23D) $Y_{C2H4}$, (FIG. 23E) $S_{H2O}$, (FIG. 23F) $Y_{H2O}$, (FIG. 23G) $S_{CO2}$, (FIG. 23H) $Y_{CO2}$, (FIG. 23I) $S_{H2}$, (FIG. 23J) $Y_{H2}$, (FIG. 23K) $S_{CO}$, and (FIG. 23L) $Y_{CO}$. Marker-line equivalence: 1) T=800±3° C.: squares-dashed line, 2) T=850±3° C.: diamonds-dashed dotted line, and 3) T=900±4° C.: triangles-solid line. Lines are guides to the eye. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.67 mm.

FIGS. 25A-25B depict SEM images of: (FIG. 25A) $La_2O_3$ powder after the end of the OCM measurements (image also shown in FIG. 10F), and (FIG. 25B) $La_2O_3$ powder calcined in ambient air at T=1025° C. for 24 h.

FIG. 26 depicts an experimental setup used to investigate the $C_2H_6$ and $C_2H_4$ non-oxidative dehydrogenation in the presence and absence of $La_2O_3$.

(FIG. 27A) $X^{out}_{C2H6}$, (FIG. 27B) $X^{out}_{C2H4}$, (FIG. 27C) $X^{out}_{H2}$, (FIG. 27D) $X^{out}_{C2H2}$, (FIG. 27E) $X^{out}_{CH4}$, and (FIG. 27F) $C^{out}_{sum}$. Marker-line equivalence: 1) measurements without $La_2O_3$: circles-solid line, 2) measurements with $La_2O_3$: squares-dashed line, and 3) equilibrium calculations: diamonds-dotted line.

FIGS. 28A-28B depict long-term performance of BFZ91 with $La_2O_3$ at T=850° C. under partial $O_2$ consumption conditions. a) $S_{H2O}$ (blue) and $S_{CO2}$ (red) as a function of time and $X^{in}_{CH4}$, and b) $Y_{CO}$ (silver), $Y_{C2H6}$ (green), $Y_{C2H4}$ (black) and $Y_{H2}$ (brown) as a function of time and $X^{in}_{CH4}$. Blue dotted lines correspond to instants of $X^{in}_{CH4}$ change. Measurements were conducted every 1 h. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.66 mm, while the thickness of the $La_2O_3$ catalyst layer was 1.5 mm.

(FIG. 29A) $Y_{H2O}$ (blue) and $Y_{CO2}$ (red) as a function of time and $X^{in}_{CH4}$, and (FIG. 29B) $Y_{CO}$ (silver), $Y_{C2H6}$ (green), $Y_{C2H4}$ (black) and $Y_{H2}$ (brown) as a function of time and $X^{in}_{CH4}$. Blue dotted lines correspond to instants of $X^{in}_{CH4}$ change. Measurements were conducted every 1 h. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.66 mm, while the thickness of the $La_2O_3$ catalyst layer was 1.5 mm.

(FIG. 30A) $X^{out}_{H2O}$ (blue) and $X^{out}_{CO2}$ (red) as a function of time and $X^{in}_{CH4}$, (FIG. 30B) $Y_{H2}$ (brown) and $Y_{CO}$ (silver) and as a function of time and $X^{in}_{CH4}$, and (FIG. 30C) $Y_{C2H6}$ (green) and $Y_{C2H4}$ (black) and as a function of time and $X^{in}_{CH4}$. Blue dotted lines correspond to instants of $X^{in}_{CH4}$ change. Measurements were conducted every 1 h. During the experiment, ambient air was flowing in the air side at $\dot{Q}_{air}$=200 sccm while $CH_4$—Ar mixtures with $\dot{Q}^{total}_{CH4-Ar}$=100 sccm were introduced in the $CH_4$ side. The thickness of the membrane was 0.66 mm, while the thickness of the $La_2O_3$ catalyst layer was 1.5 mm.

FIGS. 31A-31B depict long-term performance of BFZ91 with $La_2O_3$ at T=850° C. under undiluted $CH_4$ conditions. (FIG. 31A) Species selectivities as a function of time, and (FIG. 31B) species yields as a function of time. Measurements were conducted every 4 min. During the experiment, ambient air was flowing in the air side at $\dot{Q}_{air}$=200 sccm while $CH_4$ mixtures with $\dot{Q}_{CH4}$=100 sccm were introduced in the $CH_4$ side. The thickness of the membrane was 0.66 mm, while the thickness of the $La_2O_3$ catalyst layer was 1.5 mm.

FIGS. 32A-32B depict XRD patterns of: (FIG. 32A) the as-prepared and used BFZ91 pellet, and (FIG. 32B) the as-received and used $La_2O_3$ catalyst. Patterns correspond to the long-term measurements reported in FIGS. 16A-16C (partial $O_2$ consumption case) and FIGS. 17A-17B (undiluted $CH_4$ case).

FIGS. 33A-33C depict SEM images of: (FIG. 33A) the air side of the used BFZ91 pellet, (FIG. 33B) the $CH_4$ side of the used BFZ91 pellet, and (FIG. 33C) the used $La_2O_3$ catalyst. SEM images correspond to the long-term measurements reported in FIGS. 16A-16C (partial $O_2$ consumption case) and FIGS. 17A-17B (undiluted $CH_4$ case).

DETAILED DESCRIPTION

Figure 1:
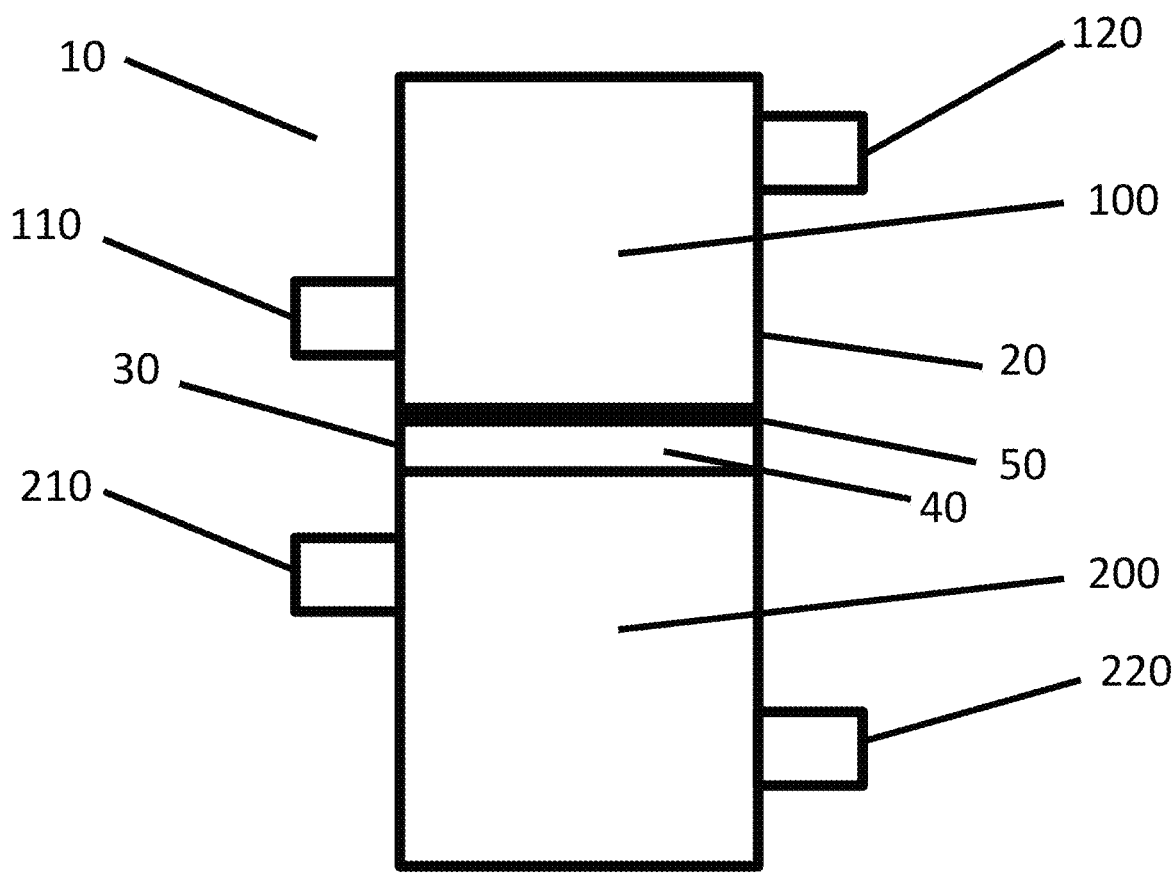
FIG. 1 depicts a reactor.
Figure 2:
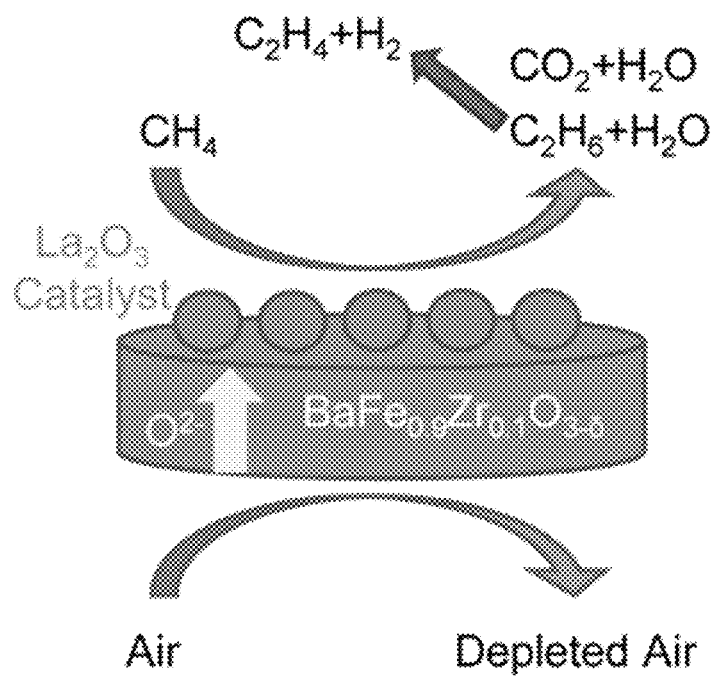
FIG. 2 is a schematic example of the catalytic system described herein.

In general, highly durable $C_2$ hydrocarbon production via the oxidative coupling of methane using a $BaFe_{0.9}Zr_{0.1}O_{3-\delta}$ mixed ionic and electronic conducting membrane and a $La_2O_3$ catalyst is described. The oxidative coupling of methane (OCM) is an attractive technology for the production of ethane ($C_2H_6$) and ethylene ($C_2H_4$); and significant performance and efficiency gains as well as reduced carbon dioxide ($CO_2$) emissions are expected when OCM takes place within mixed ionic and electronic conducting (MIEC) ceramic membrane reactors (CMRs). So far, research on OCM in CMRs has been limited to unstable and incompatible materials investigated under short-term measurements that hinder upscaling and commercial application. Unexpectedly, long-term stable OCM performance is enabled by a $BaFe_{0.9}Zr_{0.1}O_{3-\delta}$ (BFZ91) perovskite utilized as the oxygen-ion MIEC membrane and lanthanum oxide ($La_2O_3$) used as the OCM catalyst. Experimental measurements conducted in the temperature (T) range of 750-900° C. and at inlet methane ($CH_4$) mole fractions ($X^{in}_{CH4}$) of 0-30% revealed highly stable performance during 23 days of continuous operation, which was further confirmed by material characterization. Under the aforementioned operating conditions, BFZ91 offers a high oxygen ($O_2$) permeation flux ($J_{O2}$) between 0.5-1.5 ($\mu mol/cm^2/s$); $CH_4$ conversion ($C_{CH4}$) reached ~35% while the selectivities to $C_2H_6$ ($S_{C2H6}$) and $C_2H_4$ ($S_{C2H4}$) were as high as ~50% and ~40%, respectively, showing a strong dependency on the operating conditions. Yields of $C_2H_6$ ($Y_{C2H6}$) and $C_2H_4$ ($Y_{C2H4}$) in the range of 1-5% and 1-7%, respectively, were measured, with more $C_2H_4$ being produced at higher T. In the absence of $La_2O_3$, $C_{CH4}$ and $C_2$ ($C_2H_6$ and $C_2H_4$) yields are lower confirming that BFZ91 does not promote $CH_4$ oxidation, reforming, or coupling on its surface at high rates. The OCM performance of BFZ91 with $La_2O_3$ was also found to be stable under partial $O_2$ consumption and pure $CH_4$ conditions. Furthermore, a detailed analysis of the mixture composition allowed the identification of the primary reactions in the OCM chemistry. The results reveal that within the reactor, $CH_4$ full oxidation to $CO_2$ and steam ($H_2O$) happens simultaneously with $CH_4$ oxidation to $C_2H_6$ and $H_2O$ (both on the $La_2O_3$ catalyst), but the production of the valuable $C_2H_4$ is primarily taking place through the $C_2H_6$ non-oxidative dehydrogenation in the gas phase; this reaction was not found to proceed on the $La_2O_3$ catalyst.

$C_2H_4$ is primarily produced by steam cracking of naphtha or ethane (see refs. 3, 6) but other feedstocks such as propane, butane, and gas oil are also used. (See ref. 7) Naphtha is the main feedstock in Europe and Asia while ethane crackers are mostly used in North America and the Middle East. (See ref. 8) Steam-cracking reactions are highly endothermic and take place at temperatures between 750-950° C. (See ref. 7) From an energy consumption and yield point of view, when using $C_2H_6$ as the feedstock, the process requires ~12.5-21 GJ per ton of produced $C_2H_4$ and $C_2H_4$ yields are as high as ~80%. (See refs. 7, 9) For naphtha, the process becomes more energy intensive and requires ~14-22 GJ per ton of produced $C_2H_4$, while the $C_2H_4$ yields drop significantly to ~30% because of the formation of various byproducts such as methane, propylene, butane, and other fuel oils. (See refs. 7, 9) For naphtha, one also has to account for variations in its composition which affect the final product yield. (See ref. 7) Besides the high energy requirements and the corresponding $CO_2$ emissions, cracking reactions are thermodynamically limited because of species accumulation in the reactor (e.g., $H_2$ formation from $C_2H_6$ pyrolysis). Moreover, $C_2H_6$ and naphtha crackers suffer from severe carbon deposition, a safety hazard that requires periodic shutdown. (See ref. 6) Finally, the purification of $C_2H_4$ is another challenge with a significant energy penalty given that it is based on high-pressure cryogenic distillation taking place at temperatures of –160° C. (See ref. 10).

An alternative to the production of $C_2H_4$ is the oxidative coupling of methane (OCM). The process was first suggested by Keller and Bhasin (see ref. 11), and it involves co-feeding $CH_4$ and $O_2$ in a single stream, which react in the presence of a catalyst at T=650-900° C. to produce $C_2$ as follows:

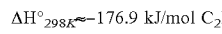 (1)

$\Delta H°_{298K}$≈–281.8 kJ/mol $C_2H_4$ (2)

OCM has several advantages when compared to steam cracking including (see ref. 12): (1) reduced energy consumption because of the reaction exothermicity resulting in fewer $CO_2$ emissions; the feedstock is natural gas (composed primarily of $CH_4$), which is currently cheap ($2.3-3/GJ) and widely produced in the US from shale reserves with future production increase from gas hydrate exploitation; (3) lower cost, due to the direct conversion of $CH_4$ to $C_2$ without the need for intermediate steps that require the use of syngas; and (4) formation of $H_2O$ in the products because of the $CH_4$ reaction with $O_2$ removes equilibrium limitations and reduces downstream separation costs. However, OCM has four important challenges: (1) the process is kinetically controlled because at equilibrium, $CH_4$ partial or full oxidation takes place (see ref. 13); (2) the produced $C_2$ species can pyrolyze at the OCM operating T and this creates the need to reduce the T and the residence time at the expense of catalyst performance and $CH_4$ conversion, respectively; (3) the process requires a selective and long-term stable catalyst to drive the reaction at relatively low T; and (4) $CH_4$ oxidation forms byproducts, such as carbon monoxide (CO), $CO_2$, and so forth, that reduce the $C_2$ selectivity and yield.

Co-feeding $CH_4$ and $O_2$ in a single-stream reactor relies on a fixed-bed catalyst to drive OCM. However, this conventional OCM technology has three major limitations: (1) it needs pure $O_2$, whose production is based on cryogenic air separation, and hence, creates a significant energy penalty (see ref. 14); (2) while the OCM stoichiometric $CH_4/O_2$ ratio for $C_2H_4$ production is 2 (reaction 2), in practice, ratios of 5-10 are required to avoid deep oxidation of $CH_4$, and hence, most of it remains unconverted or forms undesired species; and (3) the reaction exothermicity (reactions 1 and 2) combined with nonuniform conversion along the catalyst bed results to large T gradients, which is a safety risk and could lead to local catalyst deactivation along the reactor, thus reducing the $C_2$ yields further.

Despite intense research to design selective OCM catalysts, only one commercial reactor has been reported to date but its $C_2$ yield is currently unknown. (See refs. 12, 15 and 16). Early techno-economic analyses proposed that economic viability of the conventional OCM process requires a single-pass $C_2H_4$ yield higher than 25%. (See refs. 12, 17 and 18) However, more recent investigations focusing on $C_2H_4$ production in Europe propose that the fuel-to-chemicals efficiency of naphtha crackers can be achieved from conventional OCM only if single-pass $C_2H_4$ yields around 45-50% can be obtained. (See, refs. 19, 20). Similar studies show that besides efficiency, the $C_2H_4$ price from plants employing the conventional OCM technology can compete with naphtha crackers only if OCM yields higher than 30% can be achieved. (See ref. 21) This is because of the large capital cost of units required to separate $C_2$ from the gaseous stream, and the recombination of syngas (produced from secondary reactions) back to $CH_4$ (see refs. 10, 21). Operating expenses related to the cost of natural gas and electricity significantly affect the $C_2H_4$ production price. (See ref. 21) To decrease the cost it has been suggested that the target yields should be achieved with high $C_2$ selectivity catalysts compared to high $CH_4$ conversion catalysts. (See ref. 21)

An alternative technology for OCM that has the potential to improve upon the conventional OCM relies on oxygen-ion conducting ceramic membrane reactors (CMRs). A recent techno-economic analysis suggested that the price of $C_2H_4$ produced from membrane-based OCM plants could potentially compete with naphtha crackers if $C_2H_4$ yields higher than 30% can be achieved. (See ref. 22) Note, however, that estimating the price of a membrane reactor has its own challenges given that the large-scale deployment of these reactors has so far been limited. The same study also confirms that significant $CO_2$ emission reduction can be attained with CMRs. (See ref. 22) OCM in CMRs enables process intensification given that pure $O_2$ can be separated from an $O_2$ containing gaseous stream and be converted to added-value chemicals in the same reactor, hence reducing the reactor size and cost. In addition, given that increased $CH_4/O_2$ ratios generally allow for higher $C_2$ selectivity (see ref. 13), it has been demonstrated that CMRs offer higher $C_2$ selectivity compared to the conventional OCM. (See refs. 13, 23-25) Moreover, the gradual introduction of $O_2$ through the membrane allows for a better thermal management with decreased T gradients. Finally, OCM in CMRs takes place along the entire reactor length in contrast to conventional fixed-bed OCM reactors, where the $C_2$ production is confined at the initial stages of the catalyst followed by the pyrolysis of the desired species or by secondary undesired reactions that reduce the $C_2$ yield. (See ref. 26) It is evident that in OCM with CMRs, the design of the reactor (its geometry, in particular) is another important variable that needs to be explored and optimized.

CMRs consist of two different gaseous streams separated by a ceramic oxide material. (See refs. 12, 14 and 27) Membrane materials commonly used in oxygen-ion CMRs exhibit mixed ionic and electronic conductivity and hence allow the transport of $O_2$ (in the form of ions) from a high $O_2$ chemical potential ($\mu_{O2}$) stream to a low $\mu_{O2}$ stream without external polarization, that is, it is a purely thermochemical process driven by surface reactions on the gas-membrane interfaces coupled with the diffusion of charged species (oxygen vacancies, small polarons etc.) within the material. When air is introduced on one stream (the air side) and $CH_4$ on the other (the $CH_4$ side), $O_2$ is converted to oxygen ions ($O^{2-}$) on the air side surface, which are then incorporated into the material. $O^{2-}$ diffuse through the membrane to the $CH_4$ side via an oxygen vacancy-mediated mechanism that also involves the transport of electrons and electron holes to preserve charge neutrality in the bulk of the material. (See refs. 28-31) At the $CH_4$ side surface, $CH_4$ may react either with $O^{2-}$ directly on the surface or with desorbed $O_2$ in the gas phase. In the presence of a catalyst, $O_2$ and $CH_4$ react on its surface to form $C_2$ species and other products.

The success of OCM in CMRs requires a membrane-catalyst configuration that can operate with acceptable $J_{O2}$ and high $C_2$ yields under long times without the formation of undesired phases that could degrade the performance. The former, that is, the value of $J_{O2}$, is a challenge in CMRs because $J_{O2}$ can only be controlled indirectly by the operating conditions and the membrane properties. These establish a $\mu_{O2}$ gradient along the two membrane sides and do not allow for the direct control of $O_2$ through the membrane. The latter, that is, undesired phases, can arise because of: (1) decomposition of the material on the OCM side due to operation under a low partial pressure of $O_2$ ($P_{O2}$); (2) cation segregation from the bulk to the surface induced by elastic and electrostatic interactions (see ref. 32); (3) reaction of the materials with gaseous species (e.g., formation of stable surface carbonate species because of $CO_2$ in the gaseous stream); and (4) reaction of the membrane with the OCM catalyst forming undesired phases. (See ref. 33)

Prior work on OCM using oxygen-ion conducting CMRs has focused on the development of membrane-catalyst materials (see refs. 34, 35) with high $J_{O2}$ and increased $C_2$ selectivity and yield. Unfortunately, the trend in OCM is that high $C_2$ selectivity is accompanied by low $CH_4$ conversion and vice versa, and this limits the maximum $C_2$ yield that can be obtained. For example, Igenegbai et al. investigated OCM using dense $BaCe_{0.8}Gd_{0.2}O_{3-\delta}$ (BCG) and nickel-doped $La_{0.8}Sr_{0.2}Ga_{0.8}Mg_{0.2}O_{3-\delta}$ (LSGM) disk-shaped membranes employing BCG and LSGM porous supports, respectively, acting as OCM catalysts. (See ref. 36) Stable operation with $C_{2+}$ ($C_2H_6$, $C_2H_4$ and higher hydrocarbons) selectivity of ~80% was achieved at T=810° C. with the former, while degradation was observed for the latter because of carbon deposition. (See ref. 36) Despite the high selectivity, a $C_{2+}$ yield of ~1-2% was obtained because of low $CH_4$ conversion. (See ref. 36) Garcia-Fayos et al. used $Ba_{0.5}Sr_{0.5}Co_{0.8}Fe_{0.2}O_{3-\delta}$ (BSCF) membranes and screened several catalysts. (See ref. 37) $C_{2+}$ yields of ~15% were obtained at 900° C. when using a tubular membrane packed with a 2 wt % $Mn_xO_y$, 5 wt % $Na_2WO_4$ catalyst supported on $SiO_2$; $C_{2+}$ yields were lower when a disk-shaped membrane configuration was employed. (See ref. 37) Othman et al. investigated the performance of $Bi_{1.5}Y_{0.3}Sm_{0.2}O_{3-\delta}$ (BYS) catalysts deposited on $La_{0.6}Sr_{0.4}Co_{0.2}Fe_{0.8}O_{3-\delta}$ (LSCF) hollow fiber membranes (see ref. 38); they found that an in situ preparation-deposition of the catalyst on the membrane is superior when compared to the traditional wash-coat deposition method. $C_{2+}$ selectivity and yield of 79 and 39%, respectively, were obtained at 900° C. Tan et al. also used LSCF hollow fiber membranes with the $SrTi_{0.9}Li_{0.1}O_{3-\delta}$ catalyst (see ref. 39); at 975° C., they obtained a maximum $C_2$ yield of ~21%. Akin and Lin investigated OCM within tubular BYS membranes (see ref. 25); at 900° C., $C_2$ selectivity and yield of 54 and 35% were obtained, respectively. In a similar work using disk-shaped BYS membranes, Zeng and Lin showed that the $C_2$ selectivity and yield at 900° C. were 35 and 8%, respectively, thus highlighting once more the influence of the membrane geometry and the membrane-catalyst choice on the $C_2$ yield. (See ref. 40)

Although some of the aforementioned membrane-catalyst systems can deliver $C_2$ yields higher than early and recent target values (see refs. 17-19, 21, 22), their long-term stability is a major concern. For example, BSCF membranes are known to decompose under reducing conditions (see ref. 41) and to form barium carbonates at high T even with traces of $CO_2$ from air under long-term operation (see ref. 42); on the OCM side, the degradation is more intense because of increased $CO_2$ concentrations. (See ref. 43) In addition, the reaction of barium in BSCF with the $SiO_2$ support of the $Mn_xO_y$—$Na_2WO_4$ catalyst is thermodynamically favorable under OCM conditions. This reaction forms insulating barium-silicon oxide layers on the OCM side, hence reducing $J_{O2}$ and the $C_2$ yield. (See refs. 37, 44) LSCF is also unstable and prone to decomposition in a reactive environment (see refs. 45, 46), while the reaction with $SiO_2$ is unavoidable (see refs. 47, 48). For LSCF, strontium oxide and cobalt oxide surface segregation have been reported in the literature and are expected to reduce the performance under long-term operation. (See ref. 49) Moreover, the transition of the $SiO_2$ catalyst support from the α-cristobalite phase to the amorphous phase observed at T≥750° C. reduces the $C_2$ selectivity and confirms a clear correlation between OCM activity and catalyst support. (See refs. 50, 51). BCG was also found to partially decompose under OCM conditions, but this effect was not shown to decrease the $C_{2+}$ yields as a function of time when $CH_4$ and air were co-fed in a single chamber reactor. (See ref. 33) The addition of zirconium (Zr) in the B-site gave similar OCM performance compared to BCG and improved the resistance to decomposition (see ref. 33); however, the decomposition was not eliminated completely showing that under long term, the material does not survive the OCM conditions. Volatile elements should also be avoided as they impact the long-term stability. For example, bismuth oxide ($Bi_2O_3$) has a melting point equal to 817° C.; operation above this temperature results in the loss of bismuth because of evaporation. (See refs. 52, 53) Evaporation has also been observed for lithium at 800° C. (See refs. 54-56) These membrane-catalyst instabilities clearly demonstrate that research on OCM in CMRs should focus both on material performance and stability, which should be demonstrated under the long-term operation.

To meet the aforementioned performance and long-term stability criteria, the present work investigates OCM using a BFZ91 ceramic membrane coupled with $La_2O_3$ powder. BFZ91 has been shown to deliver a high $J_{O2}$ and to be stable structurally and in the presence of different hydrocarbon environments (see refs. 57, 58), while $La_2O_3$ is one of the most active and stable OCM catalysts among the various doped and undoped rare earth oxides. (See refs. 59-62) Both BFZ91 and $La_2O_3$ were characterized prior to the OCM measurements, and trends related to their properties are investigated and discussed. In the absence of $La_2O_3$, the BFZ91 membrane is relatively inactive toward the catalytic $CH_4$ decomposition or oxidation, and hence, it serves as a means to separate $O_2$ from air without converting much $CH_4$ to the (un)desired products. In the presence of $La_2O_3$, long-term measurements conducted in a button-cell reactor demonstrate that the BFZ91-$La_2O_3$ combination is highly stable for 23 days in the stream, during which the temperature and inlet $CH_4$ mole fraction were varied between T=750-900° C. and $X^{in}_{CH4}$=0-30%, respectively. This is further confirmed by post-mortem material characterization showing the absence of secondary phases. This appears to be the first time that materials with such a prolonged OCM lifetime are reported for the CMR technology. $J_{O2}$, $C_{CH4}$, $C_2H_6$ and $C_2H_4$ selectivity, yield, and activity (i.e., molar production rate scaled to the catalyst mass) ($\dot{n}_i$) are used as performance metrics. These results confirm that $J_{O2}$ is limited by both bulk diffusion and surface reactions at T=750-800° C.; higher fluxes are obtained at T=850-900° C., during which surface reactions at the $CH_4$ side are accelerated. The maximum $Y_{C2}$ is ~10% and it is obtained at T=850° C. and $X^{in}_{CH4}$=5% during which $J_{O2}$≈0.91 (μmol/cm²/s) and $S_{C2}$~39%. Experiments under partial $O_2$ consumption and pure $CH_4$ conditions also demonstrated a stable performance. For the latter, secondary phases were detected on the $CH_4$ side because of the highly reducing conditions under pure $CH_4$; however, this 3-day measurement showed no loss of performance as a function of time. Finally, the analysis of the gas-phase mixture composition near the $CH_4$ side of the membrane but within the $La_2O_3$ bed and comparison with outlet values allows to determine the primary reactions involved in the OCM chemistry. $CH_4$ full oxidation to $CO_2$ and $H_2O$, $CH_4$ oxidative coupling to $C_2H_6$ and $H_2O$ and $C_2H_6$ non-oxidative dehydrogenation to $C_2H_4$ and $H_2$ are identified as the key OCM reactions within the reactor. It was shown that the first two reactions happen on the $La_2O_3$ catalyst, while the third is only taking place in the gas phase. This finding is important because it demonstrates that $La_2O_3$ facilitates the formation of $C_2H_6$ but the production of $C_2H_4$ within the reactor happens primarily in the gas phase through the non-oxidative dehydrogenation of $C_2H_6$ (NODHE).

FIG. 1 depicts a reactor for oxidative coupling of methane. Referring to FIG. 1, reactor 10 includes housing 20. Housing 20 includes first chamber 100 and second chamber 200. First chamber 100 and second chamber 200 are separated by ceramic membrane 30. Ceramic membrane 30 includes perovskite oxide 40 and catalyst 50. Catalyst 50 is downstream from the perovskite oxide 40. In one example, catalyst 50 can be in contact with an interior gas space of first chamber 100, as shown. In another example (not shown), catalyst 50 can be located in first chamber 100 decoupled from the perovskite oxide 40, in which case oxygen is first separated from air through the perovskite oxide and is then mixed with methane creating a mixture of $CH_4$—$O_2$ which is then activated on the catalyst downstream of the perovskite oxide. Perovskite oxide 40 is in contact with an interior gas space of second chamber 200. First chamber 100 can be configured for a first gas flow through the chamber via first chamber inlet 110 and first chamber outlet 120. A reactant gas can be present in the first gas flow at first chamber inlet 110. One or more product gases can be present in the first gas flow at first chamber outlet 120. The reactant gas can include methane. The product gasses can include $C_2$ hydrocarbons. Second chamber 200 can be configured for a second gas flow through the chamber via second chamber inlet 210 and second chamber outlet 220. A reactant gas, such as oxygen, can be present in the first gas flow at second chamber inlet 210. One or more product gasses can be present in the second gas flow at second chamber outlet 120. The oxygen can be oxygen in air or oxygen in a carrier gas, such as an inert carrier gas, for example, argon or oxygen from other oxygen-containing gases such as $H_2O$ and $CO_2$.

The ceramic membrane can include a perovskite oxide having the formula $BaBO_{3-\delta}$, wherein B is Fe or Zr, or mixtures thereof, and $\delta$ is 0 to 0.6. The ceramic membrane can include a catalytic metal distributed on a surface of the perovskite oxide of the membrane. B can be a mixture of Fe and Zr. For example, the mixture of Fe and Zr can be between 1% and 20% Zr, preferably between 2% to 15% Zr. In the formulation, $\delta$ can be 0 to 0.6, preferably 0.1 to 0.55, or more preferably 0.15 to 0.5. In preferred embodiments, the perovskite oxide can be $BaFe_{0.9}Zr_{0.1}O_{3-\delta}$, for example, the perovskite oxide can be $BaFe_{0.9}Zr_{0.1}O_{2.56}$.

Properties of the perovskite oxide can depend on physical characteristics of the material. For example, the perovskite oxide can have a unit cell lattice constant of 4.022 Å or greater.

For oxidative coupling of methane, the catalytic material can be a lanthanum oxide, for example, $La_2O_3$. The catalytic material can be downstream of the ceramic membrane or in contact to the surface of the ceramic membrane. When the catalytic material is downstream of the ceramic membrane, the catalytic material can be in the form of a powder creating a fixed-bed type configuration. When the catalytic material is in contact to the surface of the ceramic membrane, the catalytic material can be in the form of a porous electrode or a powder creating a fixed-bed type configuration. The catalytic material can be a powder on a surface of the perovskite oxide of the membrane. In certain circumstances, the lanthanum oxide catalyst can be substantially free of other metals. For example, the lanthanum oxide catalyst can be substantially free of strontium or calcium. In another example, the lanthanum oxide catalyst can be substantially free of lanthanum hydroxides, lanthanum carbonates or combinations thereof. In certain circumstances, the lanthanum oxide catalyst can be modified. For example, the lanthanum oxide catalyst can include alkaline earth metals, transition metals or lanthanides. For example, the modified lanthanum oxide can be produced through doping in the bulk or through surface modification using methods such as incipient wet impregnation. When substantially free of other metals, the purity of the $La_2O_3$ can be greater than 97%, greater than 98%, greater than 99% or greater than 99.9%.

The reactor and ceramic membrane can be used in a method of manufacturing $C_2$ hydrocarbons. The method can include contacting a first gas including oxygen with a first surface of a ceramic membrane described herein; and contacting a second gas including methane with a second surface of the ceramic membrane, thereby generating a $C_2$ hydrocarbon. For example, a method of manufacturing $C_2$ hydrocarbons can include contacting a first gas including methane with a first surface of a ceramic membrane comprising a perovskite oxide having the formula $BaBO_{3-\delta}$, wherein B is Fe or Zr, or mixtures thereof, and $\delta$ is 0 to 0.6 and a lanthanum oxide catalyst on the first surface of the perovskite oxide of the membrane and contacting a second gas including oxygen with a second surface of the ceramic membrane, the second surface opposite the first surface, thereby generating $C_2$ hydrocarbons. In certain circumstances, the $C_2$ hydrocarbon can include ethane or ethylene.

In certain circumstances, the $C_2$ hydrocarbons can include $C_2H_6$ and $C_2H_4$. In certain circumstances, $C_2H_4$ can be favored over $C_2H_6$. In certain circumstances, the $C_2$ hydrocarbons can include $C_2H_2$. The ratio of $C_2$ hydrocarbons can vary with reaction conditions. The method of manufacturing $C_2$ hydrocarbons can include heating a reactor including the ceramic membrane to a temperature between 650° C. and 1100° C., preferably between 700° C. and 900° C.

The perovskite oxide is synthesized by wet chemical methods. In one example, a method of making a perovskite oxide can include dissolving a barium salt, an iron salt, and a zirconium salt in a solvent to form a precursor solution. The solvent can be a protic solvent, such as an alcohol or water. The solution can include an organic acid, for example, formic acid, acetic acid, propanic acid, citric acid, maleic acid, or other carboxylic acid. The solution can also include a chelating agent, for example, a multidendate ligand, such as ethylenediaminetetraacetic acid or acetylacetonate. When citric acid (CA) and ethylenediaminetetraacetic acid (EDTA) are used, a ratio of total metal cations:CA:EDTA can be 1:1.5:1.

Once dissolved the pH of the precursor solution can be increased by adding a base. For example, an ammonia solution can be added to increase the pH to a more basic value. For example, the pH can be increased to at least 6.8, 6.6, 6.4, 6.2, 6.0, 5.8, 5.6, 5.4, 5.2, 5.0, 4.8, 4.6, 4.4, 4.2, or 4.0.

The adjusted pH mixture can be dried to form an ash. The drying step can be by application of heat on a hot plate or in an oven. The temperature for drying can be greater than 350° C., greater than 400° C., greater than 450° C., greater than 500° C. or greater than 520° C., for example, 520° C. The drying can be in an inert atmosphere or in air.

The ash can be ground into a powder before calcining. The ash can be heated to between 800° C. and 1100° C., preferably, between 900° C. and 1000° C. to calcine the material. The calcination step can take place in air.

In certain circumstances, the method of making a perovskite oxide can include sintering the perovskite oxide at 1250° C. or less, for example, 1200° C. This sintering step can form a disc or other shape for the membrane.

Unexpectedly, the perovskite oxide made as described herein has significantly improved stability over similar barium iron zirconium oxides made by more traditional methods. The stability is marked in the oxidative reactors described herein, where membranes with other compositions or made by other methods degrade rapidly due to the existence of secondary phases. Also unexpected is the overall yield and selectivity of the $C_2$ hydrocarbon products obtained with the barium iron zirconium oxide/lanthanum oxide catalyst membrane described herein. More details of these experiments are described below.

EXPERIMENTAL SECTION

1. Material Synthesis. The BFZ91 powder was synthesized using a combined citric acid (CA)-ethylenediaminetetraacetic acid (EDTA) method. To form the perovskite oxide, stoichiometric amounts of $Ba(NO_3)_2$ (99.999%-Alfa Aesar), $Fe(NO_3)_3 \cdot 9H_2O$ (≥99.95%-MilliporeSigma) and $ZrO(NO_3)_2 \cdot xH_2O$ (99.99%-MilliporeSigma) were first dissolved in purified water and subsequently mixed with CA (≥99.5%-MilliporeSigma) and EDTA (99.995%-MilliporeSigma) in a ratio of total metal cations:CA:EDTA=1:1.5:1. The value of x in $ZrO(NO_3)_2 \cdot xH_2O$ was estimated to be x=2.1 based on thermogravimetric analysis (TGA) of the precursor in synthetic air (21% $O_2$, balance $N_2$) from room temperature to 1000° C.; similar values have been reported in the literature. (See ref. 63) The pH of the solution was adjusted to 6 using $NH_3 \cdot H_2O$ (28% $NH_3$ in $H_2O$, ≥99.99%-MilliporeSigma). The solution was dried and combusted on a hot plate at 540° C., and the obtained raw ash was first ground with a mortar and pestle, and then, it was calcined at 950° C. for 4 h in ambient air to form the final perovskite structure using a heating and cooling rate of 5° C./min.

$La_2O_3$ powder was purchased from MilliporeSigma (99.999%) and was used as received without any modification or pre-treatment.

2. Preparation of Dense BFZ91 Pellets for OCM Measurements. To prepare dense, disk-shaped BFZ91 pellets for OCM measurements, the calcined powder was mixed with 3 wt % polyvinyl butyral (acting as a binder) and ethanol and the mixture was homogenized in a mortar using a pestle. After ethanol evaporated, the powder-binder mixture was pressed uniaxially at 12 MPa in a cylindrical die to form the green body which was densified by sintering in ambient air at 1200° C. for 8 h using heating and cooling rates equal to 3° C./min. The sintered pellets had a final diameter of D≃16 mm and were then polished to the final thickness using silicon carbide sandpapers of different grit sizes until a smooth, mirror-like surface was obtained. The density of the final BFZ91 pellets was estimated using the Archimedes principle.

3. Button-Cell Reactor for OCM Measurements. Experimental measurements were obtained using a button-cell reactor shown below in FIG. 19. Additional information about the experimental setup is provided in the material below (Section 1) and in a previous work. (See, ref. 64) For the OCM measurements, 0.1 g of $La_2O_3$ powder were deposited on the $CH_4$ side of the BFZ91 membrane to create a fixed-bed type configuration, as shown in Figure S2.

Prior to any measurements, the reactor temperature was increased to 1025° C. with ambient air flowing in the air side (200 sccm) and pure argon (Ar) in the $CH_4$ side (100 sccm) and was maintained at these conditions overnight. This heat treatment is required to soften the gold rings so that they can attach well on the alumina tubes and on the membrane, thus ensuring a gas-tight system with minimized leaks. For all the experiments reported herein, the nitrogen ($N_2$) mole fraction at the exit of the $CH_4$ side of the reactor was below 0.1%, demonstrating that air leaks are negligible and do not affect the measurements.

To estimate $J_{O2}$, $C_{CH4}$, $O_2$ conversion ($CO_2$), $C_2$ selectivities, yields, and activities, measurements of species mole fractions at the inlet and outlet of the $CH_4$ side are used as the input to a mole balance system of equations. All relevant equations are reported below (Section 2). To understand the role of gas phase and surface reactions because of the presence of the BFZ91 membrane and $La_2O_3$ catalyst, measurements using an alumina micro-probe with outer and inner diameters equal to 1.6 and 0.8 mm, respectively, were conducted near the membrane surface (approximately 1 mm away) and within the $La_2O_3$ bed. Silica was used as a desiccant material to remove any $H_2O$ from the mixture prior to introduction into the gas chromatograph (GC) for analysis. To estimate the mole fraction of $H_2O$ near the membrane surface (but still in the gas phase), a carbon to hydrogen atom balance between that location and the $CH_4$ side inlet was used. (See ref. 29) Then, the GC measurements were corrected to estimate the true (i.e., on a wet basis) mole fraction of species within the reactor. (See ref. 29) The system of equations is reported below (Section 3). Experimental uncertainties are included in all plots; to highlight this, data are plotted using open markers. All species mole fractions reported in this work are plotted on a wet basis, that is, accounting for $H_2O$ in the mixture.

4. Material Characterization. The X-ray diffraction (XRD) patterns of the as-prepared, as-received, and used materials were obtained at room temperature with a PANalytical X'Pert Pro diffractometer using copper (Cu) Kα radiation operating at voltage and current equal to 45 kV and 40 mA, respectively. The patterns were recorded in the 2θ range of 20-80° and were analyzed using the software HighScore Plus. The same software was also used for phase identification and Rietveld refinement. Scanning electron microscopy (SEM) and energy-dispersive X-ray spectroscopy (EDS) were conducted using a Zeiss Merlin high-resolution scanning electron microscope. TGA measurements were conducted using a Q50 thermal analyzer from TA Instruments. Buoyancy corrections were included by repeating the TGA measurements at identical conditions using an empty sample pan. To estimate the surface area of the powder materials, the Brunauer-Emmett-Teller (BET) method was employed using an ASAP 2020 surface area analyzer from Micromeritics. To remove any moisture, the samples were degassed at T=150° C. for 30 min in vacuum prior to BET measurements. BET was conducted in $N_2$ and two measurements were performed for each material with a sample mass equal to ~0.5 g.

TABLE 1

Crystal Structure, Space Group, Lattice Constants and Phase Identification for: (1) the Calcined BFZ91 Powder (950° C. for 4 h), (2) the As-Prepared Dense BFZ91 Pellet (1200° C. for 8 h), (3) the As-Received $La_2O_3$ Powder, and (4) the As-Received $La_2O_3$ Powder after Heat-Treatment in Ambient Air at 800° C. for 2 h

| No. | Material | Phases | Crystal structure | Space group | Lattice constants (Å) | Phase % |
|---|---|---|---|---|---|---|
| 1 | calcined BFZ91 powder | $BaFe_{0.9}Zr_{0.1}O_{2.785}$ | cubic | Pm3m | a = b = c = 4.022 | 100.0 |
| 2 | as-prepared BFZ91 pellet | $BaFe_{0.9}Zr_{0.1}O_{2.636}$ | cubic | Pm$\bar{3}$m | a = b = c = 4.079 | 100.0 |

TABLE 1-continued

Crystal Structure, Space Group, Lattice Constants and Phase Identification for: (1) the Calcined BFZ91 Powder (950° C. for 4 h), (2) the As-Prepared Dense BFZ91 Pellet (1200° C. for 8 h), (3) the As-Received $La_2O_3$ Powder, and (4) the As-Received $La_2O_3$ Powder after Heat-Treatment in Ambient Air at 800° C. for 2 h

| No. | Material | Phases | Crystal structure | Space group | Lattice constants (Å) | Phase % |
|---|---|---|---|---|---|---|
| 3 | as-received $La_2O_3$ powder | $La_2O_3$ | hexagonal | $P\bar{3}m1$ | a = b = 3.937, c = 6.130 | 97.3 |
|  |  | $La(OH)_3$ | hexagonal | $P6_3/m$ | a = b = 6.538, c = 3.589 | 2.7 |
| 4 | powder heat-treated at 800° C. | $La_2O_3$ | hexagonal | $P\bar{3}m1$ | a = b = 3.937, c = 6.129 | 100.0 |

Results and Discussion

Figure 3A:
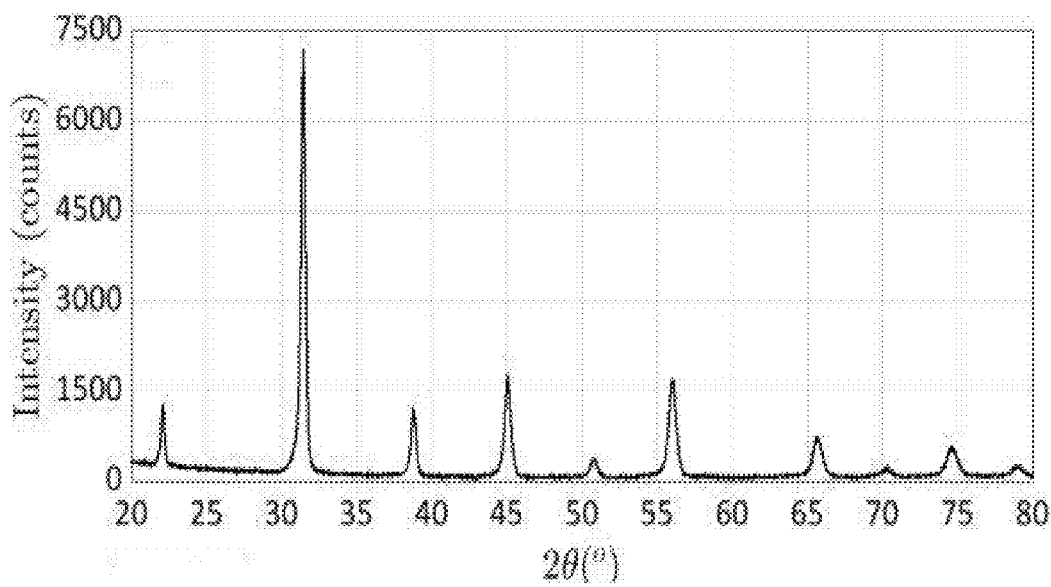
FIGS. 3A-3D are graphs depicting a comparison between the XRD pattern of the calcined BFZ91 powder (FIG. 3A, FIG. 3C) and that of the sintered BFZ91 pellet (FIG. 3B, FIG. 3D) prior to polishing.
Figure 3B:
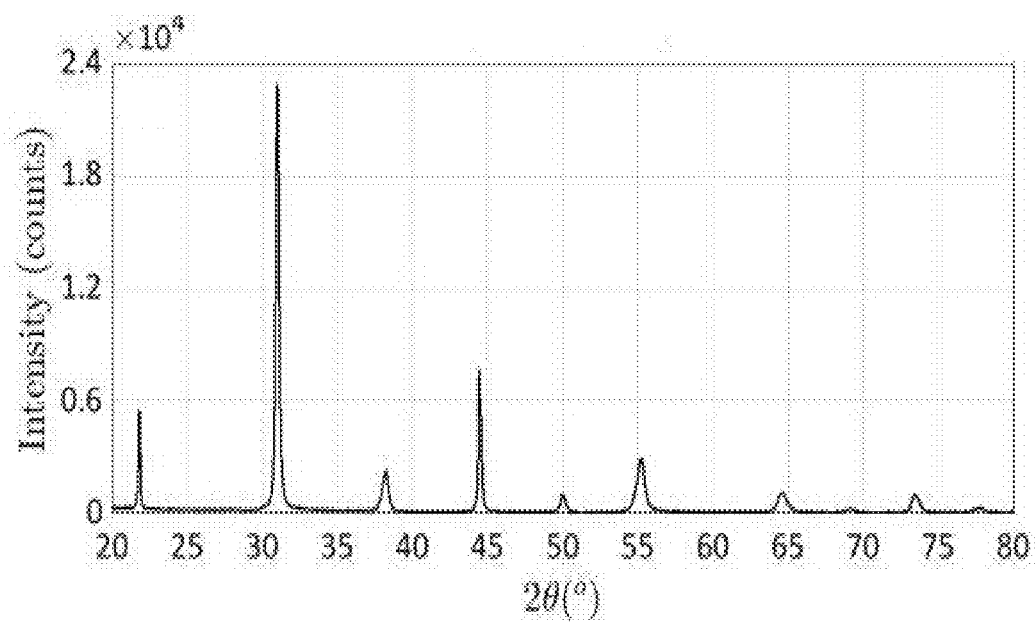
Figure 3C:
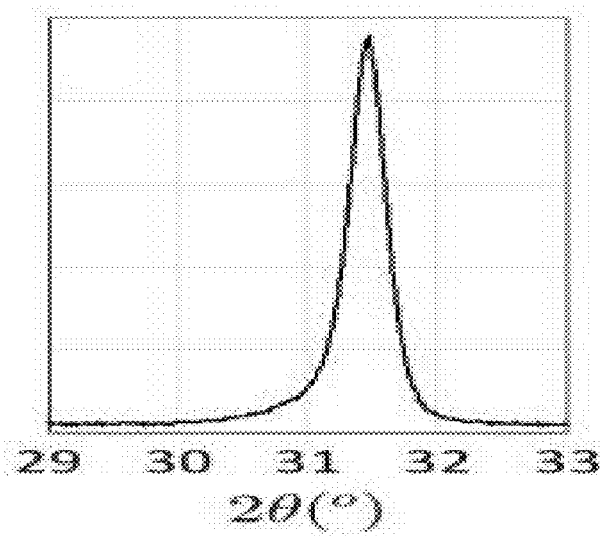
Figure 3D:
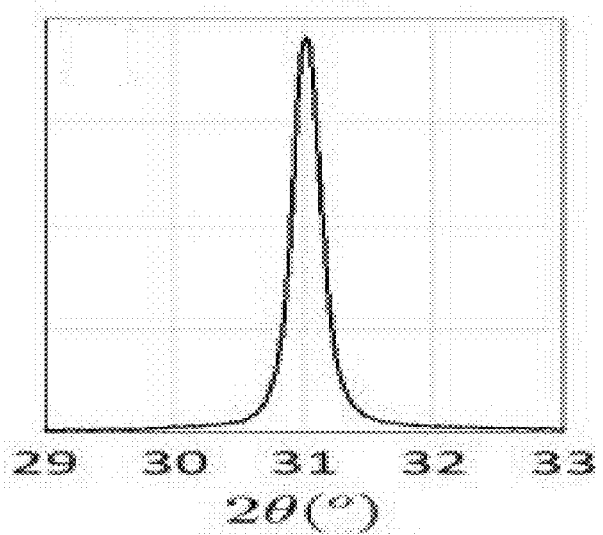
Figures 4A, 4B:
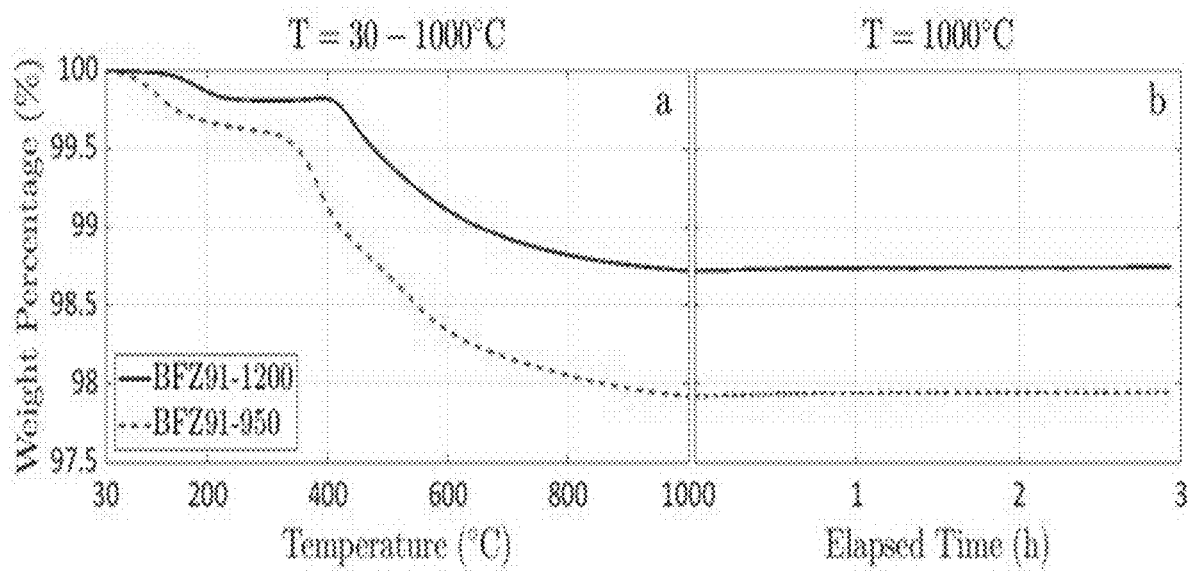
FIGS. 4A-4D depict TGA measurements in ambient air (100 sccm) between T=30-1000° C. for BFZ91-950 (red dashed line) and BFZ91-1200 (blue solid line).
Figures 4C, 4D:
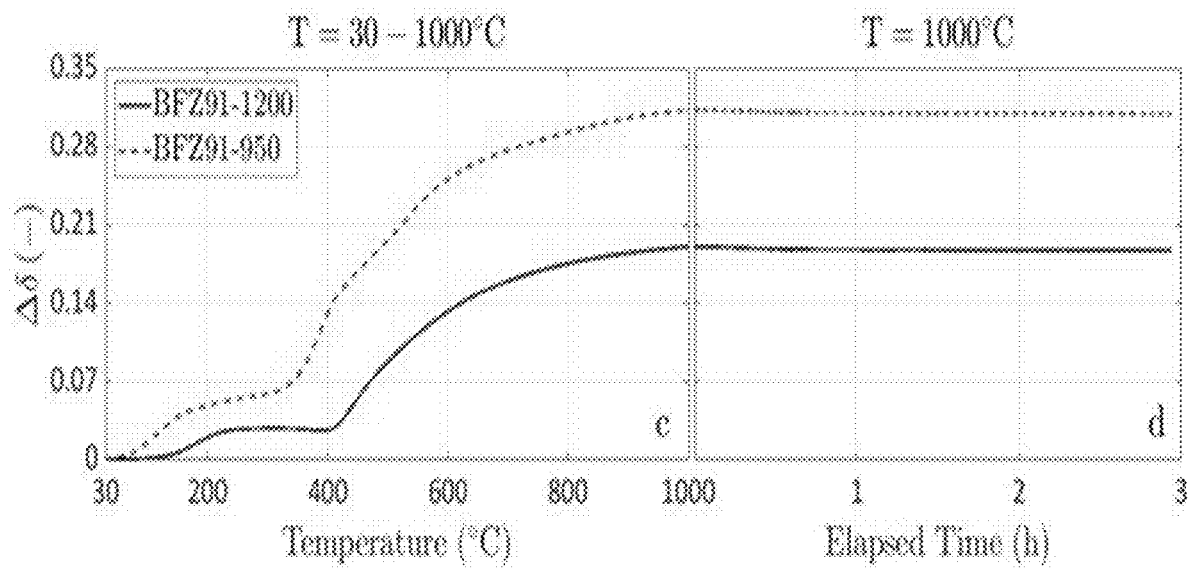
Figure 21A:
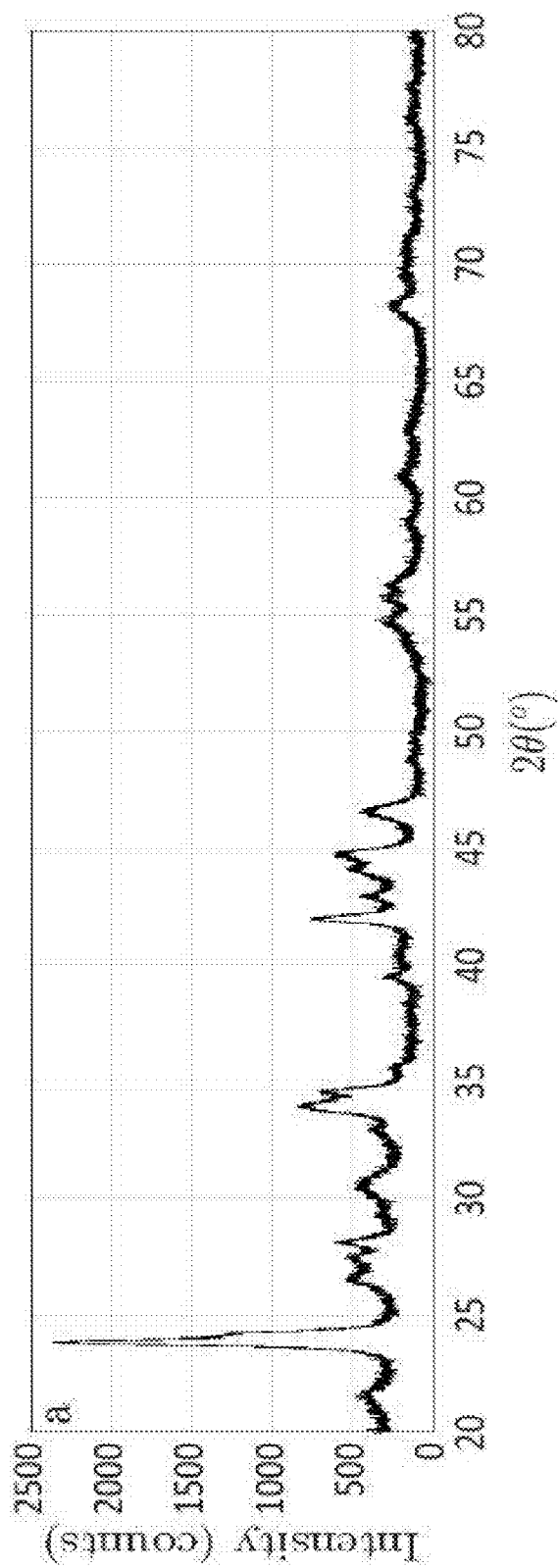
Figure 21B:
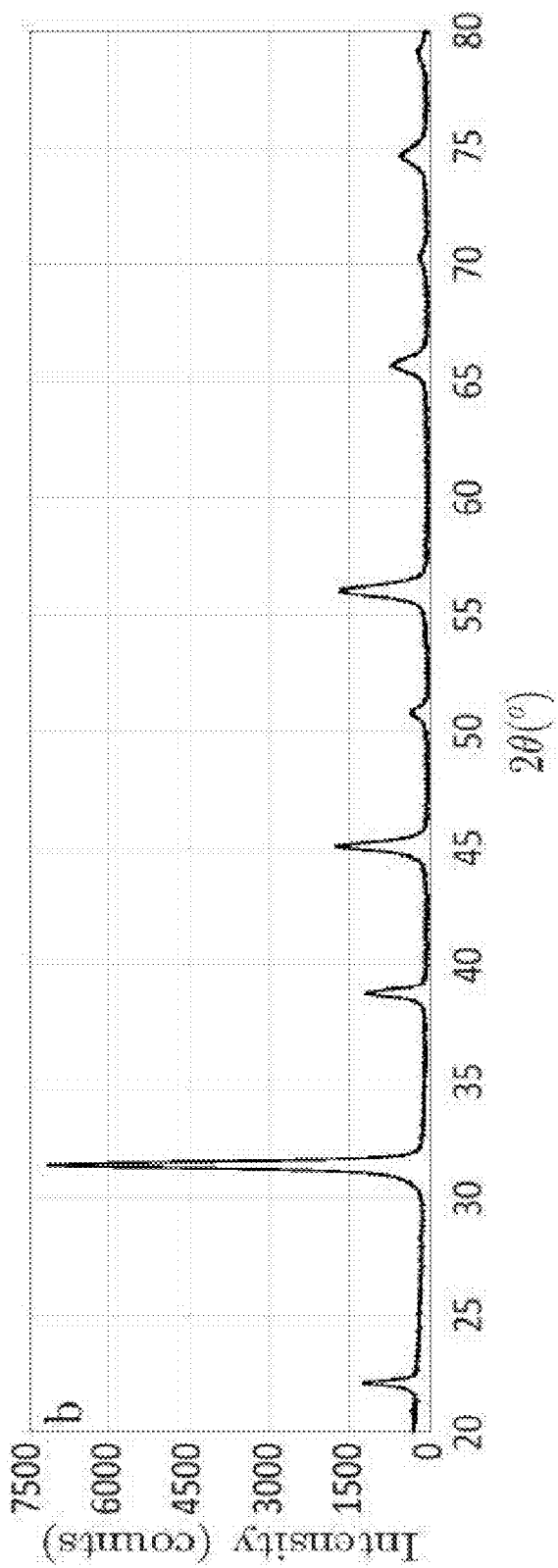

1. Characterization of the As-Prepared BFZ91 Powder and Pellet. It is known that the $BaFeO_{3-\delta}$ parent perovskite exhibits a hexagonal crystal structure at room temperature, but the structure changes to triclinic at 700° C. and then to cubic at 900° C. when exposed to air. (See refs. 65-67) High $J_{O2}$ is achieved at temperatures exceeding 750° C., that is, when $BaFeO_{3-\delta}$ obtains a triclinic or cubic phase. (See refs. 66-67) Given that phase transitions during heating and cooling could lead to mechanical failure of the dense membrane because of volume changes, phase stabilization is required by appropriate doping. The addition of 2-10% of Zr in the B-site of $BaFeO_{3-\delta}$ can eliminate the aforementioned phase transition, giving rise to a cubic crystal structure at room temperature. (See ref. 65) When the Zr doping increases to 15%, secondary phases appear demonstrating that the solubility limit of Zr in $BaFeO_{3-\delta}$ is less than 15%. (See ref. 65) FIGS. 21A-21B show the XRD patterns of the BFZ91 powder before and after calcination at high temperature; the latter is also shown in FIG. 3A. The XRD pattern of the uncalcined powder (i.e., raw ash) is composed of several peaks that correspond to the intermediate phases of the solid solution. Calcination in ambient air at 950° C. for 4 h activates cation diffusion and leads to the formation of a phase pure perovskite oxide. The calcined BFZ91 powder exhibits a cubic crystal structure in the $Pm\bar{3}m$ space group without any secondary phases. The diffraction pattern agrees with that of $BaFe_{0.95}Zr_{0.05}O_{2.56}$ (ICDD 04-022-8935) (see ref. 68) and is in agreement with a previous work on Zr-doped $BaFeO_{3-\delta}$ oxides. (See refs. 57, 65-67) High-temperature XRD measurements for BFZ91 in ambient air have also shown that the cubic structure is preserved up to 950° C. (See ref. 57) The surface area of the calcined BFZ91 powder was estimated at 4.0±0.3 m²/g using BET.

FIGS. 3A-3D compare the XRD pattern of the calcined BFZ91 powder with that of the sintered BFZ91 pellet prior to any polishing. As expected, the crystallization of the BFZ91 pellet increases because of sintering at 1200° C. This is confirmed by the increase in the peak intensity and the decrease in the peak width as compared to the peaks of the calcined BFZ91 powder. The crystal structure of the BFZ91 pellet remains cubic (space group $Pm\bar{3}m$) and no secondary phases are detected. An interesting observation is that the peak positions of the sintered BFZ91 pellet shift to lower 2θ angles when compared to the peak positions of the calcined BFZ91 powder. This is highlighted in FIGS. 3B and 3D (subplots, which zoom into the 2θ range of 29-33°. This peak shift toward lower 2θ angles implies a unit cell lattice expansion for the sintered BFZ91 pellet compared to the unit cell of the calcined BFZ91 powder. Rietveld refinement was used to estimate the lattice constant of each pattern, and the results are shown in Table 1, confirming the aforementioned lattice expansion of the BFZ91 pellet (a=b=c=4.079 Å) compared to that of the BFZ91 powder (a=b=c=4.022 Å).

Interestingly, the oxygen content of the BFZ91 powder and pellet estimated based on the Rietveld refinement is different (Table 1). Although iodometric titration is a more accurate method to evaluate the oxygen deficiency (δ) of each material (see ref. 68), the fact that less oxygen is estimated in the structure of the BFZ91 pellet suggests that the source of the lattice expansion of the BFZ91 pellet could be related to an irreversible loss of oxygen because of sintering at 1200° C. This is consistent with the tendency of ceramic oxides to lose oxygen from their structure when the temperature is increased and as a function of $P_{O2}$. To support this hypothesis, TGA measurements were conducted with: (1) the calcined BFZ91 powder (950° C., 4 h), which will be denoted BFZ91-950, and (2) the BFZ91-950 powder recalcined at 1200° C. for 8 h, that is, using the same heat treatment employed during the sintering of a BFZ91 pellet; this powder will be denoted BFZ91-1200. For the TGA measurements, approximately 0.1 g of powder were first heated from room temperature to 150° C. for 2 h to ensure the investigated materials were dehydrated. Then, the temperature was decreased to 30° C. until mass equilibration. After this step, the TGA furnace was heated from 30 to 1000° C. using a heating rate equal to 20° C./min followed by equilibration at 1000° C. for 3 h. Ambient air at 100 sccm was flowing continuously during the measurements. The results are shown in FIGS. 4A-4D (the dehydration step is not plotted), which also includes the oxygen deficiency change (Δδ) calculated using the following equation:

$$\Delta\delta = \frac{W_{BaFe_{0.9}Zr_{0.1}O_{3-\delta}}}{W_O} \frac{\Delta m}{m_s} \quad (3)$$

In eq 3, $W_{BaFe_{0.9}Zr_{0.1}O_{3-\delta}}$ is the molar weight of the off-stoichiometric $BaFe_{0.9}Zr_{0.1}O_{3-\delta}$ material at room temperature (calculated using the stoichiometry defined in Table 1 for each sample), Δm is the change in the sample's mass during the TGA measurement, $m_s$ is the sample's starting mass, and $W_O$ is the atomic weight of oxygen. FIGS. 4A-4D indeed show that the oxygen loss is different in the studied powders throughout the entire heating step with BFZ91-950 losing more oxygen compared BFZ91-1200. As a result, $\Delta\delta$ is higher for BFZ91-950 compared to BFZ91-1200. Note that the calculated $\Delta\delta$ values, as shown in FIGS. 4A-4D, are in agreement with TGA measurements conducted in air for $BaFe_{0.95}Zr_{0.05}O_{2.56}$. (See ref. 68) In that work, however, the lattice expansion observed here was not reported. Based on the XRD and TGA results, as shown in FIGS. 3A-3D and 4A-4D, respectively, the lattice expansion of the BFZ91 pellet can be because of an irreversible increase in the content of oxygen vacancies induced by the sintering at high temperatures.

Although the XRD and TGA results shown in FIGS. 3A-3D and 4A-4D, respectively, confirm a lattice expansion induced by sintering at higher temperatures, the lattice expansion is not related only with changes in the amount of oxygen in the structure but also because of changes in the amount of the iron (Fe) charged species within the material. To further elaborate on this, the following point defect chemistry model for BFZ91 was postulated written using the Kroger-Vink notation (see ref. 28, 29, 58):

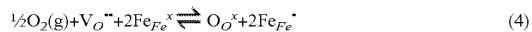
$$\tfrac{1}{2}O_2(g)+V_O^{\cdot\cdot}+2Fe_{Fe}^x \rightleftharpoons O_O^x+2Fe_{Fe}^{\cdot} \qquad (4)$$

$$2Fe_{Fe}^x \rightleftharpoons Fe_{Fe}^{\cdot}+Fe'_{Fe} \qquad (5)$$

Reaction 4 reflects the $O_2$ incorporation into the material while reaction 5 accounts for the Fe disproportionation. A similar point defect model has been proposed for other materials. (See ref. 28, 29, 58, 69, 70) In reactions 4 and 5, $V_O^{\cdot\cdot}$ denotes an oxygen vacancy, $O_O^x$ is an oxygen ion ($O^{2-}$) incorporated into an $O^{2-}$ lattice site while $Fe_{Fe}^{\cdot}$, $Fe_{Fe}^x$, and $Fe_{Fe}'$ correspond to $Fe^{+4}$, $Fe^{+3}$, and $Fe^{+2}$ incorporated into the $Fe^{+3}$ lattice site, respectively. $Fe_{Fe}^{\cdot}$, $Fe_{Fe}^x$, and $Fe_{Fe}'$ participate in the electron transfer required to ionize $O_2$ prior to incorporation into the material. Depending on the BFZ91 defect chemistry and thermodynamics, $O_2$ incorporation may also happen because of the following reaction, which is the combination of reactions 4 and 5 (see ref. 69, 70):

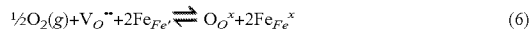
$$\tfrac{1}{2}O_2(g)+V_O^{\cdot\cdot}+2Fe_{Fe}' \rightleftharpoons O_O^x+2Fe_{Fe}^x \qquad (6)$$

The proposed point defect model allows for a deeper understanding of the observed chemical expansion phenomenon and its implications on the properties of the investigated materials. The mass loss, as shown in FIGS. 4A-4D, is because of oxygen release from the material leaving behind oxygen vacancies. According to reactions 4-6, this should be accompanied by a change in the concentration of the different Fe states ($Fe_{Fe}^{\cdot}$, $Fe_{Fe}^x$, and $Fe_{Fe}'$) dictated by the thermodynamics of reactions 4-6, the $ABO_{3-\delta}$ stoichiometry, and the conservation of charge neutrality in the bulk of the material. This means that BFZ91-950 and BFZ91-1200 have different amounts of oxygen vacancies in their structure as well as different concentrations of Fe states. Besides having an impact on the final unit cell volume (as the different Fe states are characterized by a different ionic radius), the different concentrations of the charged species are expected to affect the kinetics of reactions 4-6, and the diffusion of charged species within the material. As a result, this phenomenon becomes very important when calculating properties of materials (e.g., electronic and ionic conductivity, oxygen deficiency as a function of T and $P_{O2}$ etc.) confirming that for some materials, the heat treatment history can play a significant role in the measured properties. Obviously, an irreversible chemical expansion due to heat treatment may not be observed for other materials; but to improve consistency, material properties should be obtained using samples with the same heat treatment history as the material to be investigated in the final application.

Lastly, based on the estimated unit cell of the sintered BFZ91 pellet, the theoretical density of BFZ91 is calculated as $\rho_{BFZ91}^{theoretical}=5.845$ g/cm$^3$ and agrees with other studies. (See ref. 64) The true density of the sintered BFZ91 pellets (estimated using the Archimedes principle) was equal to $\rho_{BFZ91}^{true}\approx 5.840$ g/cm$^3$, which corresponds to a 99.9% relative density, demonstrating that fully dense BFZ91 membranes were successfully fabricated in this work.

2. Characterization of the As-Received $La_2O_3$ Powder. Commercial $La_2O_3$ powder was used as the OCM catalyst. The $La_2O_3$ powder was used in OCM experiments as-received, that is, without any additional treatment. The surface area of the as-received $La_2O_3$ powder estimated using BET was $3.0\pm0.7$ m$^2$/g.

Figure 5A:
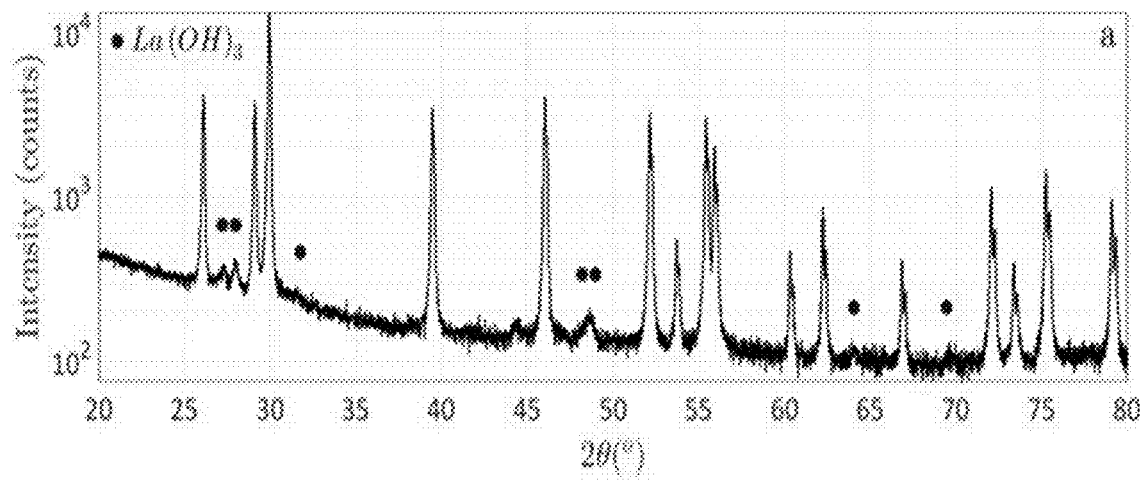

To investigate the crystal structure of the as-received $La_2O_3$ powder, XRD is conducted, and FIG. 5A shows the corresponding pattern. Interestingly, the as-received $La_2O_3$ powder is not phase pure. Although the main peaks can be assigned to the hexagonal $La_2O_3$ phase (ICDD 04-005-4229), there are 7 additional peaks at $2\theta$ angles equal to 27.3, 28.0, 31.6, 48.2, 48.6, 64.0, and 69.5°. All 7 peaks match very well with the high intensity peaks of the hexagonal lanthanum hydroxide ($La(OH)_3$) phase (ICDD 04-016-2506). Using Rietveld refinement, it was estimated that the secondary $La(OH)_3$ phase corresponds to 2.7% of the powder with the remaining being $La_2O_3$. The crystal structure data are reported in Table 1.

Although the amount of the secondary $La(OH)_3$ phase is low, it is worth understanding its origin as well as its potential decomposition at higher temperatures because the presence of this phase could potentially affect the OCM activity of the catalyst. The source of $La(OH)_3$ can be the hydroxylation of $La_2O_3$ with $H_2O$ from ambient air as this reaction has been shown to occur at room temperature. (See ref. 71) In the presence of an inert gas, $La(OH)_3$ decomposes to lanthanum hydroxide oxide (LaOOH) and then to $La_2O_3$ through the following two-step mechanism (see ref. 72):

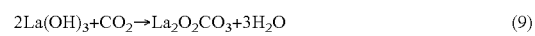
$$La(OH)_3 \rightarrow LaOOH+H_2O \qquad (7)$$

$$2LaOOH \rightarrow La_2O_3+H_2O \qquad (8)$$

Kinetically, the formation of LaOOH through reaction 7 happens at T=330° C. while full dehydration to $La_2O_3$ via reaction 8 takes place at T=490° C. (see ref. 72). At T=550° C., XRD results show that pure $La_2O_3$ is obtained (see ref. 72). However, the aforementioned decomposition mechanism changes in the presence of $CO_2$ given that lanthanum is a basic element, and hence, its oxides and hydroxides can easily form lanthanum dioxycarbonate ($La_2O_2CO_3$) or other carbonate species. The decomposition of $La(OH)_3$ in ambient air proceeds through the following mechanism (see refs. 73-74):

$$2La(OH)_3+CO_2 \rightarrow La_2O_2CO_3+3H_2O \qquad (9)$$

$$La_2O_2CO_3 \rightarrow La_2O_3+CO_2 \qquad (10)$$

Figure 5B:
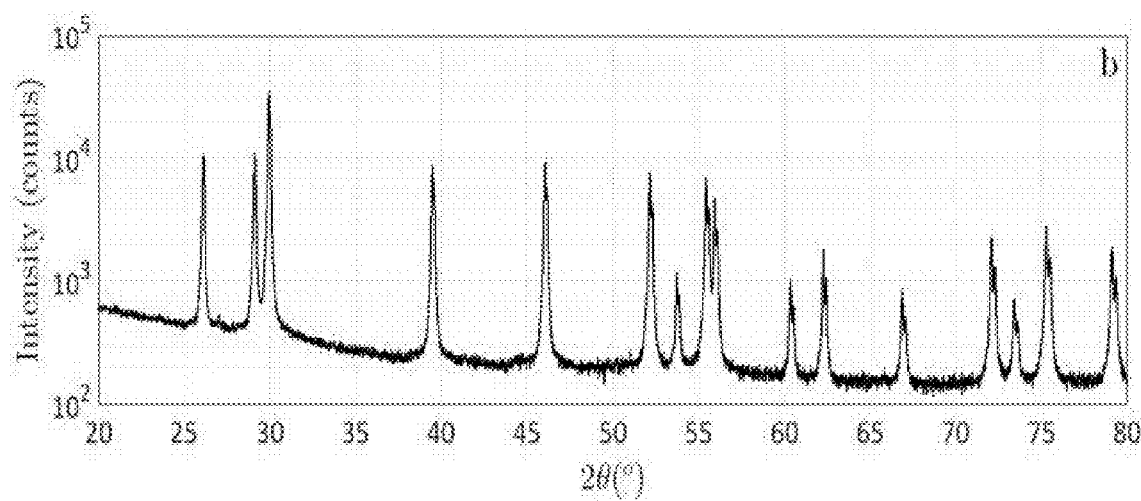
Figure 6A:
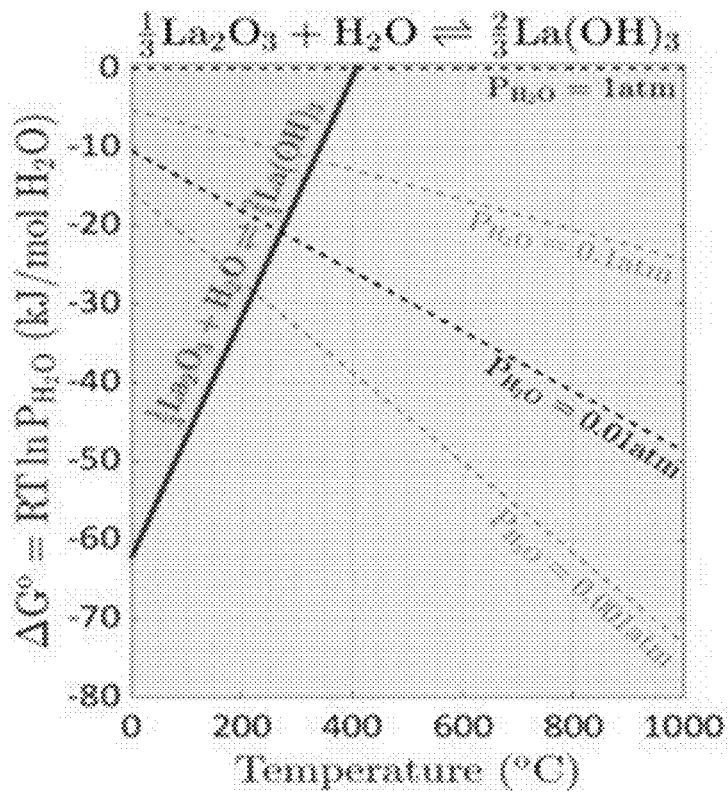
FIGS. 6A-6B depict Ellingham diagrams showing the stability of $La(OH)_3$ (FIG. 6A) and $La_2O_2CO_3$ (FIG. 6B) as a function of T and $P_{H2O}$ or $P_{CO2}$ (for absolute pressure of 1 atm). The light pink zone denotes the area of $La(OH)_3$ and $La_2O_2CO_3$ formation, while the light blue zone denotes the area of $La_2O_3$ formation. The red solid line denotes the standard-state Gibbs free energy change of the corresponding reaction ($\Delta G° = \Delta H° - T\Delta S°$). The dashed lines correspond to the standard-state Gibbs free energy change as a function of T for a fixed partial pressure ($\Delta G° = RT \ln P_{H2O}$ or $\Delta G° = RT \ln P_{CO2}$). Standard-state molar enthalpies of formation and standard-state molar entropies for each species were obtained from reference tables. (See refs. 77, 79-81).
Figure 6B:
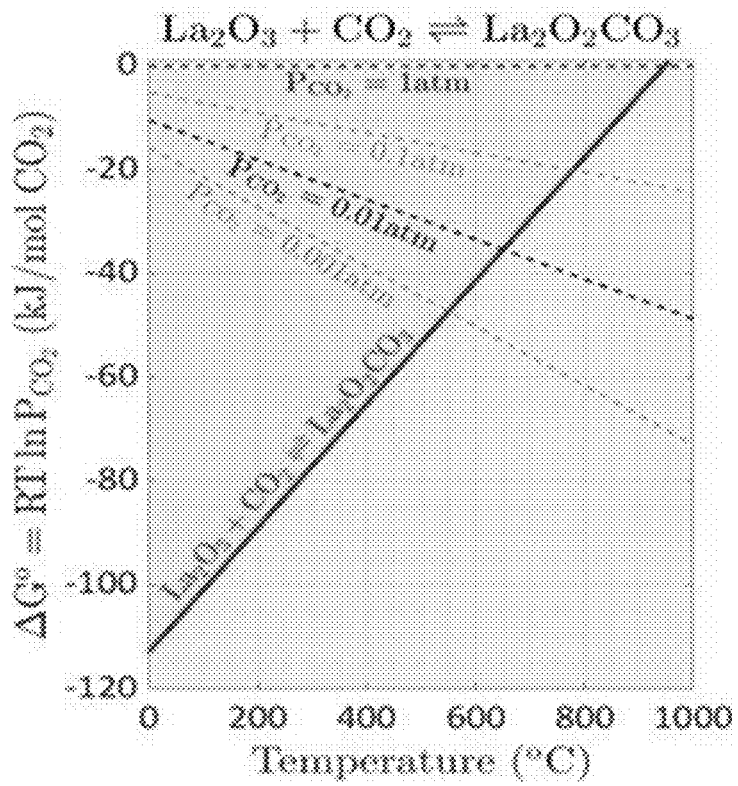

Reaction 9 takes place between T=200-600° C., while reaction 10 happens at high rates in the interval T=650-800° C. (See ref. 73) XRD results reported in the literature confirm the presence of $La_2O_2CO_3$ at 500-700° C. during the process of $La(OH)_3$ decomposition in air (see ref. 73, 75), while pure $La_2O_3$ is observed at 800° C. (See ref. 75) This is consistent with additional data showing that reaction 10 is triggered at T=700-725° C. (See refs. 76-78) To further confirm the aforementioned literature results, the as-received $La_2O_3$ powder was heat treated in ambient air at 800° C. for 2 h. As shown in FIG. 5B, XRD results obtained immediately after this heat treatment confirm that a pure phase $La_2O_3$ material can be obtained without any additional $La(OH)_3$ or $La_2O_2CO_3$ phases. To facilitate the discussion in the following sections, FIGS. 6A-6B show the stability of $La(OH)_3$ and $La_2O_2CO_3$ as a function of T and $P_{H2O}$ or $P_{CO2}$. Regarding the T at which decomposition to $La_2O_3$ occurs for a fixed partial pressure, the differences between the results in FIGS. 6A-6B and the literature results presented earlier are because the former provide information from a purely thermodynamic point of view while the latter are based on TGA measurements for which the kinetics of the reactions are also considered.

Based on the aforementioned discussion, the following important conclusions are drawn. First, although the as-received $La_2O_3$ powder contains a small amount of $La(OH)_3$, the latter decomposes to pure $La_2O_3$ during the initial heating of the button-cell reactor in pure Ar from room temperature to 1025° C. (see 2.3 and FIGS. 6A-6B). After sealing is completed, the reactor temperature decreases to T=750° C. while pure Ar is still flowing on the $CH_4$ side. OCM experiments begin at T=750° C. or T=850° C., and hence, the starting OCM catalyst is expected to be pure $La_2O_3$ without any secondary phases. This is consistent with a previous work on undoped and Sr-doped $La_2O_3$ where pretreatment in pure $N_2$ at 800° C. was conducted prior to OCM experiments to remove such impurities. (See ref. 60). Second, although it is thermodynamically favorable for lanthanum hydroxides and carbonates to decompose at T>725° C., this happens in the presence of air or an inert gas. As shown in FIGS. 6A-6B, at a fixed T, the partial pressure of $H_2O$ and $CO_2$ can alter the tendency toward the formation of lanthanum hydroxides or carbonates. Under OCM conditions, the gaseous environment will include species such as $CH_4$, $O_2$, $H_2O$, $CO_2$, $C_2$ and so forth. Depending on their concentrations, new lanthanum-based phases may appear, which could have beneficial or deleterious effects on the $C_2$ production. For example, $La_2O_2CO_3$ rods have been shown to be active for OCM at low temperatures (420-500° C.) when prepared using a hydrothermal method but low OCM activity was observed for $La_2O_2CO_3$ plates synthesized via a precipitation method. (See ref. 78) The thermodynamics of the aforementioned lanthanum-containing species create another challenge regarding the characterization of the used $La_2O_3$ catalyst. After the end of the OCM measurements, cooling down the reactor from T>750° C. to room temperature can happen in two ways: (1) by flowing pure Ar in the $CH_4$ side of the reactor and (2) by flowing $CH_4$—Ar mixtures. In the first scenario, if lanthanum hydroxides or carbonates form on $La_2O_3$ during OCM (because of exposure to a hydrocarbon environment), cooling down the reactor in pure Ar will lead to their decomposition, and hence, these phases may not be detected by common characterization methods such as XRD although they may still form under the OCM conditions reported in this work. If the second option is employed, then, as will be shown in the next section, species such as $H_2O$ or $CO_2$ will still form through $CH_4$ full oxidation because of the finite $O_2$ permeation through the membrane. These will react with $La_2O_3$ at T<725° C. forming lanthanum hydroxides or carbonates. These phases may be detected by XRD, but they will correspond to phases formed during the cooling of the reactor rather than under the OCM conditions of this work. Cooling down the reactor by flowing an inert gas in the feed side (instead of air) could solve the aforementioned problem, but then, the presence of $CH_4$ in the stream will decompose the BFZ91 membrane. In this work, it was chosen to cool down the reactor using ambient air in the air side and 5% $CH_4$ (balanced with Ar) in the $CH_4$ side in order to preserve the structure of the BFZ91 membrane and reduce the impact of $CH_4$ and its gaseous products on the final $La_2O_3$ crystal structure.

As a final remark, note that the aforementioned challenge demonstrates once again the implications of properly characterizing OCM catalysts with ex situ techniques and highlights the importance of using in situ catalyst characterization methods. Similar conclusions have been drawn for $La_2O_3$ investigated ex situ using X-ray photoelectron spectroscopy after OCM measurements. (See ref. 82)

3. $CH_4$ Conversion Using BFZ91 in the Absence of a Catalyst. To determine the species produced by the reaction of $CH_4$ with $O_2$ that permeates through BFZ91 and to identify any catalytic reactions taking place on BFZ91, experiments conducted in the absence of a catalyst on the $CH_4$ side of BFZ91 were analyzed. These reference measurements are taken in the range T=800-900° C. and $X^{in}_{CH4}$=0-30%.

FIG. 7A shows that at T=800° C., $J_{O2} \approx 0.75$ (μmol/cm²/s), and it is almost constant in the range $X^{in}_{CH4}$=0-30%. However, at T=850° C. and T=900° C., $J_{O2}$ rises as more $CH_4$ is added into the stream. This dependency is related to the rate-limiting step of the $O_2$ permeation mechanism. (See refs. 28-31) It is known that in CMRs, $J_{O2}$ is limited by surface reactions on either gas-membrane interface or by bulk diffusion. In the presence of a fuel, its reaction with $O_2$ from the membrane can increase $J_{O2}$ if surface reactions on the fuel side are not rate limiting. This is because of a decrease in the fuel side $\mu_{O2}$ leading to an overall increase in the $\mu_{O2}$ gradient between the two membrane sides. (See refs. 29, 64, 83, 84) Previous work has shown that BFZ91 exhibits thickness limitations, and hence, higher $J_{O2}$ can be achieved using thinner membranes. (See ref. 67) However, for a fixed thickness, BFZ91 also shows limitations on the $CH_4$ side gas-membrane interface. (See ref. 57, 58) The results in FIG. 7A suggest that at T=800° C., the $CH_4$ side surface reaction is limiting $J_{O2}$ in addition to the bulk diffusion resistance. As T rises, surface reactions are accelerated, and hence, the addition of $CH_4$ increases $J_{O2}$ when compared to the nonreactive case. This effect is more pronounced at 850 and 900° C.

Figures 22I, 22J, 22K, 22L, 22M, 22N, 22O, 22P:
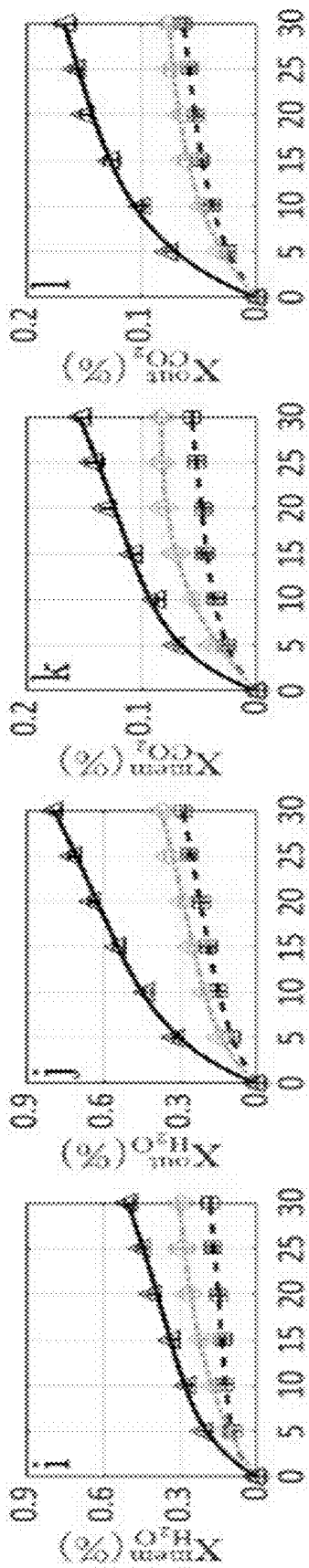

As shown in FIGS. 7C and 7D, at T=800° C., $C_{CH4}$<2% while $C_{O2}$<8%. At higher T and for the same $X^{in}_{CH4}$, both $C_{CH4}$ and $C_{O2}$ increase, consistent with enhanced reactivity at elevated T. However, for the same T, $C_{CH4}$ decreases as more $CH_4$ is added into the stream; $C_{O2}$ increases but does not reach 100%, a sign that under the conditions investigated herein, $CH_4$ cannot fully convert all the available $O_2$ into products in the presence of BFZ91. In addition, FIG. 7B and FIGS. 22A-22P show that for all cases, the $CH_4$ side $X_{O2}^{mem}$ and $X_{O2}^{out}$ are high, further confirming that $CH_4$ does not react with $O_O^x$ or gaseous $O_2$ at considerable rates (especially at lower T) and that a low $P_{O2}$ environment cannot be established when using BFZ91 alone. According to FIGS. 22A-22P, some fraction of the fuel succeeds to react with lattice oxygen on the BFZ91 surface or with molecular $O_2$ in the gas phase, as demonstrated by the non-zero mole fraction of $C_2H_6$, $C_2H_4$, $H_2O$, $CO_2$, $H_2$, and CO. The production of these species, however, is low, as confirmed by the low yields shown in FIGS. 7E-7H and in FIGS. 23A-23L. For comparison, the results of the same experiment in the presence of $La_2O_3$ (shown later in Section 5) reveal negligible $O_2$ near the $CH_4$ side of the membrane, $C_{O2} \approx 100\%$ and higher $C_2$ yields.

The aforementioned results lead us to the following important conclusions. First, it appears that the BFZ91 membrane does not have a strong catalytic activity toward the decomposition or oxidation of $CH_4$. This is a notable property of the BFZ91 membrane, which is expected to increase the $C_2$ yields by avoiding side reactions of $CH_4$ producing species other than $C_2H_6$ and $C_2H_4$. Second, according to FIGS. 7E and 7G and FIGS. 23A-23L, some activity toward the production of $C_2$ is observed. For example, $S_{C2H6}$ is between 30-50% while that of $S_{C2H4}$ is around 10-30%. However, the corresponding yields are below 2%. Although a $C_2$ yield of ~3% can be obtained at 900° C., the use of an OCM-active catalyst is expected to promote $C_2$ production at lower T. The same results confirm that overall, the role of the BFZ91 membrane is to supply $O_2$ from the air side without a significant participation in the conversion of $CH_4$. Third, according to FIGS. 22A-22P, the mixture composition near the membrane surface can be different compared to that at the outlet of the reactor. In addition to gaseous diffusion, gas phase chemistry can alter the mixture composition along the hot zone of the reactor when using a fuel. Hence, measuring the concentration of species near the membrane surface in addition to the outlet of the reactor is required to understand the effect of gas phase reactions, and the impact of the membrane and catalyst on the fuel conversion.

Figure 24:
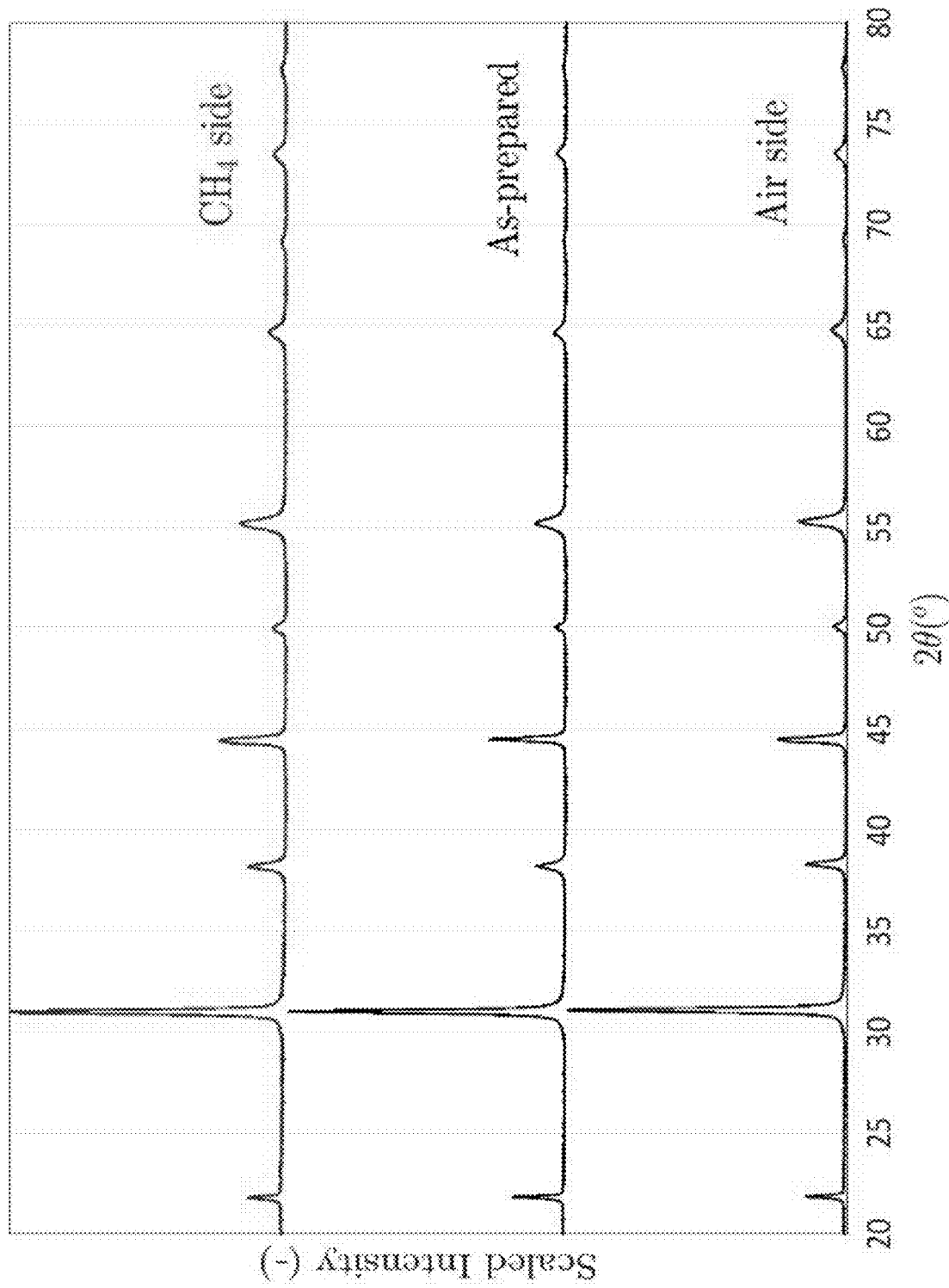
FIG. 24 depicts XRD patterns of the as-prepared and used BFZ91 membrane after the end of the OCM measurement in the absence of a $La_2O_3$ catalyst.

Each experimental point, as shown in FIGS. 7A-7H, is recorded after a stabilization period of approximately 1 day. No loss of activity was observed for the entire duration of the experiment. This is confirmed by the XRD results, as shown in FIG. 24. No secondary phases are observed in the XRD patterns of the BFZ91 membrane on both sides. The stability of BFZ91 is associated with the doping of Zr in the B-site of the perovskite which has been shown to improve the resistance to decomposition and the formation of carbonates when the material is exposed to a mixture of hydrocarbons. (See refs. 33, 57, 58, 85) Regarding the stability of BFZ91 in a $CO_2$- containing environment, Balachandran et al. have already conducted studies using $CO_2$ mole fractions of 50 and 75% in the stream. (See ref. 86) Although long-term studies were not reported, the obtained $J_{O2}$ was higher than LSCF membranes operating under the same conditions. (See ref. 86) Because the formation of $BaCO_3$ is favorable at high T and $CO_2$, one would expect that any irreversible membrane deactivation at such conditions would have been immediate and would have lowered $J_{O2}$ significantly. However, more detailed studies (outside the scope of this work) are required to understand the high resistance of BFZ91 against $BaCO_3$ formation.

4. Performance and Stability of BFZ91 and $La_2O_3$ under Long-Term OCM Measurements. To evaluate the OCM performance of BFZ91 with $La_2O_3$, long-term measurements between T=750-900° C. and $X^{in}_{CH4}$=0-30% were conducted. During the experiment, the temperature was fixed and $X^{in}_{CH4}$ increased to a specified value. Measurements were obtained every 1 h until the performance reached steady state. Once steady state was achieved, $X^{in}_{CH4}$ increased again and the process was repeated. When the measurement at $X^{in}_{CH4}$=30% was completed, $CH_4$ was removed progressively and the temperature of the reactor increased to the next interval by flowing pure Ar in the $CH_4$ side. According to FIGS. 6A-6B and the discussion in Section 3.2, this means that thermodynamically, the starting catalyst at each temperature was pure $La_2O_3$. Measurements were repeated in the same sequence for all the temperatures investigated here. The long-term measurements lasted for approximately 23 days after which the experiment was stopped. Note that FIGS. 8A-8B only shows the reactive measurements; no stability was measured for $X^{in}_{CH4}$=0%.

FIGS. 8A-8B show $J_{O2}$ and the activities of $C_2H_6$, $C_2H_4$, and $C_2$ ($C_2H_6$, $C_2H_4$, and acetylene ($C_2H_2$)) as a function of time, which clearly demonstrate the high stability of BFZ91 and $La_2O_3$ towards $C_2$ production. During the entire 23-day experiment, $J_{O2}$ and $\dot{n}^{out}_{C2}$ were stable without any loss of performance. This is the first time that such long-term OCM measurements are demonstrated with stable membrane-catalyst materials that have been subjected to temperature and fuel cycling for long times. At 850 and 900° C., $J_{O2}$ shows a gradual increase as a function of time for the same $X^{in}_{CH4}$ value, while the activities of the $C_2$ species remain constant. This gradual $J_{O2}$ increase results from the progressive increase of $X^{out}_{CO2}$ and $X^{out}_{H2O}$ as a function of time.

Figures 9A, 9B:
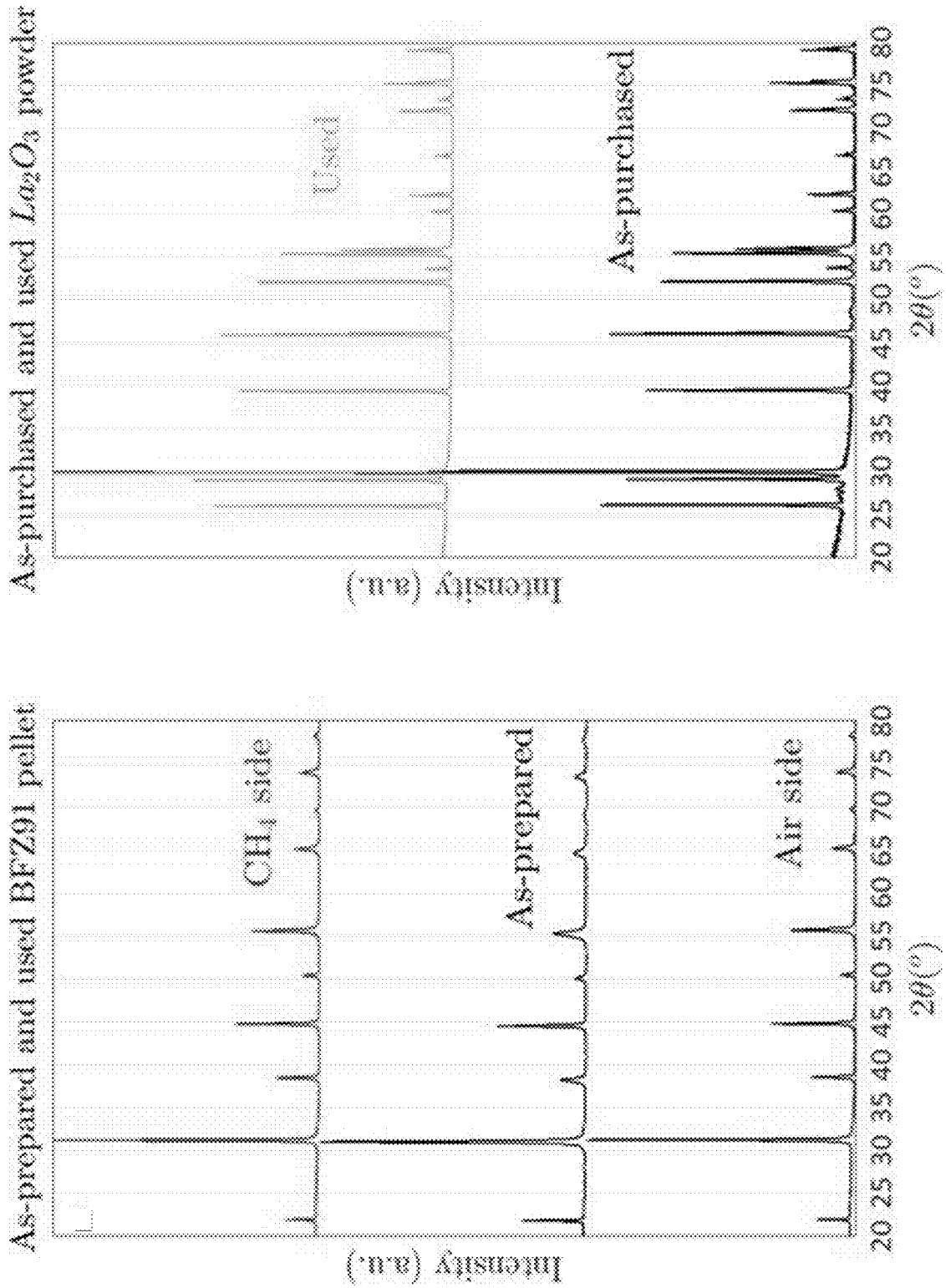

FIGS. 9A-9B show the XRD patterns of the unused and used BFZ91 and $La_2O_3$. According to FIGS. 9A-9B, no phase transformations or secondary phases were detected on the air and $CH_4$ side of the BFZ91 membrane after the end of the OCM measurements. The same is true for the used $La_2O_3$ powder. For $La_2O_3$, one cannot draw a safe conclusion about the formation of stable lanthanum hydroxides and carbonates during OCM based on ex situ XRD; however, recent in operando Raman spectroscopy studies demonstrated the high stability of $La_2O_3$ under industrially relevant OCM conditions. (See ref. 62) Nevertheless, the fact that ex situ XRD reveals the absence of secondary phases on $La_2O_3$ is consistent with the Ellingham diagrams of FIGS. 6A-6B and the mole fractions of $H_2O$ and $CO_2$ formed near the membrane surface (FIGS. 13A-13H and 14A-14H discussed later in Section 3.6). Although the aforementioned results may confirm the high structural stability of the BFZ91 membrane in a hydrocarbon environment and its compatibility with $La_2O_3$, they do not account for the possible formation of amorphous phases on the membrane or the $La_2O_3$ catalyst. Such amorphous phases, if present, could degrade the performance under longer trials. Indeed, Schucker et al. have proposed that amorphous phases of $SrCO_3$, SrO, and $SrO_2$ may exist on Sr-doped $La_2O_3$ under OCM conditions. (See ref. 62) In that work, the authors confirm that such amorphous phases cannot be detected by XRD or Raman spectroscopy. However, the study of Schucker et al. does not provide long-term measurements to verify a performance loss as a function of time that could be ascribed to the aforementioned phases. (See ref. 62) In this work, considering that the 23-day measurement is by itself a long term trial allows us to conclude that amorphous phases, if present on the materials, do not degrade the OCM performance.

FIGS. 10A-10F present the microstructure of the BFZ91 pellet and $La_2O_3$ powder before and after the OCM measurements. The as-sintered BFZ91 pellet (FIG. 10A) shows a large distribution of grain boundary sizes, which range between 0.5-5 μm. No signs of porosity are observed, which confirm the high relative density of the pellet estimated using the Archimedes principle. FIG. 10B shows one of the sides of the BFZ91 pellet after polishing. A flat surface is observed with some lines that correspond to scratches from the polishing procedure. Some material expulsion is also noticed despite the fact that a high grit number sandpaper was used to ensure a polished finish. FIGS. 10C-10D show the air and $CH_4$ side of the BFZ91 pellet, respectively, after the end of the OCM measurements with $La_2O_3$. On both sides, surface terraces have become visible within some of the grains, which is probably related to the grain crystallographic orientation and the polishing process as no such terraces are observed in FIG. 10A. Similar observations have been reported for other materials (see refs. 87, 88). No particle-like structures are found on either side of the BFZ91 pellet, consistent with the XRD results of FIGS. 9A-9B. The microstructure of the BFZ91 pellet after the end of the measurements without $La_2O_3$ is similar to the one shown in FIGS. 10C and 10D. Finally, FIGS. 10E and 10F present the as-purchased and used $La_2O_3$ powder, respectively. The used powder shows significant sintering because of the high T operation. As shown in FIGS. 25A-25B comparing the $La_2O_3$ catalyst after the end of the OCM measurements and after calcination of a fresh catalyst at T=1025° C. for 24 h, the sintering of the $La_2O_3$ powder observed, as shown in FIG. 10F, is primarily related to the sealing procedure followed in this work and not because of operation in a reactive environment. This also confirms that the sintering of the $La_2O_3$ catalyst happened before the beginning of the OCM measurements. If this step could be avoided, then, the sintering of the $La_2O_3$ powder would be lower given that the maximum T investigated in this work is 900° C.

Finally, based on the XRD and SEM results, as shown in FIGS. 9A-9B and 10A-10F, no signs of carbon deposition are observed on the used materials. In addition, if carbon forms in the products, the presence of $H_2O$ and $CO_2$ in the mixture at mole fractions between 0.5-2.5 and 0.2-0.9%, respectively (as shown in FIGS. 13A-13H and 14A-14H), would have led to its conversion to $H_2$ and CO given that the steam gasification of carbon to syngas and the reverse Boudouard are thermodynamically favorable under the conditions investigated in the measurements (T>700° C.).

5. Analysis of BFZ91 and $La_2O_3$ Steady-State OCM Measurements. At each T and $X^{in}_{CH4}$, as shown in FIGS. 8A-8B, detailed measurements were obtained after steady state was achieved to shed light into the performance and OCM chemistry. FIGS. 11A-11H, 12A-12H, 13A-13H, and 14A-14H present these results.

FIG. 11A shows $J_{O2}$ as a function of T and $X^{in}_{CH4}$. At T=750° C., $J_{O2}$ is constant at ~0.5 μmol/cm$^2$/s and independent of $X^{in}_{CH4}$. However, as T increases, $J_{O2}$ rises as a function of $X^{in}_{CH4}$. As discussed earlier, this is related to the rate-limiting steps of the $O_2$ permeation process. Surface reactions on the $CH_4$ side are rate limiting at T≤800° C. (in addition to bulk diffusion), and they are accelerated at T≥850° C. The $J_{O2}$ increase as a function of $X^{in}_{CH4}$ at T=850-900° C., as shown in FIG. 11A, suggests that a low $P_{O2}$ is developed in the presence of $La_2O_3$ when $CH_4$ is added. This will be confirmed in the results that follow.

In addition to the above, one can also make a note about the nonreactive $J_{O2}$ measurements ($X^{in}_{CH4}$=0%) at 800-900° C., as shown in FIG. 11A. At this temperature range, comparison with FIG. 7A reveals that $J_{O2}$ has decreased slightly in the presence of $La_2O_3$. Given that the thickness of the BFZ91 membrane was almost the same for both experiments, the slight decrease in the nonreactive $J_{O2}$ could be related to the presence of the $La_2O_3$ powder on the $CH_4$ side of the membrane. $La_2O_3$ could restrict gaseous diffusion through its porous structure thus decreasing $J_{O2}$ In any case, the performance drop observed in the measurements was not remarkable, and hence, if the slight drop in $J_{O2}$ is not related to experimental uncertainties but is because of the presence of $La_2O_3$, the latter does not significantly impact $J_{O2}$, especially when $CH_4$ is added in the reactor.

FIG. 11B shows $C_{CH4}$ as a function of T and $X^{in}_{CH4}$. Higher $C_{CH4}$ is achieved as T increases given the Arrhenius activated behavior of gas phase and surface (membrane and catalyst) reactions. At the same T, adding more fuel decreases $C_{CH4}$ showing that less fraction of $CH_4$ can be converted to products. FIGS. 11C and 11D shows $S_{C2H6}$ and $S_{C2H4}$, respectively. The system is less selective to the formation of $C_2H_6$ as T increases. The trend is opposite for $C_2H_4$, whose selectivity increases as a function of T except at 900° C. At the same T, adding more $CH_4$ increases the selectivity with the exception of $S_{C2H6}$ at 900° C. and of $S_{C2H4}$ at 750° C., where nearly constant values are observed. These trends can be explained by the conversion of $C_2H_6$ to $C_2H_4$, which, in general, can happen in the gas phase and on the $La_2O_3$ catalyst through oxidative and non-oxidative pathways.

To obtain further insights about the aforementioned reactions, the NODHE in the absence and presence of $La_2O_3$ between T=750-900° C. was examined. FIGS. 27A-27F show that at equilibrium, $C_2H_6$ is fully converted to products even at T=750° C. The mole fraction of $C_2H_4$ is finite but low and the system favors the production of $CH_4$, $H_2$, and $C_2H_2$. Under non-equilibrium conditions, FIGS. 27A-27F show identical $C_2H_6$ thermal decomposition with and without $La_2O_3$. As a result, one can safely conclude that $La_2O_3$ is not active toward the $C_2H_6$ and $C_2H_4$ non-oxidative dehydrogenation, which can only happen in the gas phase. FIGS. 27A-27F reveal that the conversion of $C_2H_6$ at T=750° C. approaches while full conversion to products is achieved at T=850° C. Most of $C_2H_6$ is converted to $C_2H_4$ and $H_2$ with $C_2H_2$ and $CH_4$ also being present but at lower mole fractions. The produced $C_2H_4$ peaks at T≈780° C., and then, it decreases because of decomposition to $C_2H_2$, $CH_4$, and $H_2$. These results confirm the presence of both $C_2H_6$ and $C_2H_4$ non-oxidative dehydrogenation in the gas-phase, which depend on the residence time and become more intense as the temperature rises. Hence, it was demonstrated that one pathway for $C_2H_4$ production is the NODHE in the gas phase; this reaction does not proceed on $La_2O_3$. The possibility of the oxidative dehydrogenation of $C_2H_6$ (ODHE) to $C_2H_4$ and $H_2O$ (either in the gas phase or on $La_2O_3$) will be discussed later.

The yields (FIGS. 11E and 11F) and activities (FIGS. 11G and 11H) of $C_2H_6$ and $C_2H_4$ show similar trends. For the same $X^{in}_{CH4}$, $Y_{C2H6}$ and $\tilde{n}_{C2H6}$ increase at 800° C. compared to 750° C., but a sharp drop is observed at 850° C. and 900° C. because of $C_2H_6$ conversion to $C_2H_4$. In contrast, $Y_{C2H4}$ and $\tilde{n}_{C2H4}$ clearly increase as T rises. However, the increase at 900° C. compared to the 850° C. case is small, confirming that $C_2H_4$ either pyrolyzes at high T similar to $C_2H_6$ (see FIGS. 27A-27F) or reacts with other products. At the same T, $Y_{C2H6}$ and $Y_{C2H4}$ drop as a function of $X^{in}_{CH4}$, a sign that the formation of the desired products is limited by the insufficient amount of $O_2$ through the membrane that has already been fully converted to products ($C_{O2}$≈100%, see FIG. 13B). However, at the same T, both $\tilde{n}_{C2H6}$ and $\tilde{n}_{C2H4}$ increase as more fuel is introduced in the $CH_4$ side, which is consistent with the known trend of higher $C_2$ selectivity under fuel-rich conditions.

FIGS. 12A-12H show the selectivities and yields of the rest of the species produced within the reactor. FIGS. 12A-12D demonstrate that the $La_2O_3$ catalyst is selective toward the formation of $H_2O$ and $CO_2$ with yields higher than those of $C_2H_6$ and $C_2H_4$. This suggests that, in addition to $CH_4$ coupling to $C_2$, hydrocarbon full oxidation to $H_2O$ and $CO_2$ also takes place. For both $H_2O$ and $CO_2$ and at the same $X^{in}_{CH4}$, FIGS. 10A-10D show that between T=750-900° C., the selectivity and yield increase as T rises because of the Arrhenius-activated nature of the reactions. However, at the same T, addition of more $CH_4$ in the reactor decreases $S_{H2O}$ and $S_{CO2}$ Comparison with FIGS. 11C and 11D confirms that the system becomes more selective toward the formation of $C_2$ by adding more fuel in the reactor. As discussed earlier, this is consistent with the literature suggesting that increased $C_2$ selectivities can be achieved at high $CH_4$ to $O_2$ ratios. (See refs. 12, 26)

At T=750-850° C., FIGS. 12E-12H show that the selectivities to $H_2$ and CO are below 15%, while the corresponding yields are lower than 2%. This confirms that the system is not very active toward syngas production. However, a different trend is observed at 900° C. At this T, an increase in the yields of $H_2$ and CO is observed. As will be discussed in the next section, this behavior is related to several competing reactions leading to syngas production because of enhanced gas-phase reactivity at 900° C.

6. Mixture Composition near the $CH_4$ Side Gas-Membrane Interface and Comparison with Outlet Values. In Section 5 (Results and Discussion), the steady-state performance of BFZ91 with $La_2O_3$ toward $CH_4$ conversion to products was analyzed. Based on FIGS. 11A-11H, FIGS. 12A-12H, and FIGS. 27A-27F, significant information was obtained about the primary reactions of the OCM chemistry with and without $La_2O_3$. However, FIGS. 11A-11H and FIGS. 12A-13H focus on measurements at the outlet of the reactor. It has already been demonstrated in Section 3 that measurements at the outlet can be different compared to measurements near the membrane surface. This is true when the mixture composition includes species with significant gas-phase reactivity (such as $CH_4$, $C_2H_6$ and $C_2H_4$) and becomes more important as T rises. In the presence of $La_2O_3$, measurements with an alumina micro-probe near the membrane surface allow us to identify the reactions taking place due to the membrane-catalyst interaction. At the same time, these measurements provide information about gas-phase reactions not related to the membrane-catalyst presence such as the ones happening in the reactor's post-catalytic zone. FIGS. 13A-13H and FIGS. 14A-14H compare the $CH_4$ side membrane (i.e., near the membrane surface but still in the gas-phase and within the $La_2O_3$ bed) and outlet (i.e. at the outlet of the reactor) mole fractions of $O_2$, $CH_4$, $CO_2$, CO, $C_2H_6$, $C_2H_4$, $H_2O$, and $H_2$. For the entire data set, mole fractions less than 0.01% were measured for propane, propene, propadiene, and propyne. $C_2H_2$ was zero at 750-850° C., while mole fractions between 0.01 and 0.05% were measured at 900° C.

In the absence of fuel (i.e., for the cases with $X^{in}_{CH4}$=0%), FIG. 13A shows that $X^{mem}_{O2}$ increases as T rises, consistent with the higher $J_{O2}$ observed in FIG. 11A. When $CH_4$ is added, the presence of the catalyst reduces $X^{mem}_{O2}$ significantly and leads to conditions where $C_{O2}\approx$ 100% (FIG. 13B). At T=750-800° C., surface reactions at the $CH_4$ side limit $J_{O2}$, and hence, $J_{O2}$ is almost constant despite the fact that a low $P_{O2}$ environment evolves in the vicinity of the membrane. At higher T, surface reactions are accelerated, and hence, $J_{O2}$ increases at T=850-900° C. as more $CH_4$ is added. FIG. 13B shows that $X^{out}_{O2}$ follows the same trend as $X^{mem}_{O2}$, with $X^{mem}_{O2}>X^{out}_{O2}$ for all experimental points. For nonreactive cases, the trend is consistent given that a higher mole fraction of $O_2$ is expected near the membrane surface, which then decreases at the outlet because of gaseous diffusion. For reactive cases, the results demonstrate that most of the reaction of $O_2$ with $CH_4$ (or other products) takes place near the OCM catalyst with the remaining $O_2$ reacting in the gas phase with $CH_4$ or other products as the mixture exits the reactor.

FIGS. 13C and 13D show that a significant fraction of $CH_4$ remains nonreactive both near the membrane surface and at the outlet, consistent with the relatively low $C_{CH4}$, as reported in FIG. 11B. However, mole fractions at the outlet are lower than the ones near the membrane; the trend is more apparent as the temperature increases and is consistent with gas-phase reactivity as the mixture exits the reactor. For the same $X^{in}_{CH4}$, less $CH_4$ is measured at higher T, which explains the higher $C_{CH4}$ observed as T rises.

Figures 30A, 30B, 30C:
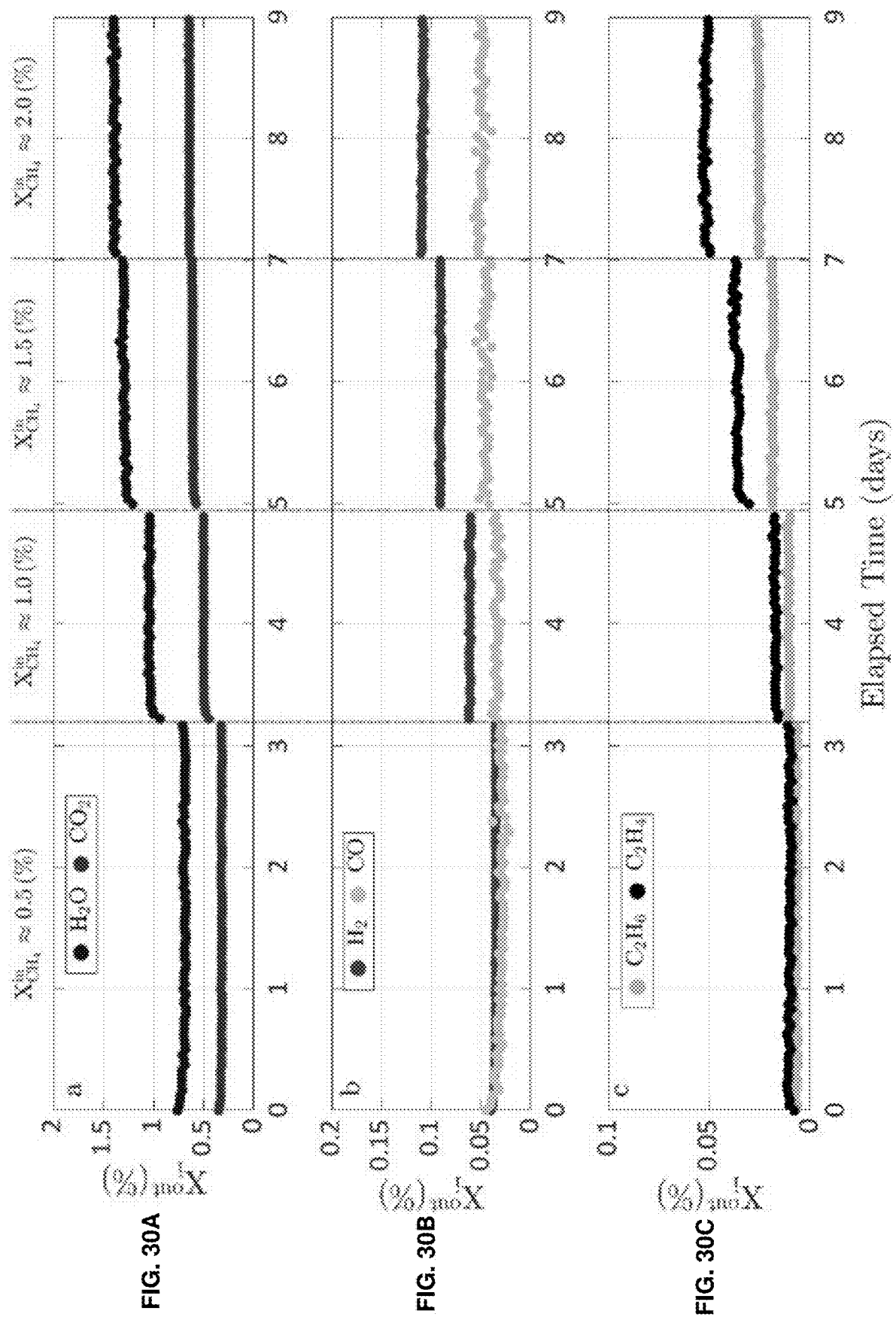
FIGS. 30A-30C depict long-term performance of BFZ91 with $La_2O_3$ at T=850° C. under partial $O_2$ consumption conditions.

FIGS. 13E and 14E show that significant quantities of $CO_2$ and $H_2O$ form within the $La_2O_3$ catalyst. The fact that $X^{mem}_{H2O}/X^{mem}_{CO2}>2$ suggests the full oxidation of $CH_4$. The full oxidation of $C_2H_6$ and $C_2H_4$ to $CO_2$ and $H_2O$ results in $X_{H2O}/X_{CO2}$ equal to 1.5 and 1, respectively. Clear evidence of $CH_4$ full oxidation is also shown in FIG. 30A (partial $O_2$ consumption experiment discussed in section 7). At T=750-850° C., the mole fractions of $CO_2$ and $H_2O$ near the membrane surface are nearly the same as the ones at the outlet (see FIGS. 13F and 14F). This demonstrates that $CH_4$ full oxidation takes place within the $La_2O_3$ bed, and then, the produced $H_2O$ and $CO_2$ transport to the exit of the reactor without reacting much with $CH_4$ or with other products. In addition, FIGS. 14A and 14C show that both $C_2H_6$ and $C_2H_4$ form near the membrane surface and within the $La_2O_3$ bed. This observation coupled with the fact that $X^{mem}_{H2O}/X^{mem}_{CO2}>2$ suggests that $CH_4$ full oxidation to $CO_2$ and $H_2O$ is happening simultaneously with $CH_4$ oxidative coupling to $C_2H_6$ and $H_2O$ (reaction 1). Both are facilitated by the presence of the $La_2O_3$ catalyst as the aforementioned reactions are not observed at considerable rates in the absence of $La_2O_3$ (FIGS. 7A-7H). $C_2H_6$ is known to precede the formation of $C_2H_4$, this is verified by the aforementioned results and has also been confirmed by others. (See refs. 89, 90)

Next, the pathway of the $C_2H_4$ formation from $C_2H_6$ was identified. To do so, the results, as shown in FIGS. 13A-13H an 14A-14H were considered. These plots confirm the existence of the following primary species within the $La_2O_3$ catalyst: $H_2O$, $CO_2$, $C_2H_6$, $C_2H_4$, $H_2$, CO, and unreacted $CH_4$. Because $O_2$ is fully consumed near the membrane, the formation of $C_2H_4$ and $H_2$ through NODHE takes place in the oxygen-free zone between the $La_2O_3$ catalyst and the exit of the reactor (compare FIG. 14A with FIG. 14B etc.). This is known from previous work. (See refs. 57, 58, 91) To remove the effect of this reaction from the analysis of the reactions happening on $La_2O_3$, the measurements near the membrane surface and within the $La_2O_3$ catalyst (i.e., do not consider the outlet data) were focused on. By looking at FIGS. 14C and 14G, it was observed that for a fixed T, $X^{mem}_{C2H4}$ and $X^{mem}_{H2}$ increase as $X^{in}_{CH4}$ increases. Based on this observation, the production of $C_2H_4$ and $H_2$ can be the result of the following pathways:

Pathway 1: ODHE to $C_2H_4$ and $H_2O$ followed by reaction to syngas. This pathway can be described through the following global reactions:

$$C_2H_6 + \frac{1}{2}O_2 \rightarrow C_2H_4 + H_2O \quad (11)$$

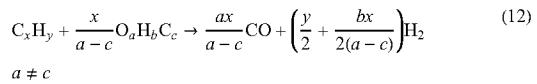

$$C_xH_y + \frac{x}{a-c}O_aH_bC_c \rightarrow \frac{ax}{a-c}CO + \left(\frac{y}{2} + \frac{bx}{2(a-c)}\right)H_2 \quad (12)$$

$$a \neq c$$

Regarding syngas production (reaction 12), it was noted that in general, syngas can be produced through oxidation, steam- or dry-reforming of $CH_4$, $C_2H_6$ and $C_2H_4$. In this analysis, one can be interested in the fact that syngas is produced through any reaction after ODHE. Hence, one can consider only one of these reactions without the loss of generality.

If this is the pathway taking place on $La_2O_3$, then, at a fixed T, both $X^{mem}_{CO}$ and $X^{mem}_{H2}$ should increase as $X^{in}_{CH4}$ increases. At T=750-850° C., FIG. 13G reveals an almost constant $X^{mem}_{CO}$ at $X^{mem}_{CO}\approx 0.10\%$, while FIG. 14G clearly shows that $X^{mem}_{H2}$ is increasing. The constant $X^{mem}_{CO}$ confirms that this pathway is not taking place at high rates. The production of $H_2$ should be accompanied by the production of CO if syngas production is taking place on $La_2O_3$ after ODHE. The constant value of $X^{mem}_{CO}$ also rules out the possibility of $H_2$ being produced through the water gas shift (WGS) as this would lead to decrease in $X^{mem}_{CO}$.

Pathway 2: NODHE to $C_2H_4$ and $H_2$. This pathway can be described through the following reaction:

$$C_2H_6 \rightarrow C_2H_4 + H_2 \tag{13}$$

At T=750-850° C., FIGS. 14C and 14G show that $X^{mem}_{C2H4} X^{mem}_{H2}$ but $X^{mem}_{H2}$ is always slightly higher than $X^{mem}_{C2H4}$. In conjunction with the fact that $X^{mem}_{CO}$ is nearly constant at $X^{mem}_{CO}\approx 0.10\%$, this confirms the validity of this pathway. It was already shown in this work that NODHE does not happen on $La_2O_3$ (FIGS. 27A-27F). The produced $H_2$ of this pathway has 2 contributions: (a) from one or multiple reactions producing syngas, which, however, are slow and kinetically frozen at T=750-850° C. after some CO and $H_2$ have been produced at low $X^{in}_{CH4}$ and (b) from NODHE.

The aforementioned analysis confirms that ODHE is not a major reaction within the membrane reactor. However, this does not mean that the reaction does not happen at all on $La_2O_3$ but rather, that within the reactor, the rate of ODHE on $La_2O_3$ is smaller than the rate of the primary reaction, NODHE (in the gas phase). However, evidence of ODHE has been reported in the literature, although the investigated catalysts were not pure $La_2O_3$ as in the study. For example, Stansch et al. (ref. 91) proposed ODHE to proceed on La-impregnated CaO, and they also added ODHE in their proposed reaction mechanism. However, SEM images were not provided in that work to identify whether the impregnation results to discrete $La_2O_3$ particles on CaO or to a full coating of CaO with $La_2O_3$. If the former is true, then a question that arises is whether the ODHE takes place on $La_2O_3$ or CaO or at their interface. In a similar way, Choudhary et al. (ref. 92) investigated ODHE over a Sr- and La-impregnated SA5205 support (consisting primarily of $Al_2O_3$ with some $SiO_2$). Although this paper confirms the presence of the ODHE reaction, it does not provide any data or conclusions in terms of whether this reaction proceeds in the gas phase or on the surface of the catalyst (on SrO or on $La_2O_3$ or at the SrO—$La_2O_3$ interface) or both. SEM images were not provided to investigate the catalyst's microstructure. In addition, the catalyst support was considered to be inert but results validating this hypothesis were not provided. Hence, given the different materials and the unknown microstructure of these catalysts compared to pure $La_2O_3$ as well as the lack of key evidence, it was concluded that the work by Stansch et al. (ref. 91) and Choudhary et al. (ref. 92) do not clearly support an ODHE pathway over pure $La_2O_3$.

The discussion above focuses on measurements between T=750-850° C., for which, the low and constant values of $X_{CO}^{mem}$ suggest that syngas reactions in the vicinity of $La_2O_3$ are slow and kinetically frozen, respectively. At T=900° C., the results show that reactions producing syngas are not kinetically frozen anymore and that gas-phase reactions are accelerated significantly. This is true even in the absence of $La_2O_3$ (see FIGS. 7A-7H). At T=900° C., there are several competing reactions leading to syngas production that should be considered, which complicates the analysis. First, under the operating T of this study, it is known that $CH_4$, $C_2H_6$, and $C_2H_4$ can be partially oxidized or reformed (with $H_2O$ and/or $CO_2$) into syngas. (See refs. 26, 91) Second, the formation of CO and $H_2O$ through the reverse WGS reaction is favored thermodynamically at T>818° C., while the formation of $CO_2$ and $H_2$ is favored at lower T. Third, decomposition of $C_2H_4$ is also accelerated as T increases. For example, at T=900° C., $X_{H2}^{mem}>>X_{C2H4}^{mem}$ and one can attribute this to the additional non-oxidative dehydrogenation of $C_2H_4$ in the gas phase. Therefore, although the proposed mechanism is clear for T=750-850° C. given that the aforementioned reactions are sluggish within this temperature regime, the multiple competing pathways because of the enhanced gas-phase chemistry at T=900° C. make the analysis at this T difficult. At this T, a safe conclusion about the reactions leading to syngas production is only possible through the use of computational models, and hence, no further analysis on the reactions resulting to syngas production will be attempted here.

Figures 15I, 15J, 15K, 15L, 15M, 15N, 15O, 15P:
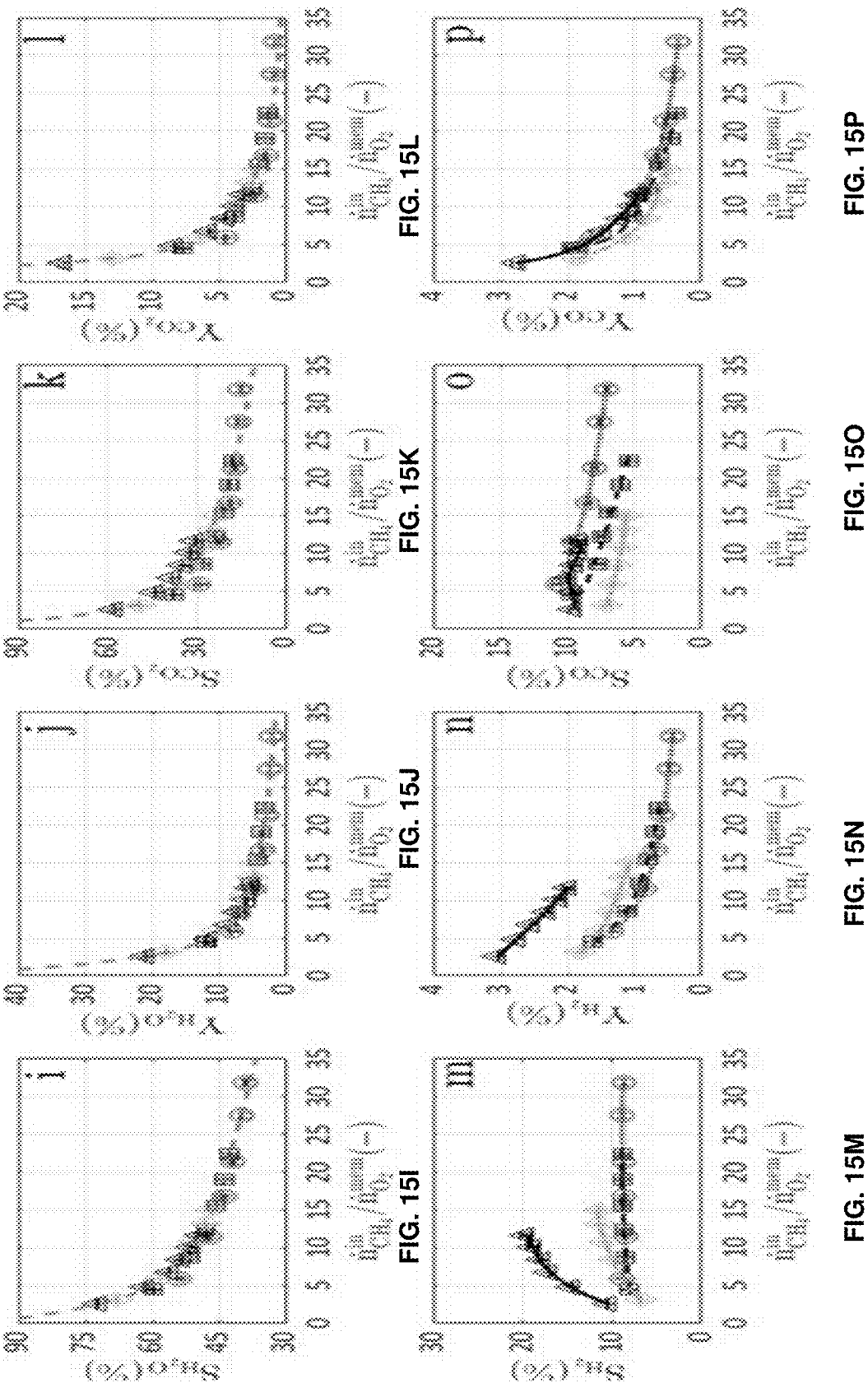

To enable the comparison of the results of this work with other studies in the literature, it was decided to plot the most important performance metrics as a function of T and $\dot{n}^{in}_{CH4}/\dot{n}^{mem}_{O2}$, that is, the ratio of the $CH_4$ mole flow rate at the inlet of the $CH_4$ side over the mole flow rate of $O_2$ through the membrane. This definition is consistent with the standard used in traditional OCM, where results are plotted as a function of T and $X_{CH4}/X_{O2}$ given that $CH_4$ and $O_2$ are co-fed at the inlet of the reactor. FIGS. 15A-15P summarize the results and reveal some very interesting trends. First, although the independent variables of the measurements are T and $X^{in}_{CH4}$, it was observed that $\dot{n}^{in}_{CH4}/\dot{n}^{mem}_{O2}$ is not constant at each T. Given that $J_{O2}$ increases at higher T and as more $CH_4$ is introduced in the reactor, the operating window of $\dot{n}^{in}_{CH4}/\dot{n}^{mem}_{O2}$ narrows down. Second, the results reveal that the highest $C_2H_6$ and $C_2H_4$ yields are obtained as $\dot{n}^{in}_{CH4}/\dot{n}^{mem}_{O2}$ decreases while the highest selectivities are obtained as $\dot{n}^{in}_{CH4}/\dot{n}^{mem}_{O2}$ increases. The highest $C_2$ yield is $Y_{C2}\approx 10.3\%$ obtained at T=850° C. for $\dot{n}^{in}_{CH4}/\dot{n}^{mem}_{O2}\approx 3.1$, which is very close to a stoichiometric ratio of 2. Finally, it was observed that for some of the performance metrics ($C_{CH4}$, $S_{H2O}$, $Y_{H2O}$, $S_{CO2}$, and $Y_{CO2}$), all data points collapse into the same curve demonstrating that they depend exclusively on $\dot{n}^{in}_{CH4}/\dot{n}^{mem}_{O2}$ (recall, though, that $\dot{n}^{mem}_{O2}$ is a function of T and $\dot{n}^{in}_{CH4}$); however, this is not the case for the species of interest, that is, $S_{C2H6}$, $Y_{C2H6}$, $S_{C2H4}$, and $Y_{C2H4}$ although some similarity is observed for a part of the data (e.g., for $Y_{C2H6}$ at T=750-800° C. and for $Y_{C2H4}$ at T=850-900° C.). Based on the activation barriers ($E_a$) reported by Stansch et al. (ref. 91), $E_a$=48-68 (kJ/mol) for $CH_4$ oxidation (partial and full) while $E_a$=168-182 (kJ/mol) for $C_2H_6$ and $C_2H_4$ formation. Such high $E_a$ values do not support the observed temperature independence for some performance metrics given that $E_a/RT \approx 5-18$. They do explain, however, the temperature dependency for $C_2$. Because the $C_2H_6$ and $C_2H_4$ non-oxidative dehydrogenation happens in the gas phase within oxygen-free zones, the residence time is another variable that affects the aforementioned trends for $C_2$. However, further studies are required to elucidate the reasons why an explicit temperature independence is observed for $C_{CH4}$, $S_{H2O}$, $Y_{H2O}$, $S_{CO2}$, and $Y_{CO2}$. This is the first time that such similarity curves are reported for OCM and can be very useful as first-order estimates when designing commercial-scale reactors.

7. Performance and Stability of BFZ91 and $La_2O_3$ under Partial $O_2$ Consumption and under an Undiluted $CH_4$ Stream. In the previous sections, the stability of BFZ91 with $La_2O_3$ under conditions of full $O_2$ consumption was demonstrated (FIGS. 13A and 13B). However, Hayek et al. have reported that OCM catalysts may still undergo deactivation, which is masked if operating at $C_{O2}\approx100\%$; they confirmed this behavior for the $Mn_xO_y$–$Na_2WO_4/SiO_2$ catalyst. (See ref. 93) Although this catalyst is known to be very unstable and to exhibit different phase transformations leading to OCM performance loss as a function of time (see ref. 94), another stability test was conducted, this time under conditions of partial $O_2$ consumption. The experiment was conducted using a new BFZ91 pellet and fresh $La_2O_3$ powder. Given that $J_{O2}$ is a function of T, $X^{in}_{CH4}$ and membrane thickness, the temperature was fixed at T=850° C. and a membrane thickness of 0.66 mm was selected while varying $X^{in}_{CH4}$. To cover more than one values of $CO_2$, long-term measurements at different $X^{in}_{CH4}$ were conducted.

Figures 16A, 16B, 16C:
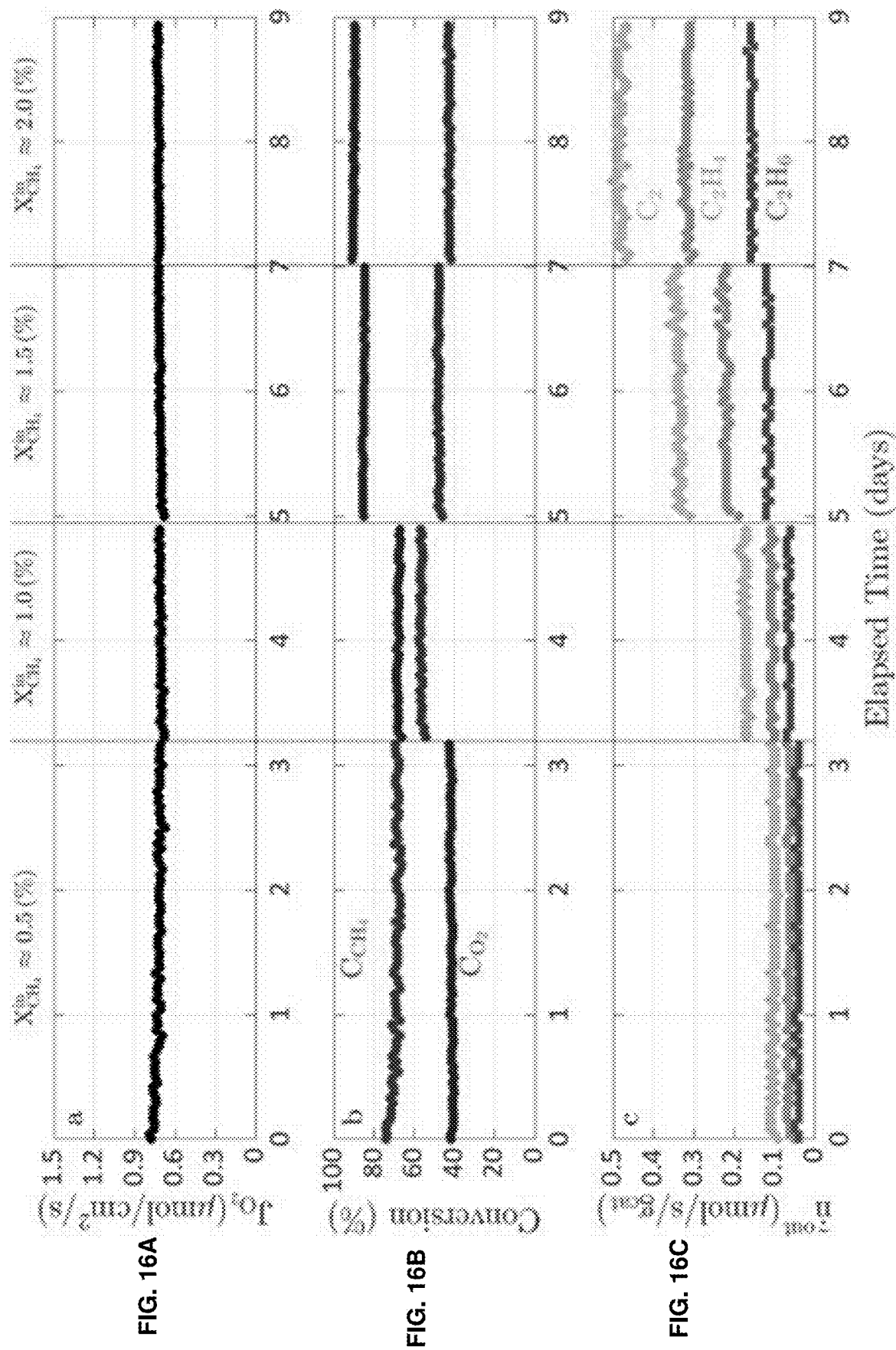
FIGS. 16A-16C depict long-term performance of BFZ91 with $La_2O_3$ at T=850° C. under partial $O_2$ consumption conditions.

FIGS. 16A-16C show $J_{O2}$, $C_{CH4}$, $CO_2$, and the activities of $C_2H_6$, $C_2H_4$, and $C_2$ as a function of time and $X^{in}_{CH4}$. In addition, FIGS. 28A-28B, 29A-29B, and 30A-30C show the species selectivities, yields, and outlet mole fractions, respectively. The results reveal some equilibration in the first few hours of the experiment after which the performance is very stable as a function of time. For comparison, Hayek et al. reported a significant performance loss within the first 4 days of measurements. In the case of $La_2O_3$, no deactivation was observed for 9 days of measurements under conditions of partial $O_2$ consumption.

Figure 17A:
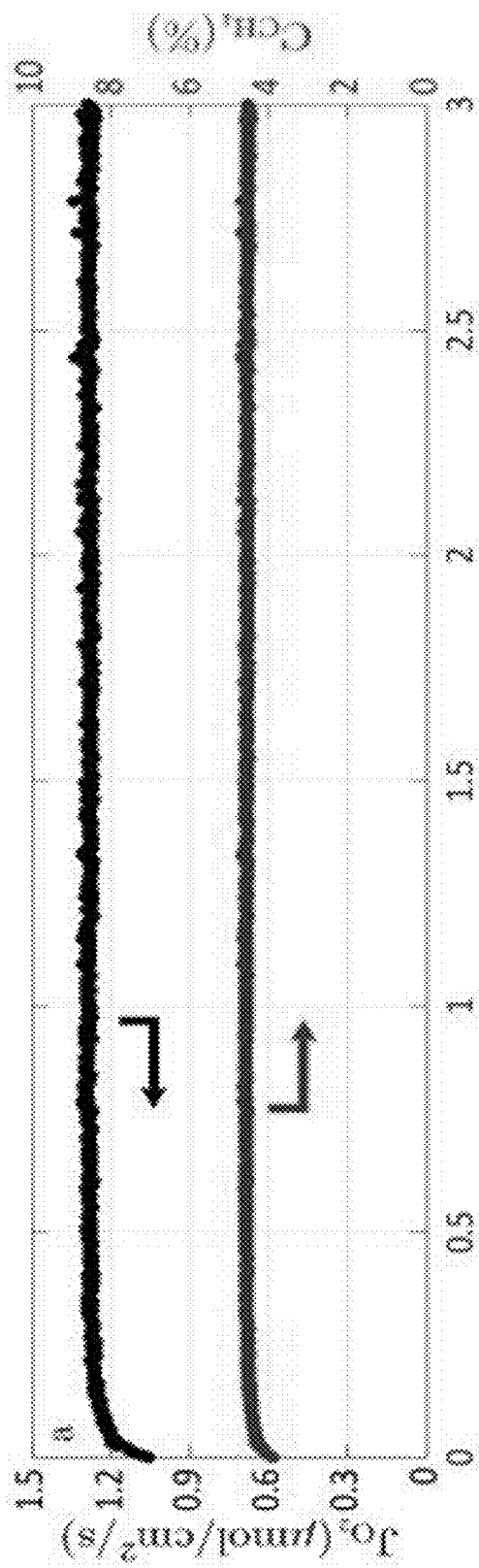
FIGS. 17A-17B depict long-term performance of BFZ91 with $La_2O_3$ at T=850° C. under pure $CH_4$.
Figure 17B:
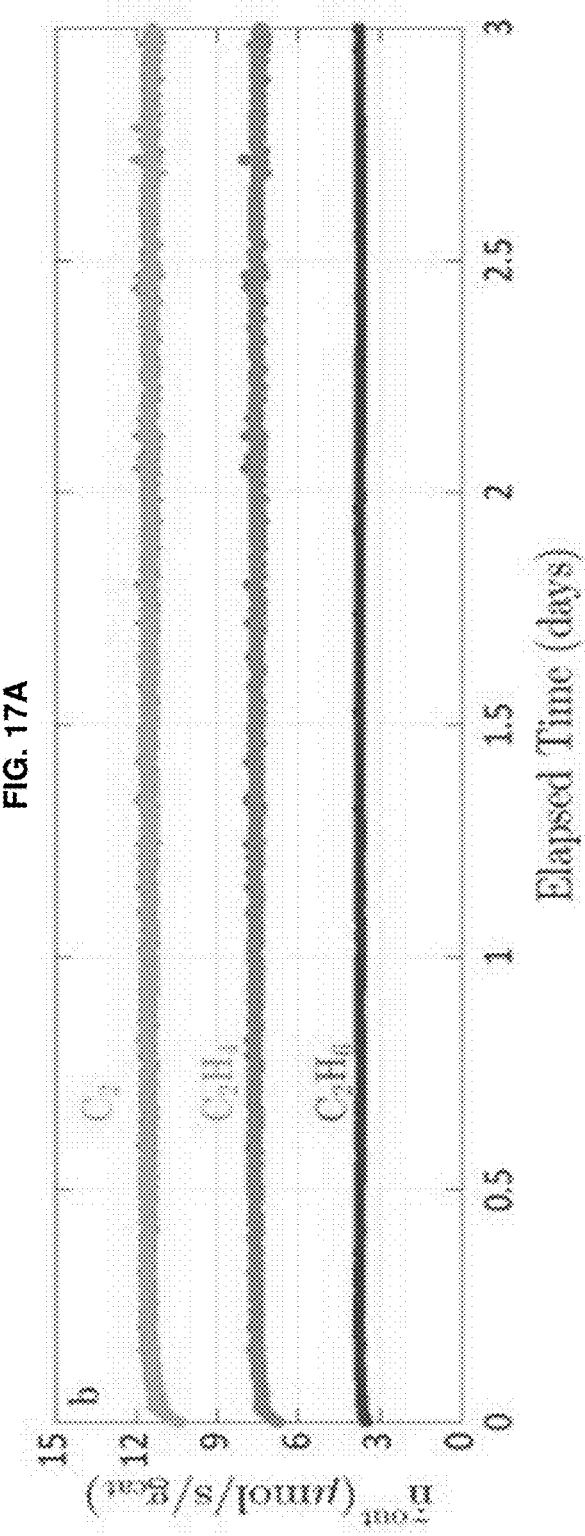

Having demonstrated the stability of BFZ91 with $La_2O_3$ in the aforementioned regime, the stability experiment was continued using the same materials, but this time pure $CH_4$ was used at the $CH_4$ side. The OCM performance as a function of time is shown in FIGS. 17A-17B and in FIGS. 31A-31B. The experiment lasted for 3 days after which it was terminated because no degradation was observed. The analysis of the mixture composition at the outlet of the $CH_4$ side was conducted every 4 min. After an equilibration period that took place within the first few hours of the measurement, $J_{O2}$, $C_{CH4}$, and the corresponding activities remained stable as a function of time. Under these conditions, $C_{O2}$=100%. $J_{O2}$ increased significantly because of operation under a reducing environment and reached $J_{O2}\approx1.3$ (µmol/cm²/s). Despite this $J_{O2}$ increase, $C_{CH4}\approx4.5\%$ which is low because of the limited amount of $O_2$ permeating through a low surface area lab-scale membrane. Operation at T=850° C. with a 0.66 mm thick BFZ91 membrane under pure $CH_4$ results to $\dot{n}^{in}_{CH4}/\dot{n}^{mem}_{O2}\approx45$ in the lab-scale reactor, which is significantly higher than ratios of 5-10 expected under industrial-scale OCM conditions. For this reason, high selectivities and low yields of $C_2H_6$ and $C_2H_4$ are obtained (see FIGS. 31A-31B).

Figures 32A, 32B:
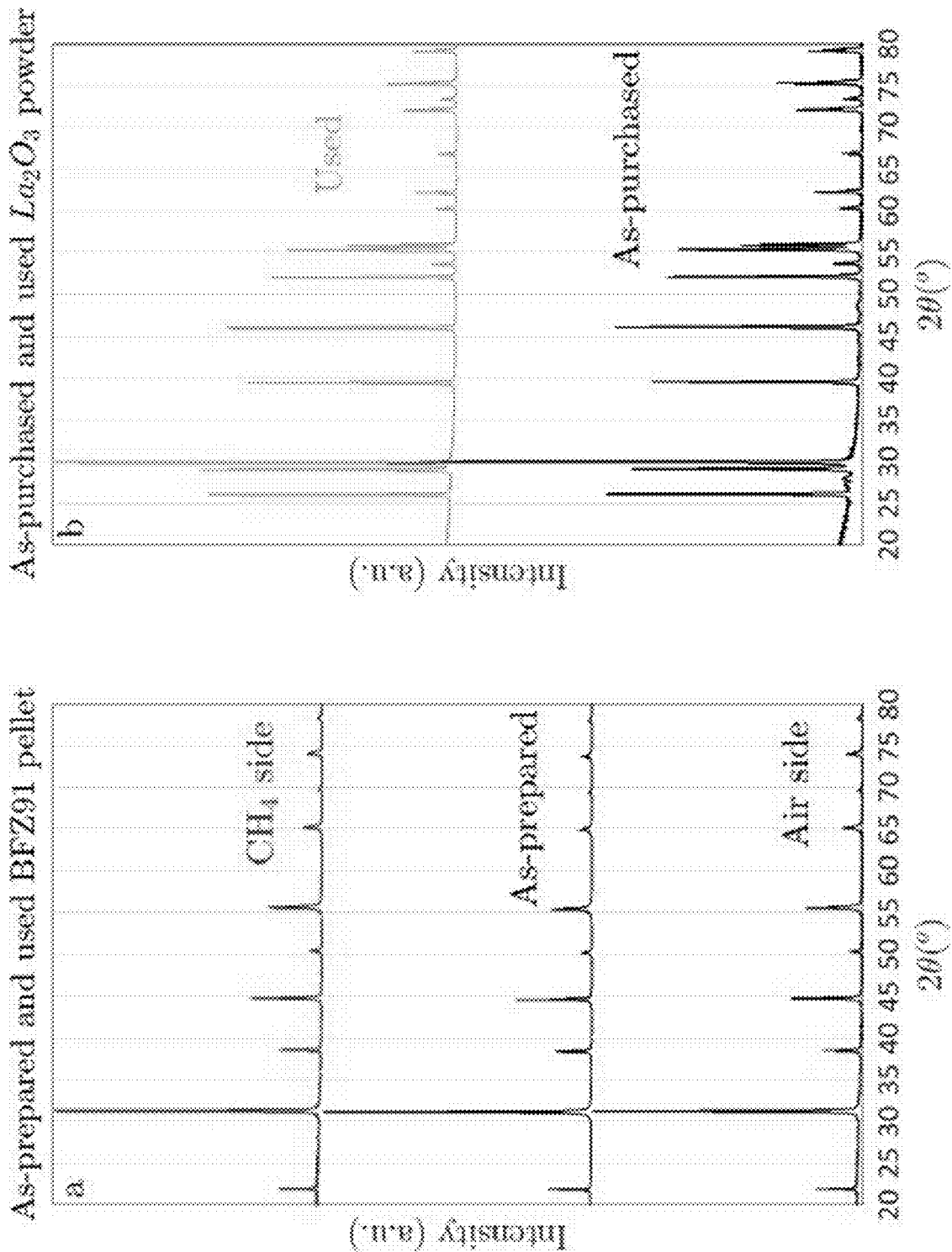

XRD results of the used materials show the absence of secondary phases (FIGS. 32A-32B). Although the air side BFZ91 and the $La_2O_3$ catalyst micro-structures shown in FIGS. 33A and 33C, respectively, do not reveal any differences when compared to the ones, as shown in FIGS. 10A-10F, this is not the case for the $CH_4$ side BFZ91 surface. As shown in FIG. 33B, several particles with different sizes and shapes have evolved on this surface. EDS mapping (FIG. 34) confirms that these particles are enriched in Fe but depleted in Ba and Zr, although this depletion is not significant (i.e., Ba and Zr still exist within the Fe-enriched zones); this does not point out to the formation of metallic Fe (Fe⁰) or Fe oxides ($Fe_xO_y$). These results suggest that secondary Fe-enriched $Ba_xFe_yZr_zO_a$ phases formed on the $CH_4$ side of the BFZ91 membrane and are possibly related to the decomposition of the BFZ91 membrane because of the extremely reducing environment ($\dot{n}^{in}_{CH4}/\dot{n}^{mem}_{O2}\approx45$). These particles do not exist on the $CH_4$ side of BFZ91 between $X^{in}_{CH4}$=0-30% (FIG. 10D). This Fe-enriched $Ba_xFe_yZr_zO_a$ phase is not amorphous (because it is analyzed through SEM-EDS), so a possible reason why it was not observed through XRD is because XRD is a bulk characterization technique, and this phase is probably located primarily on the surface of BFZ91 and not within its bulk.

One does not currently know at which stage of the 3-day experiment with pure $CH_4$ this Fe-enriched $Ba_xFe_yZr_zO_a$ phase started forming. One hypothesis is that this phase formed progressively as a function of time. If this is the case, then FIGS. 17A-17B confirm that it did not impact the performance of BFZ91 because no degradation was observed. However, longer trials are required to demonstrate if the performance can be compromised under prolonged exposure to pure $CH_4$. Another hypothesis is that this phase formed soon after pure $CH_4$ was introduced in the reactor. This could explain the reason of the observed equilibration within the first few hours of the experiment. If the aforementioned Fe-enriched $Ba_xFe_yZr_zO_a$ phase formed during this stage, it resulted in performance enhancement both in terms of $J_{O2}$ as well as $C_2$ production (FIGS. 17A-17B); and some studies have shown that similar perovskite oxides (e.g., $Ba_{0.5}Sr_{0.5}FeO_{3-\delta}$) are active OCM catalysts. (See ref. 37) The performance remained stable for the rest of the measurement, confirming that if this phase forms at the beginning of exposure to $CH_4$, it does not degrade the performance of BFZ91 with $La_2O_3$. Further studies are required to fully identify the stoichiometry of the proposed Fe-enriched $Ba_xFe_yZr_zO_a$ phase and whether it is indeed active for OCM. Finally, some carbon deposition is observed on the $CH_4$ side of the BFZ91 membrane (FIG. 34), which is confined to a few discrete locations and does not appear to degrade the performance of the investigated materials.

8. OCM Mechanism of BFZ91 with $La_2O_3$: Global Reactions, Rate-Limiting Steps, and Species Activation on the Catalyst. Based on the results, as shown in FIGS. 11A-11H, 12A-12H, 13A-13H and 14A-14H, and the discussion in Sections 5-7 (Results and Discussion), the following global reactions have been clearly identified on a macroscopic level when using BFZ91 membranes coupled with $La_2O_3$:

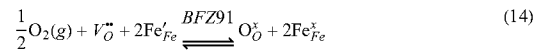

$$\frac{1}{2}O_2(g) + V_O^{\cdot\cdot} + 2Fe'_{Fe} \xrightleftharpoons{BFZ91} O_O^x + 2Fe^x_{Fe} \quad (14)$$

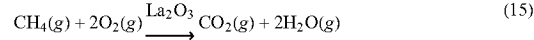

$$CH_4(g) + 2O_2(g) \xrightarrow{La_2O_3} CO_2(g) + 2H_2O(g) \quad (15)$$

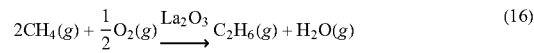

$$2CH_4(g) + \frac{1}{2}O_2(g) \xrightarrow{La_2O_3} C_2H_6(g) + H_2O(g) \quad (16)$$

$$C_2H_6(g) \to C_2H_4(g) + H_2(g) \quad (17)$$

For reactions 14-17, (g) denotes a species in the gas phase. Reaction 14 is written assuming that electrons are the main charge carriers for electronic conductivity, which is consistent with the defect chemistry of $Ba_{0.5}Sr_{0.5}FeO_{3-\delta}$. (See ref. 68) It is noted that it is reasonable to expect that the defect chemistry between BFZ91 and $Ba_{0.5}Sr_{0.5}FeO_{3-\delta}$ will be similar. The forward step of reaction 14 takes place on the air side gas-membrane interface and incorporates $O_2$ into the membrane; the reverse reaction occurs on the $CH_4$ side interface and releases $O_2$ into the gas phase. As discussed earlier, the possibility of the $CH_4$ reaction with $O_O^x$ on the gas-membrane interface or with $O_2$ in the gas phase has been excluded based on measurements in the absence of the $La_2O_3$ powder (Section 3).

Figure 18:
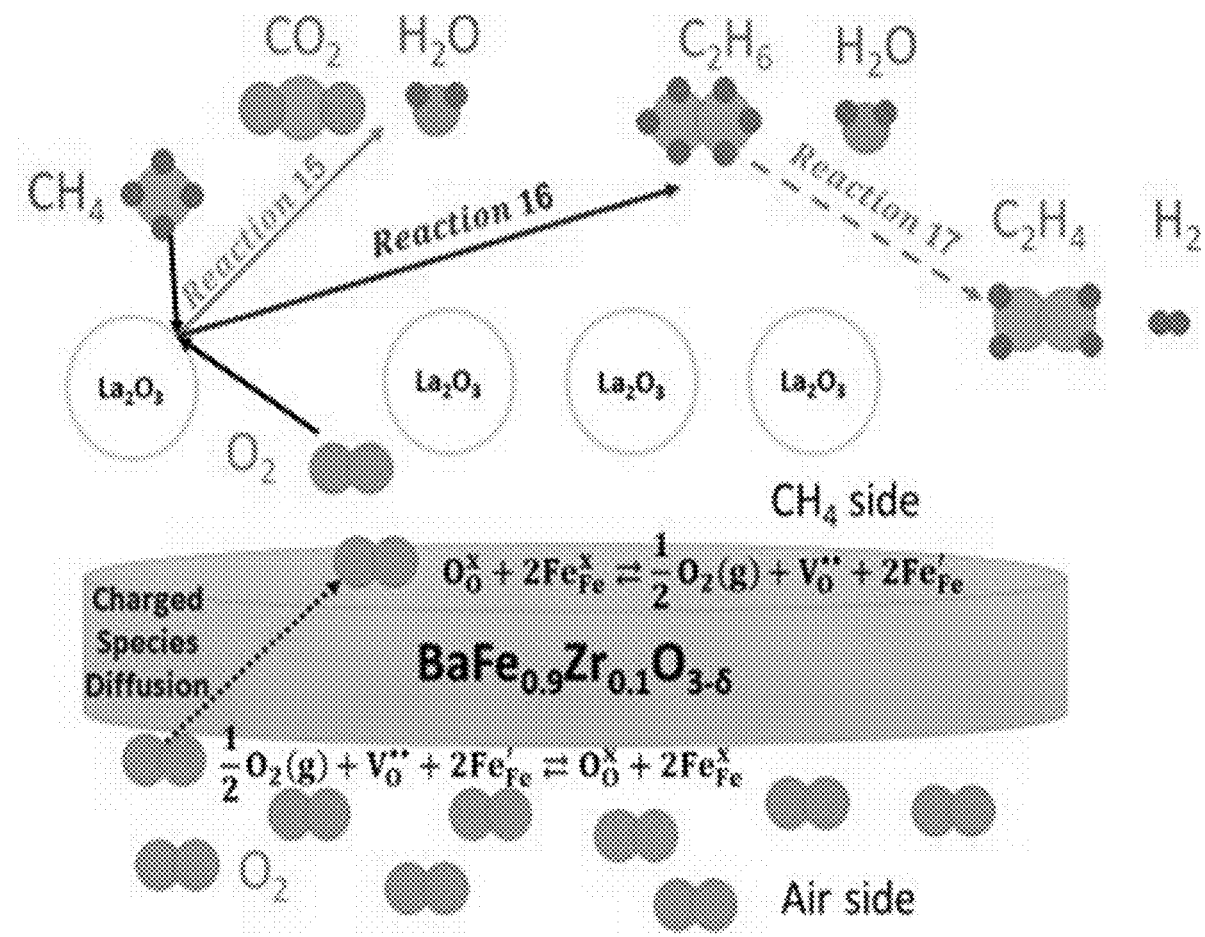
FIG. 18 depicts a schematic of the global reactions identified during OCM with BFZ91 membranes and $La_2O_3$ catalyst. Solid arrows correspond to reactions activated by the $La_2O_3$ catalyst. Dashed arrows represent gas-phase reactions. The dotted arrow signifies the transport of $O_2$ through the BFZ91 membrane. Reactions responsible for syngas production have been omitted.

According to FIGS. 11A-11H, 12A-12H, 13A-13H and 14A-14H, the $CH_4$ conversion increases significantly in the presence of $La_2O_3$. The analysis of the species composition near the $CH_4$ side membrane interface and at the outlet allows us to conclude that reactions 15 and 16 occur on the surface of the $La_2O_3$ catalyst. $C_2H_6$ formed via reaction 16 is then converted to $C_2H_4$ and $H_2$ in the gas phase according to reaction 17. As discussed earlier, CO (and $H_2$) may form because of oxidation and/or reforming of $CH_4$, $C_2H_6$, and $C_2H_4$ as well as through the (reverse) WGS. At T=750-850° C., syngas production is low and kinetically frozen within the $La_2O_3$ catalyst but it is accelerated significantly at T=900° C. At this T, identifying the presence and rate of reactions producing syngas requires the use of computational models and is outside the scope of this work. A schematic of the global reaction pathways identified in this work is shown in FIG. 18. With the exception of ODHE, these reactions are in agreement with the primary OCM reactions proposed by Stansch et al. who investigated the conventional OCM using a $La_2O_3/CaO$ catalyst. (See ref. 91)

Reactions 14-17 provide a macroscopic description of the OCM chemistry for BFZ91 and $La_2O_3$. Microscopically, several studies have already provided insight about the elementary steps of the OCM chemistry but significant disagreement still exists about the $CH_4$—$O_2$ activation process even for the same material. Early experiments have shown that $CH_4$ does not adsorb on the surface of $La_2O_3$. (See ref. 89) This has been confirmed by computational studies suggesting that the $CH_4$ physisorption on $La_2O_3$ is very weak. (See ref. 95) As a result, $CH_4$ is not expected to bind on $La_2O_3$ at any practical temperature. Instead, the $CH_4$ activation proceeds via a reaction that involves $CH_4$ in the gas-phase and an activated oxygen species ($O_2^*$) already adsorbed on $La_2O_3$ as follows:

$$O_2(g)+(s) \rightarrow O_2^*(s) \tag{18}$$

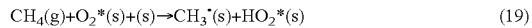
$$CH_4(g)+O_2^*(s)+(s) \rightarrow CH_3^{\cdot}(s)+HO_2^*(s) \tag{19}$$

$$CH_3^{\cdot}(s) \rightarrow CH_3^{\cdot}(g)+(s) \tag{20}$$

$$2CH_3^{\cdot}(g) \rightarrow C_2H_6(g) \tag{21}$$

In reactions 18-21, (s) denotes an empty site or a species on the surface of the catalyst. Reaction 18 corresponds to the gaseous $O_2$ adsorption on the surface of the catalyst and its activation to form $O_2^*$, while reaction 19 denotes the hydrogen abstraction from $CH_4$ in the presence of $O_2^*$ leading to the formation of methyl radicals ($CH_3^{\cdot}$) on the surface of the catalyst. The process continues with $CH_3^{\cdot}$ desorption into the gas phase through reaction 20, whose existence has been confirmed experimentally. (See ref. 56) Two $CH_3^{\cdot}$ will combine in the gas phase to form gaseous $C_2H_6$ through reaction 21. Then, $C_2H_6$ can in general be dehydrogenated to $C_2H_4$ through oxidative or non-oxidative pathways, as proposed in other studies. (See refs. 26, 90, 96) The results show that, within the membrane reactor with a $La_2O_3$ catalyst, the NODHE in the gas phase (reaction 17) is the primary reaction for producing $C_2H_4$.

Reaction 19 is probably the most important step of the OCM chemistry as it is typically considered rate limiting toward $C_2$ formation. However, the exact mechanism is still under debate and depends strongly on the catalyst's properties. On the one side, it has been proposed that the C—H bond cleavage is homolytic and is activated by a surface $O_2^*$ in a single step, as proposed by reaction. (See refs. 19, 26, 90, 97) In contrast, a heterolytic C—H bond splitting on the surface of the catalyst has also been considered. (See refs 89, 90, 96) For $La_2O_3$, Wang et al. demonstrated computationally that reaction 19 proceeds on the (001) surface in two steps: the first step involves a heterolytic $CH_3$—H bond splitting with $CH_3^-$ binding on a $La^{3+}$ bridge site and $H^+$ binding on a neighboring $O^{2-}$ site through an acid-base pair mechanism; after $CH_3^{\cdot}$ desorption into the gas phase, the second step involves the activation of another $CH_4$ on the $La^{3+}$ bridge site forming $CH_3^{\cdot}$ through homolytic hydrogen abstraction from $CH_4$ induced by the activated $O_2^*$ surface species. (See ref. 95)

A second source of disagreement is related to the activated $O_2^*$ species that favors the production of $CH_3^{\cdot}$ and hence $C_2$. In general, several oxygen species such as superoxide ($O_2^{1-}$), peroxide ($O_2^{2-}$) oxygen radical ($O^{1-}$), and $O^{2-}$ may evolve on the surface of a catalyst. Out of these, $O^{2-}$ has been correlated with $CH_4$ full oxidation while the remaining species have been linked with $C_2$ production. (See refs. 60, 61, 78) Isotope-exchange experiments performed by Lacombe et al. demonstrated that the adsorption of molecular $O_2$ on $La_2O_3$ happens dissociatively (see ref. 89); they also hypothesized that the electrophilic site formed during the $O_2$ adsorption on $La_2O_3$ is either $O^{1-}$ or $O_2^{1-}$. (See ref. 89) Earlier electron paramagnetic resonance spectroscopy measurements performed by Wang and Lunsford had already shown evidence of $O_2^{1-}$ on the surface of $La_2O_3$. (See ref. 98) A computational study by Palmer et al. confirmed the dissociative adsorption of molecular $O_2$ on the (001) plane of $La_2O_3$ (see ref. 99); however, further binding with an oxygen ion on the $La_2O_3$ surface resulted in the formation of $O_2^{2-}$ (see ref. 99), which did not agree with the results of Wang and Lunsford (ref. 98). A recent computational study predicted $O_2^{1-}$ as the activated oxygen species on $La_2O_3$ during the second step of reaction 19. (See ref. 95) Note, however, that the aforementioned studies (refs. 89, 95, 98, 99) dealt exclusively with the determination of the active site upon $O_2$ adsorption on $La_2O_3$ without correlating it with the OCM activity of the catalyst; the latter has been demonstrated for other OCM catalysts and a link between the $C_2$ yield and the concentration of the activated $O_2$ species was established. (See ref. 100) Identifying and quantifying active species on the surface of OCM catalysts using in situ characterization techniques and correlating these with the $C_2$ yield is expected to advance the start-of-the-art on OCM.

Finally, based on FIGS. 27A-27F, it was shown that the non-oxidative dehydrogenation of $C_2H_6$, $C_2H_4$, and $CH_4$ does not take place on $La_2O_3$ between T=750-900° C. Given that $CH_4$ does not adsorb on $La_2O_3$ (see refs. 89, 95) it is reasonable to assume the same for $C_2H_6$ and $C_2H_4$. Fundamentally, this could explain the results shown in FIGS. 27A-27F. However, further studies based on isotope-exchange measurements are required to confirm this hypothesis.

CONCLUSIONS This work investigates OCM in CMRs as a means to produce $C_2$ hydrocarbons from $CH_4$. A BFZ91 membrane was used for $O_2$ separation from air and $La_2O_3$ was selected as the OCM catalyst. Long-term experiments were conducted in a button-cell reactor at T=750-900° C. and $X^{in}_{CH4}$=0-30%. These measurements reveal that the BFZ91-$La_2O_3$ combination is chemically and structurally stable for 23 days, during which no loss of performance was observed. The performance of the materials was also investigated under partial $O_2$ consumption and pure $CH_4$ conditions. The BFZ91 membrane and $La_2O_3$ catalyst were characterized before and after the OCM measurements and significant information about each was obtained, especially regarding their stability under OCM conditions. The highest $C_2$ yield is ~10% obtained at $C_2$ selectivity of ~39%. These values were achieved at T=850° C. and $X^{in}_{CH_4}$=5% during which $J_{O_2}$≈0.91 (μmol/cm²/s). Experimental measurements in the absence of $La_2O_3$ revealed that the membrane does not catalyze $CH_4$ pyrolysis or oxidation on its surface at high rates, and hence, undesired $CH_4$ conversion to species other than $C_2$ because of the membrane presence is avoided. Based on the results presented in this work, the primary OCM chemistry within the reactor is identified to consist of: (1) the $CH_4$ full oxidation to $CO_2$ and $H_2O$, (2) the $CH_4$ oxidative coupling to $C_2H_6$ and $H_2O$, (3) the $C_2H_6$ non-oxidative dehydrogenation to $C_2H_4$ and $H_2$, and (4) the oxidation/reforming of $CH_4$, $C_2H_6$, and $C_2H_4$ combined with the (reverse) WGS to produce syngas. The first two reactions happen on $La_2O_3$ and the third takes place exclusively in the gas phase. The reactions in the fourth category are slow and kinetically frozen at T=750-850° C. but they accelerate at T=900° C. and can happen both in the gas phase and on the $La_2O_3$ catalyst. Based on early and recent experimental-computational results, the mechanism of C—H bond breaking and the oxygen activation on $La_2O_3$ was presented in an effort to deepen the understanding on the OCM chemistry from a microscopic level.

Additional experimental details follow.

Figure 19:
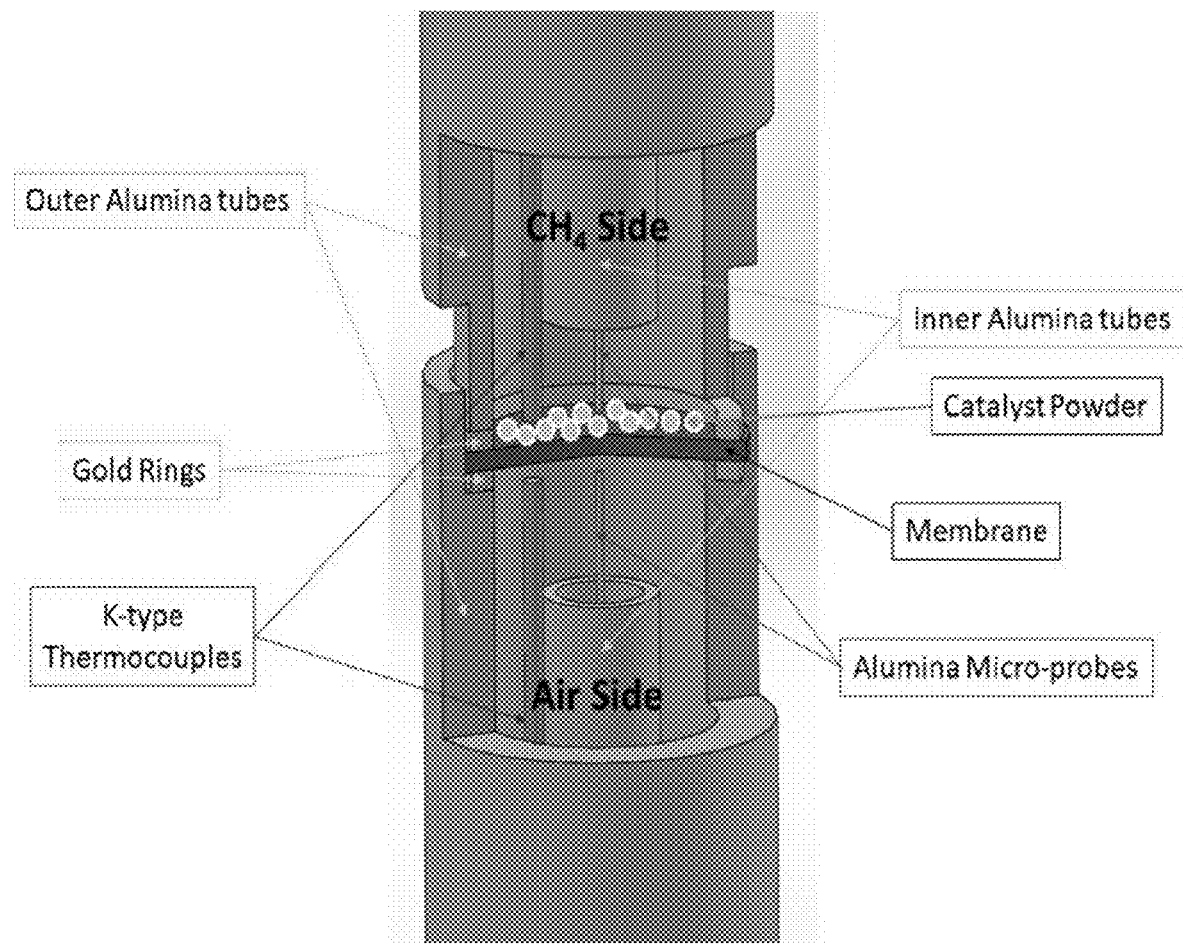
FIG. 19 depicts a button-cell reactor used for the OCM measurements. The bottom side corresponds to the air side of the reactor where $O_2$ from air is incorporated into the membrane. The top side corresponds to the $CH_4$ side of the reactor where OCM takes place. The $La_2O_3$ catalyst is deposited on the $CH_4$ side of the membrane to convert $CH_4$ to $C_2$ (see FIG. 20 regarding the catalyst loading and geometry on the BFZ91 membrane).

Experimental Setup for OCM measurements and Loading of the $La_2O_3$ Powder on the BFZ91 Membrane FIG. 19 shows the experimental setup used in the current investigation. The setup consists of alumina outer tubes that squeeze the membrane using gold rings to ensure a gas-tight system with minimized air leaks. The gold rings were purchased from Lux Bond & Green. The inner alumina tubes are used for the flow introduction. K-type thermocouples are used to monitor the temperature on each reactor side. Alumina micro-probes were introduced into each stream to measure the gas-phase composition near the membrane surface.

During the experiment, ambient air was flowing in the air side with a volumetric flow rate equal to 200 sccm. Mixtures of methane ($CH_4$) diluted in argon (Ar) were introduced in the $CH_4$ side with a fixed total volumetric flow rate equal to 100 sccm. The flow rate was controlled using Mass Flow Controllers purchased by Brooks Instrument. All measurements were conducted in atmospheric pressure.

Species mole fractions at the fuel side inlet, outlet and near the membrane surface were measured using a 490 MicroGC from Agilent Technologies. The Gas Chromatograph (GC) is equipped with the Molsieve 5 Å, COX, PoraPLOT U and PoraPLOT Q columns that allow measurement of $O_2$, $N_2$, $H_2$, CO, $CO_2$, $CH_4$, $C_2H_6$, $C_2H_4$, $C_2H_2$, $C_3H_8$, C3H6, propadiene ($C_3H_{4iene}$) and propyne ($C_3H_{4yne}$). Ar was used as the carrier gas of the GC.

Figure 20:
FIG. 20 depicts a $La_2O_3$ catalyst on a ceramic membrane.

To conduct OCM measurements, 0.1 g of $La_2O_3$ powder were deposited on the BFZ91 membrane as shown in FIG. 20 and described below. To position the $La_2O_3$ powder on the BFZ91 membrane, a ring was used that has an outer diameter equal to 16 mm (i.e. equal to the outer diameter of the BFZ91 pellet), inner diameter equal to 12.5 mm (i.e. equal to the effective diameter of the BFZ91 membrane, which is dictated by the thickness of the outer alumina tubes, as shown in FIG. 19) and thickness of 1.5 mm. First, the BFZ91 membrane was loaded on the air side outer alumina tube followed by placing the aforementioned ring on top of the membrane. The $La_2O_3$ powder was deposited at the center of the ring and then, a spatula was used to make sure it fully covers the effective area of the membrane. The next step was to press the catalyst downwards to ensure that the catalyst bed has a uniform thickness. Because of this, the thickness of the $La_2O_3$ catalyst bed is similar to the thickness of the ring, i.e. 1.5 mm. Finally, the ring was removed with a plier leading to the configuration shown in FIG. 20 and the $CH_4$ side outer alumina tube was added in the assembly. During the measurements, the alumina micro-probe was embedded into the catalyst bed.

Prior to OCM measurements, it was confirmed that the position of the $La_2O_3$ powder was not impacted by the flow and hence, the catalyst bed is fixed within the reactor without particle mobility due to the gaseous flow. It was also confirmed that the gas extraction through the alumina micro-probe does not remove the catalyst from the reactor. These two tests were important to ensure that there was no loss of catalyst during the OCM measurements and that the catalyst remains in place during the reaction.

Estimation of $J_{O_2}$, $CH_4$ Conversion, $O_2$ Conversion, $C_2$ Selectivity, Yield and Activity In the absence of $CH_4$ (non-reactive measurement), the oxygen flux through the membrane is calculated using a system of equations reported in Dimitrakopoulos, G.; Ghoniem, A. F. A Two-Step Surface Exchange Mechanism and Detailed Defect Transport to Model Oxygen Permeation Through the $La_{0.9}Ca_{0.1}FeO_{3-\delta}$ Mixed-Conductor. J. Membr. Sci. 510 (2016) 209-219, which is incorporated by reference in its entirety.

In the presence of $CH_4$ (reactive measurement), the oxygen flux $J_{O_2}$, $CH_4$ and $O_2$ conversion, $C_2$ selectivity, yield and activity are calculated by solving a system of mole balance equations for hydrogen (H), carbon (C), nitrogen (N) and oxygen (O) atoms, an equation for the molecular weight of the mixture at the outlet and another one that involves the summation of mole fractions of species at the outlet. The conservation of nitrogen takes into account the finite leak of air into the $CH_4$ side of the reactor. By measuring the nitrogen mole fraction at the outlet of the $CH_4$ side, one can keep track of the amount of oxygen due to air leak. At the inlet of the $CH_4$ side, $O_2$, $N_2$, $CH_4$ and Ar and are considered ($O_2$ and $N_2$ here account for potential leaks of air in the inlet gas stream before introduction into the reactor). At the outlet of the $CH_4$ side, the following N=15 species are considered: Ar, $O_2$, $N_2$, $H_2$, $H_2O$, CO, $CO_2$, $CH_4$, $C_2H_6$, $C_2H_4$, $C_2H_2$, $C_3H_8$, $C_3H_6$, $C_3H_{4iene}$ and $C_3H_{4yne}$. Based on the above, the following system of equations is considered for $CH_4$—Ar—$O_2$—$N_2$ mixtures at the inlet of the $CH_4$ side:

$$\frac{\dot{m}^{in}_{mix}}{W^{in}_{mix}} X^{in}_{CH_4} = \frac{\dot{m}^{out}_{mix}}{W^{out}_{mix}} \left[ \left( X^{out}_{CH_4} + X^{out}_{CO} + X^{out}_{CO_2} \right) + 2\left( X^{out}_{C_2H_6} + X^{out}_{C_2H_4} + X^{out}_{C_2H_2} \right) + + 3\left( X^{out}_{C_3H_8} + X^{out}_{C_3H_6} + X^{out}_{C_3H_{4iene}} + X^{out}_{C_3H_{4yne}} \right) \right] \quad (22)$$

$$\frac{\dot{m}^{in}_{mix}}{W^{in}_{mix}} \left( 4 X^{in}_{CH_4} \right) = \frac{\dot{m}^{out}_{mix}}{W^{out}_{mix}} \left[ 8\left( X^{out}_{C_3H_8} \right) + 6\left( X^{out}_{C_2H_6} + X^{out}_{C_3H_6} \right) + + 4\left( X^{out}_{CH_4} + X^{out}_{C_2H_4} + X^{out}_{C_3H_{4iene}} + X^{out}_{C_3H_{4yne}} \right) + 2\left( X^{out}_{H_2} + X^{out}_{H_2O} + X^{out}_{C_2H_2} \right) \right] \quad (23)$$

-continued $$\frac{\dot{m}_{mix}^{in}}{W_{mix}^{in}} X_{N_2}^{in} + \frac{\dot{m}_{mix}^{leak}}{W_{mix}^{leak}} X_{N_2}^{leak} = \frac{\dot{m}_{mix}^{out}}{W_{mix}^{out}} X_{N_2}^{out} \tag{24}$$

$$\frac{\dot{m}_{mix}^{in}}{W_{mix}^{in}} (2X_{O_2}^{in}) + \frac{\dot{m}_{mix}^{leak}}{W_{mix}^{leak}} (2X_{O_2}^{leak}) + \frac{\dot{m}^{mem}_{mix}}{W^{mem}_{mix}} X_O^{mem} = \frac{\dot{m}_{mix}^{out}}{W_{mix}^{out}} [2(X_{O_2}^{out} + X_{CO_2}^{out}) + (X_{CO}^{out} + X_{H_2O}^{out})] \tag{25}$$

$$W_{mix}^{out} = \sum_{i=1}^{N} X_i^{out} W_i \tag{26}$$

$$\sum_{i=1}^{N} X_i^{out} = 1 \tag{27}$$

In equations (22)-(27), $X_i$ denotes the mole fraction of species i at a particular location of the $CH_4$ side (inlet, outlet, through the membrane and due to leaks), m is the mass flow rate of the mixture at a particular location (inlet, outlet, through the membrane and due to leaks) and W is the molecular weight of species i or that of the mixture at a particular location (inlet, outlet, through the membrane and due to leaks). Analysis of the mixture composition at the inlet of the $CH_4$ side using the GC gives $X^{in}_{N2} \approx 0.04\%$ and $X^{in}_{O2} \approx 0.01\%$ for all the measurements, demonstrating that the $CH_4$ side inlet has almost zero air leaks.

To protect the columns of the GC, steam should not enter into the instrument. To avoid steam introduction into the GC, silica is used as a desiccant material. Plastic tubes filled with silica are inserted prior to the entrance of the GC to adsorb the humidity of the gaseous sample. However, by doing so, the species mole fractions measured by the GC are based on the dry mixture. Within the reactor, the mixture is wet (i.e. includes $H_2O$) and hence, when calculating the performance metrics, the real (i.e. on a wet basis) mole fractions of the corresponding species within the reactor should be used instead of the ones of the dry mixture.

Because of the aforementioned mole fraction difference between real (i.e. at the outlet of the reactor on a wet basis) and measured by the GC (on a dry basis after $H_2O$ removal) values, the real mole fraction of species i at the outlet of the reactor, $X^{out}_i$, is always lower than the measured mole fraction of species i using the GC, $X^{out,GC}_i$. These two are related through the following equation:

$$X_i^{out,GC} = \frac{X_i^{out}}{1 - X_{H_2O}^{out}}, i = 1 \ldots N - 2 \text{(i.e. all species except } H_2O \text{ and Ar)} \tag{28}$$

In equation (28), $X^{out}_{H2O}$ is the mole fraction of steam at the outlet of the reactor and i accounts for the N−2=13 species measured by the GC (i.e. excluding $H_2O$ and Ar). Regarding Ar, although the inlet-outlet mixtures are diluted in Ar, the mole fraction of Ar is not measured by the GC given that the GC operates with Ar as the carrier gas. Despite that, the Ar mole fraction at the inlet is calculated directly since $O_2$, $N_2$ and $CH_4$ at the inlet are measured. At the outlet of the $CH_4$ side, is estimated by the solution of the equations (22)-(28).

Equations (22)-(28) involve a system of 19 equations with 19 unknowns: $\dot{m}^{leak}_{mix}$, $\dot{m}^{mem}_{mix}$, $\dot{m}^{out}_{mix}$, $W^{out}_{mix}$ and $X^{out}_i$ with i=1 ... N. The input to the model is the inlet mass flow rate $\dot{m}^{in}_{mix}$ as well as the experimentally measured (using the GC) $X^{in}_{CH4}$, $X^{in}_{O2}$, $X^{in}_{N2}$, and $X^{out,GC}_i$ with i=1 ... N−2 ($H_2O$ and Ar are not measured by the GC).

While solving equations (22)-(29), the following assumptions have been made:

The $CH_4$ side inlet mixture consists of $O_2$, $N_2$, $CH_4$ and Ar. Hence: $X^{in}_{O2}+X^{in}_{N2}+X^{in}_{CH4}+X^{in}_{Ar}=1$ and $W^{in}_{mix}=X^{in}_{O2}W_{O2}+X^{in}_{N2}W_{N2}+X^{in}_{CH4}W_{CH4}+X^{in}_{Ar}W_{Ar}$.

The leak from air includes $O_2$ and $N_2$ only with $X^{leak}_{N2}/X^{leak}_{O2}=79/21$.

Only air leaks into the $CH_4$ side of the reactor: $X^{leak}_{N2}+X^{leak}_{O2}=1$, $W^{leak}_{mix}=X^{leak}_{N2}W_{N2}+X^{leak}_{O2}W_{O2}$.

Oxygen ions enter the $CH_4$ side of the reactor through the membrane: $X^{mem}_O=1$, $W^{mem}_{mix}=W_O$.

The active area of the membrane is $A_{active}=\pi d^2/4$, where d=12.5 mm. Note that the diameter of the BFZ91 pellets is 16 mm but it reduces to 12.5 mm due to sealing with the gold rings.

Assuming that the oxygen flux is uniformly distributed along the membrane, the magnitude of $J_{O2}$ is calculated using the following equation (29):

$$|J_{O_2}|(\mu mol/cm^2/s)\frac{|J_O|}{2} = \frac{\dot{m}_{mem} \times 10^5}{2 \times W_O \times A_{mem}} = \frac{\dot{m}_{mem} \times 10^5}{W_{O_2} \times A_{mem}} \tag{29}$$

The $CH_4$ conversion ($C_{CH4}$), $O_2$ conversion ($C_{O2}$), species selectivity ($S_i$), yield ($Y_i$) and activity ($\tilde{n}_i$) are defined as follows (see, for example, Karakaya, C.; Zhu, H.; Zohour, B.; Senkan, S.; Kee, R. J. Detailed Reaction Mechanisms for the Oxidative Coupling of Methane over $La_2O_3/CeO_2$ Nano-fiber Fabric Catalysts. ChemCatChem 9 (2017) 4538-4551, which is incorporated by reference in its entirety):

$$C_{CH_4}(\%) = 100 \times \frac{\dot{n}^{in}_{CH_4} - \dot{n}^{out}_{CH_4}}{\dot{n}^{in}_{CH_4}} \tag{30}$$

$$C_{O_2}(\%) = 100 \times \frac{\dot{n}^{mem}_{O_2} - \dot{n}^{out}_{O_2}}{\dot{n}^{mem}_{O_2}} \tag{31}$$

$$S_i(\%) = 100 \times \frac{\eta_{c-h,i}\dot{n}^{out}_i}{\dot{n}^{in}_{CH_4} - \dot{n}^{out}_{CH_4}} \tag{32}$$

$$Y_i(\%) = 100 \times \frac{\eta_{c-h,i}\dot{n}^{out}_i}{\dot{n}^{in}_{CH_4}} = \frac{C_{CH_4}(\%) \times S_i(\%)}{100} \tag{33}$$

$$\tilde{n}_i(\mu mol/s/g_{cat}) = \frac{\dot{n}_i(\mu mol/s)}{m_{La_2O_3}(g)} \tag{34}$$

In equations (30)-(34), $\eta_{c-h,i}$, is the number of carbon (for CO, $CO_2$, $C_2H_6$ and $C_2H_4$) or hydrogen (for $H_2$ and $H_2O$) atoms in species i relative to $CH_4$, nI is the mole flow rate of species i and $\tilde{n}_i$ is the activity of species i. In this work, $m_{La2O3}$=0.1 (g). The surface area of the $La_2O_3$ catalyst reported herein allows scaling the molar production rate $\tilde{n}_i$ with respect to the catalyst surface area.

The activity of species i, $\tilde{n}_i$, as defined by equation (34) is not a kinetic rate and may be an underestimation of the true activity of the catalyst. For example, if the same yields can be obtained using half the amount of catalyst, the calculated activity based on equation (34) will be doubled. Equation (34) is used here similar to other OCM studies to allow the normalization of the data and their comparison with other studies in the literature.

For the uncertainty and the corresponding error bars, the standard deviation of the experimental measurements is used. To get the uncertainty for all the calculated values from equations (22)-(34), another set of equations has been solved in accordance to equations (22)-(34) using the basic rules of error propagation. The system of equations to get the uncertainties is omitted for the sake of brevity. All the experimental measurements presented in this study include error bars.

Measurements at the $CH_4$ Side of the BFZ91 Membrane Using the Alumina Micro-probe: $H_2O$ Estimation and Species Mole Fraction Correction Similar to the previous section, when measuring the gas-phase composition in the vicinity of the $CH_4$ side of the membrane using the alumina micro-probe, the species measured by the GC are based on a dry basis. To estimate the mole fraction of $H_2O$ near the membrane ($X^{mem}_{H2O}$), a carbon to hydrogen balance between the inlet and the micro-probe measuring location is considered as follows:

$$\frac{x^{in}_{CH_4}}{4x^{in}_{CH_4}} = \frac{1}{4} = \frac{(x^{mem}_{CH_4} + x^{mem}_{CO} + x^{mem}_{CO_2}) + 2(x^{mem}_{C_2H_6} + x^{mem}_{C_2H_4} + x^{mem}_{C_2H_4}) + 3(x^{mem}_{C_3H_8} + x^{mem}_{C_3H_6} + x^{mem}_{C_3H_4iene} x^{mem}_{C_3H_4yne})}{8(x^{mem}_{C_3H_8}) + 6(x^{mem}_{C_2H_6} + x^{mem}_{C_3H_6}) + 4(x^{mem}_{CH_4} + x^{mem}_{C_2H_4} + x^{mem}_{C_3H_4iene} + x^{mem}_{C_3H_4yne}) + 2(x^{mem}_{H_2} + x^{mem}_{H_2O} + x^{mem}_{C_2H_2})} \quad (35)$$

Note that in equation (35), $X^{mem}_i$, is the real mole fraction of species i near the membrane, that is, the mole fraction on a wet basis. Since equation (28) also holds for real and measured mole fractions near the membrane, substitution of equation (28) into equation (35) results in an algebraic equation from which $X^{mem}_{H2O}$ can be calculated directly given that $X^{mem,GC}_{H2O}$, with i=1 ... N-2 (i.e. excluding $H_2O$ and Ar) are known (measured by the GC). Once $X^{mem}_{H2O}$ is known, the mole fraction of species i on a wet basis near the membrane, $X^{mem}_i$ with i=1 ... N, can be calculated using equation (28).

For the uncertainty and the corresponding error bars, the standard deviation of the experimental measurements is used. The system of equations to get the uncertainties is omitted for the sake of brevity.

XRd Patterns of the BFZ91 Powder Before and After Calcination

FIGS. 21A-21B show the XRD patterns of: (FIG. 21A) the uncalcined (i.e. raw ash) BFZ91 powder, and (FIG. 21B) the calcined BFZ91 powder. Several peaks exist in the pattern of the uncalcined BFZ91 powder corresponding to intermediate phases. Calcination at 950° C. for 4h leads to the formation of a phase pure BFZ91 powder without any secondary phases. BFZ91 exhibits a cubic crystal structure.

$CH_4$ Conversion Using a BFZ91 Membrane in the Absence of $La_2O_3$

FIGS. 22A-22P show the $CH_4$ side mole fractions of species near the membrane surface and at the outlet as a function of T and inlet $CH_4$ mole fraction ($X^{in}_{CH4}$) for the case of a 0.67 mm thick BFZ91 membrane without any $La_2O_3$ catalyst on the $CH_4$ side. In addition, FIGS. 23A-23L show the selectivities and yields of all species of interest. The experiment was conducted at T=800-900° C. with ambient air in the air side (200 sccm) and $CH_4$—Ar mixtures in the $CH_4$ side (100 sccm total).

FIGS. 22A-22P and 23A-23L confirm the low catalytic activity of BFZ91 towards: 1) the $CH_4$ decomposition to carbon and $H_2$, 2) the $CH_4$ partial oxidation to syngas or full oxidation to $CO_2$ and $H_2O$, and 3) the $CH_4$ coupling to $C_2H_6$ and $C_2H_4$. The first two are advantageous given that the membrane does not interact with $CH_4$ by promoting side reactions that could reduce the $C_2$ selectivity and yield. It also confirms that the BFZ91 membrane only acts as a means to transport $O_2$ from the air to the $CH_4$ side. The third shows that a catalyst is required to increase the $C_2$ yields.

For completeness, FIG. 24 shows the XRD patterns of the as-prepared and used BFZ91 pellet. For the latter, XRD was conducted at the air and $CH_4$ side. FIG. 24 confirms that the BFZ91 membrane is structurally stable in the presence of hydrocarbons. No secondary phases are detected in the XRD patterns.

Sintering of the $La_2O_3$ Catalyst Due to the Sealing of the Membrane Reactor at T=1025° C.

To confirm that the sintering of the $La_2O_3$ catalyst after the OCM measurements (shown in FIG. 10F) is due to catalyst sintering at T=1025° C. used to seal the membrane reactor and not due to operation in a reactive environment, $La_2O_3$ powder was calcined in ambient air at T=1025° C. for 24 h to mimic the sealing conditions of the membrane reactor. The results are shown in FIGS. 25A-25B. The sintering shown in both images is nearly the same and hence, it was confirmed that the sintering of $La_2O_3$ observed at the end of the OCM measurements is due to the high T operation used to seal the membrane reactor.

Impact of $La_2O_3$ on the $C_2H_6$ and $C_2H_4$ Non-Oxidative Dehydrogenation The experimental setup shown in FIG. 26 was used to investigate the impact of $La_2O_3$ on the non-oxidative dehydrogenation of $C_2H_6$ and $C_2H_4$. The setup consists of a quartz tube with one end closed and of an alumina tube with both ends open (used for the flow introduction) enclosed within a vertical high temperature furnace. Experiments were conducted in the absence of $La_2O_3$ (to characterize the $C_2H_6$ and $C_2H_4$ non-oxidative dehydrogenation in the gas-phase) and in the presence of $La_2O_3$ (to investigate the impact of $La_2O_3$ on the non-oxidative dehydrogenation of $C_2H_6$ and $C_2H_4$). For the latter measurements, 0.3 g of as-purchased $La_2O_3$ powder were positioned at the closed end of the quartz tube, as shown in FIG. 26.

For both experiments, the temperature was increased from T=30° C. to T=750° C. with a ramp rate equal to 5° C./min while flowing 100 sscm of pure Ar. The temperature was maintained at T=750° C. for 5 h at the same flow conditions to ensure that pure $La_2O_3$ had formed prior to $C_2H_6$ introduction. Then, the gas was switched to $X^{in}_{C2H6}=1\%$ (balanced by Ar) with a total volumetric flow rate equal to 100 sccm and after steady-state was achieved, the temperature was increased from T=750° C. to T=900° C. with a ramp rate equal to 1° C./min. During this stage, measurements were taken at the exit of the reactor approximately every 4 minutes and the mixture composition was analyzed using the GC.

The results of the experiments with and without $La_2O_3$ are shown in FIGS. 27A-27F. The figure also includes equilibrium calculations at constant temperature and pressure (1 atm) for the same mixture composition based on the GRI-MECH 3.0 reaction mechanism. Three separate runs were conducted for the case without $La_2O_3$ and two separate runs for the case with $La_2O_3$ and all measurements lead to an almost identical behavior. Hence, FIGS. 27A-27F include the results of one run for each case (with and without $La_2O_3$).

Figure 27A:
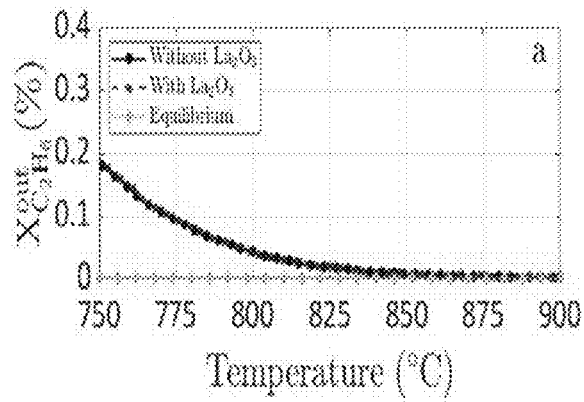
FIGS. 27A-27F depict species mole fractions at the outlet of the reactor (shown in FIG. 26) as a function of T during the non-oxidative dehydrogenation of $C_2H_6$ in the presence and absence of $La_2O_3$.
Figure 27B:
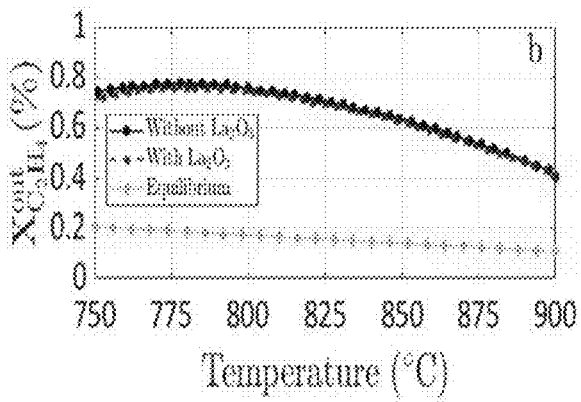
Figure 27C:
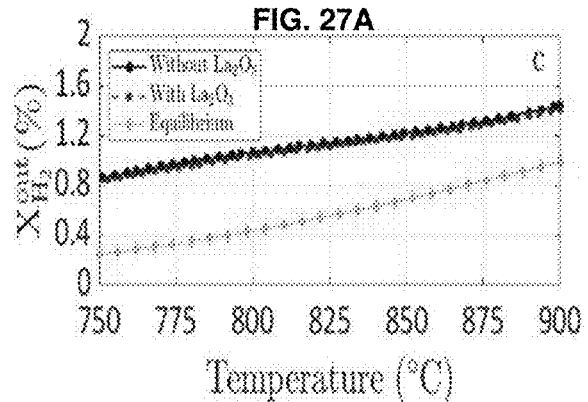
Figure 27D:
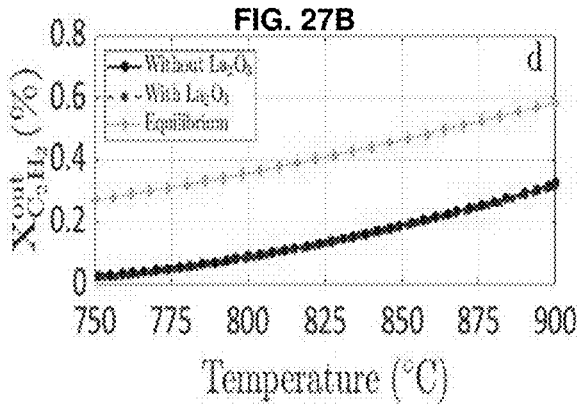
Figure 27E:
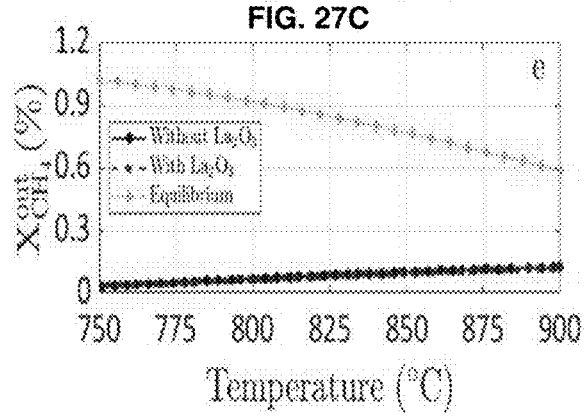
Figure 27F:
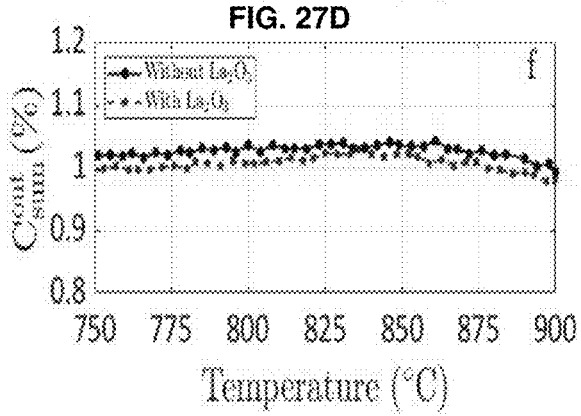

The carbon species summation at the exit of the reactor ($C^{out}_{sum}$) shown in FIG. 27F has been calculated through the following equation:

$$C_{sum}^{out}(\%)=X_{C_2H_6}^{out}+X_{C_2H_4}^{out}+X_{C_2H_2}^{out}+X_{CH_4}^{out} \quad (36)$$

At T≤860° C., $C^{out}_{sum} \approx X^{in}_{C2H6}$ demonstrating the absence of any carbon deposition. The decrease in $C^{out}_{sum}$ observed at T>860° C. is due to carbon deposition. This was further confirmed by visual inspection of the quartz tube after the end of the experiment showing dark brown areas close to the exit of the reactor. However, no signs of carbon deposition were observed near the $La_2O_3$ catalyst.

Figure 29A:
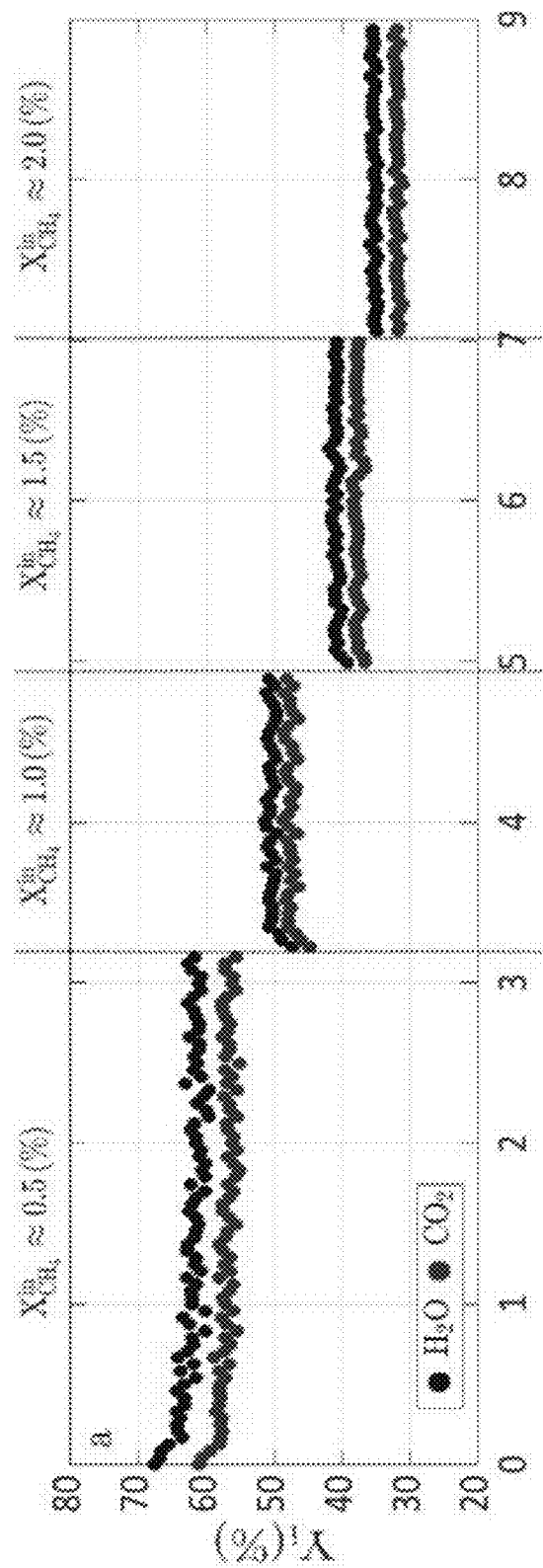
FIGS. 29A-29B depict long-term performance of BFZ91 with $La_2O_3$ at T=850° C. under partial $O_2$ consumption conditions.
Figure 29B:
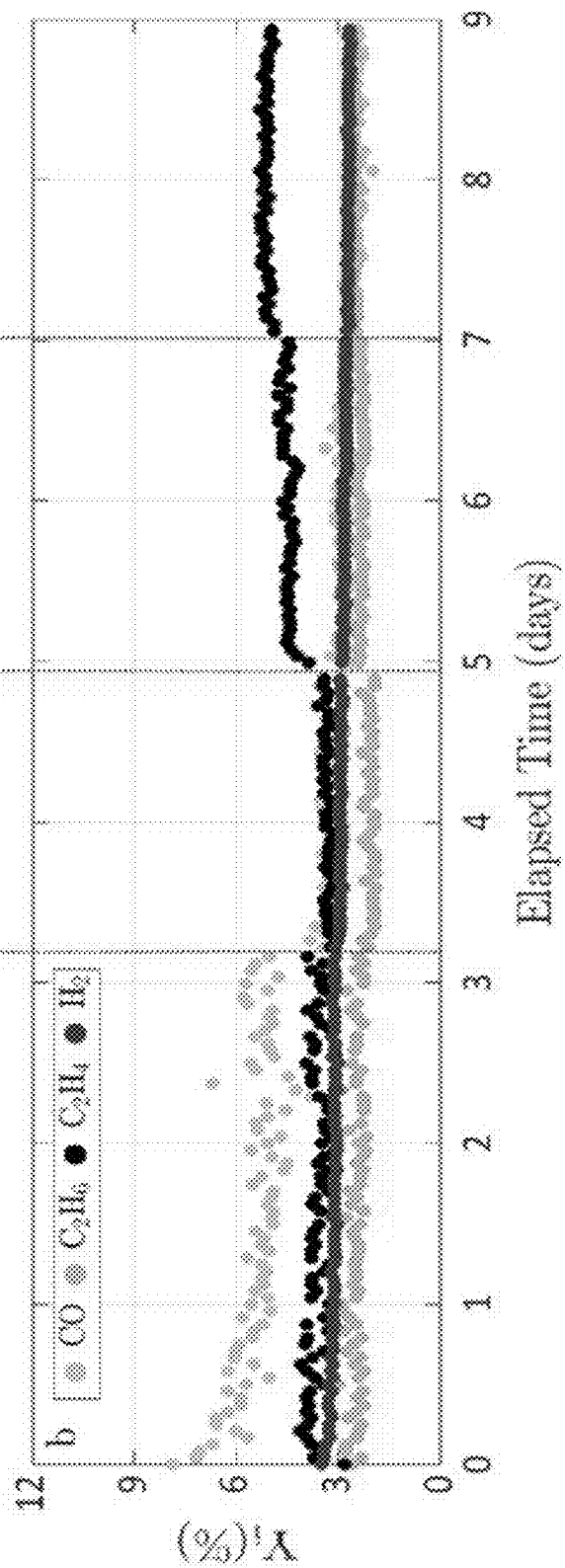

Performance and Stability of BFZ91 and $La_2O_3$ Under Partial $O_2$ Consumption conditions FIGS. 28A-28B show the selectivities of $H_2O$, $CO_2$, $C_2H_4$, $C_2H_6$, $H_2$ and CO as a function of time and $X^{in}_{CH4}$ under conditions of partial $O_2$ consumption (main results are shown in FIGS. 16A-16C). In addition, FIGS. 29A-29B show the corresponding yields. Finally, FIGS. 30A-30C show the mole fractions of the relevant species at the outlet of the $CH_4$ side. Overall, no loss of performance is observed under these conditions.

Performance and stability of BFZ91 and $La_2O_3$ under an undiluted $CH_4$ stream FIGS. 31A-31B show the selectivities and yields of $H_2O$, $CO_2$, $C_2H_4$, $C_2H_6$, $H_2$ and CO as a function of time (main results are shown in FIGS. 17A-17B). In addition, FIGS. 32A-32B show the XRD spectra of the BFZ91 membrane and $La_2O_3$ catalyst at the end of the OCM test. Note that the same membrane and catalyst have been used for the stability test under partial $O_2$ consumption (initial test) and pure $CH_4$ (final test).

Figure 33C:
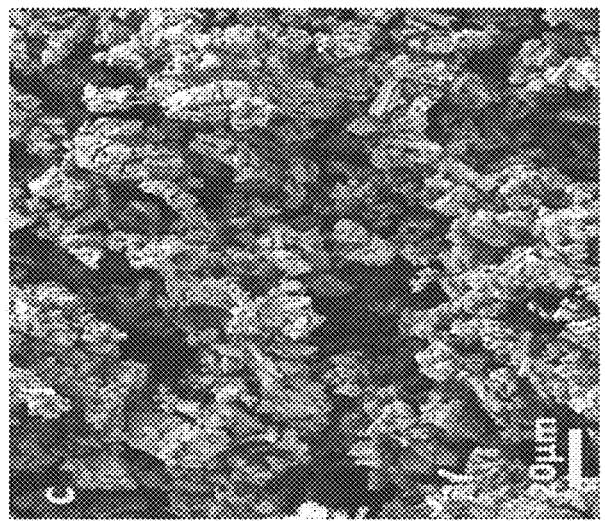
Figure 33B:
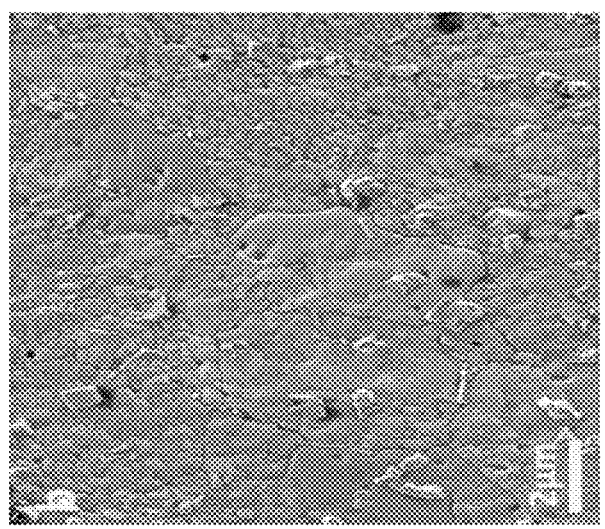
Figure 33A:
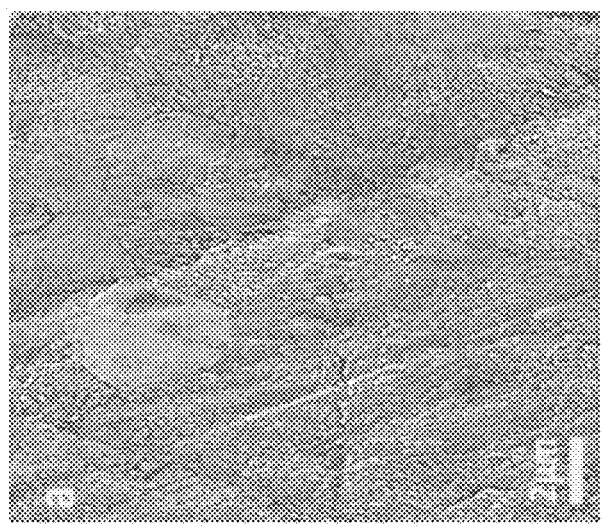
Figure 34:
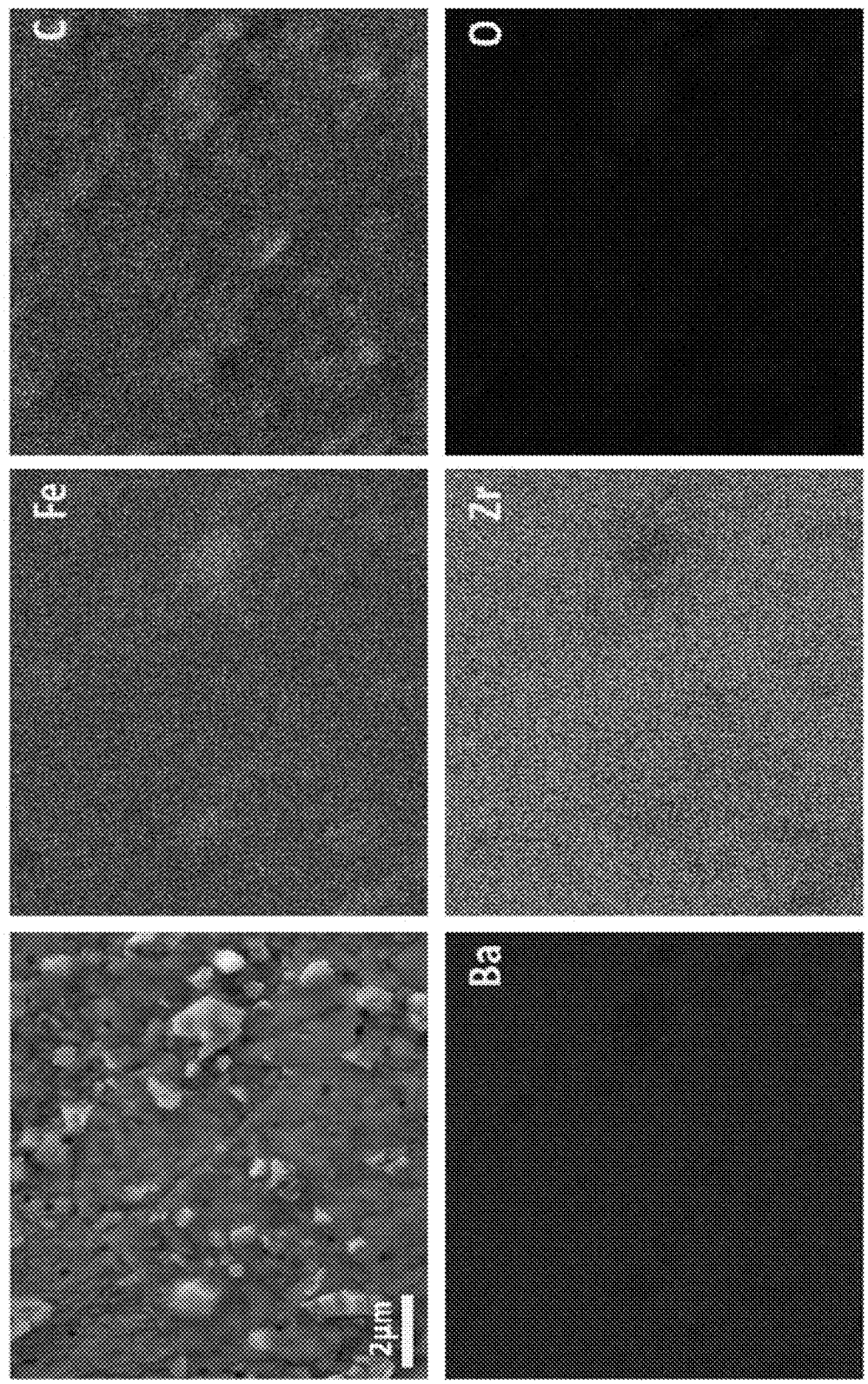
FIG. 34 depicts an SEM image and EDS mapping on the $CH_4$ side of the used BFZ91 membrane after the end of the long-term measurements reported in FIGS. 16A-16C (partial $O_2$ consumption case) and FIGS. 17A-17B (undiluted $CH_4$ case).

FIGS. 33A-33C show SEM images of the used BFZ91 membrane and $La_2O_3$ catalyst after the end of the long-term measurements reported in FIGS. 16A-16C (partial $O_2$ consumption case) and FIGS. 17A-17B (undiluted $CH_4$ case). In addition, FIG. 34 shows another SEM image at the $CH_4$ side of the BFZ91 membrane including results from EDS mapping used to identify the elemental composition of the particles that exist on the corresponding BFZ91 surface.

The following references, cited above, are each incorporated by reference in their entirety.

(1) Garside, M. Production Capacity of Ethylene Worldwide in 2018 and 2030; Statista, 2020, November, 2019.

(2) Garside, M. Production of Selected Chemicals and Plastics in the United States in 2019, by Type; Statista, August, 2020.

(3) Gao, Y.; Neal, L.; Ding, D.; Wu, W.; Baroi, C.; Gaffney, A. M.; Li, F. Recent Advances in Intensified Ethylene Production-A Review. ACS Catal. 2019, 9, 8592-8621.

(4) Global Ethylene Industry Outlook to 2023-Capacity and Capital Expenditure Forecasts with Details of All Active and Planned Plants; GlobalData, April, 2019.

(5) Sims, M. US October Ethylene Contracts Settle up 0.75 Cent/lb; ICIS, October, 2019.

(6) Gärtner, C. A.; van Veen, A. C.; Lercher, J. A. Oxidative Dehydrogenation of Ethane: Common Principles and Mechanistic Aspects. ChemCatChem 2013, 5, 3196-3217.

(7) Nowlin, T. E. Business and Technology of the Global Polyethylene Industry; John Willey & Sons and Scrivener Publishing, 2014.

(8) The Future of Petrochemicals: Growth Surrounded by Uncertainty; Deloitte, 2019.

(9) Worrell, E.; Price, L.; Neelis, M.; Galitsky, C.; Nan, Z. World Best Practice Energy Intensity Values for Selected Industrial Sectors; Lawrence Berkeley National Laboratory, 62806, 2007.

(10) Sholl, D. S.; Lively, R. P. Seven Chemical Separations to Change the World. Nature 2016, 532, 435-437.

(11) Keller, G.; Bhasin, M. M. Synthesis of Ethylene via Oxidative Coupling of Methane I. Determination of Active Catalysts. J. Catal. 1982, 73, 9-19.

(12) Karakaya, C.; Kee, R. J. Progress in the Direct Catalytic Conversion of Methane to Fuels and Chemicals. Prog. Energy Combust. Sci. 2016, 55, 60-97.

(13) Farrell, B. L.; Igenegbai, V. O.; Linic, S. A Viewpoint on Direct Methane Conversion to Ethane and Ethylene Using Oxidative Coupling on Solid Catalysts. ACS Catal. 2016, 6, 4340-4346.

(14) Ghoniem, A. F.; Zhao, Z.; Dimitrakopoulos, G. Gas Oxy Combustion and Conversion Technologies for Low Carbon Energy: Fundamentals, Modeling and Reactors. Proc. Combust. Inst. 2019, 37, 33-56.

(15) Schmack, R.; Friedrich, A.; Kondratenko, E. V.; Polte, J.; Werwatz, A.; Kraehnert, R. A Meta-Analysis of Catalytic Literature Data Reveals Property-Performance Correlations for the OCM Reaction. Nat. Commun. 2019, 10, 441.

(16) Gemini-Natural Gas to Ethylene; Siluria Technologies. http://siluria.com/Products/Gemini_-_Natural_Gas_to_Ethylene.

(17) Reyes, S. C.; Iglesia, E.; Kelkar, C. P. Kinetic-Transport Models of Bimodal Reaction Sequences-I. Homogeneous and Heterogeneous Pathways in Oxidative Coupling of Methane. Chem. Eng. Sci. 1993, 48, 2643-2661.

(18) Lunsford, J. H. Catalytic Conversion of Methane to More Useful Chemicals and Fuels: a Challenge for the 21st Century. Catal. Today 2000, 63, 165-174.

(19) Spallina, V.; Velarde, I. C.; Jimenez, J. A. M.; Godini, H. R.; Gallucci, F.; van Sint Annaland, M. Techno-Economic Assessment of Different Routes for Olefins Production Through the Oxidative Coupling of Methane (OCM): Advances in Benchmark Technologies. Energy Conyers. Manage. 2017, 154, 244-261.
(20) Powell, J. B. Natural Gas Utilization: Current Status and Opportunities. Catal. Today 2020, 356, 27-36.
(21) Cruellas, A.; Bakker, J. J.; van Sint Annaland, M.; Medrano, J. A.; Gallucci, F. Techno-Economic Analysis of Oxidative Coupling of Methane: Current State of the Art and Future Perspectives. Energy Conyers. Manage. 2019, 198, 111789.
(22) Cruellas, A.; Heezius, J.; Spallina, V.; van Sint Annaland, M.; Medrano, J. A.; Gallucci, F. Oxidative Coupling of Methane in Membrane Reactors; A Techno-Economic Assessment. Processes 2020, 8, 274.
(23) Lu, Y.; Dixon, A. G.; Moser, W. R.; Ma, Y. H.; Balachandran, U. Oxygen-Permeable Dense Membrane Reactor for the Oxidative Coupling of Methane. J. Membr. Sci. 2000, 170, 27-34.
(24) Othman, N. H.; Wu, Z.; Li, K. A Micro-Structured $La_{0.6}Sr_{0.4}Co_{0.2}Fe_{0.8}O_{3-\delta}$ Hollow Fibre Membrane Reactor for Oxidative Coupling of Methane. J. Membr. Sci. 2014, 468, 31-41.
(25) Akin, F. T.; Lin, Y. S. Oxidative Coupling of Methane in Dense Ceramic Membrane Reactor with High Yields. AIChE J. 2002, 48, 2298-2306.
(26) Karakaya, C.; Zhu, H.; Zohour, B.; Senkan, S.; Kee, R. J. Detailed Reaction Mechanisms for the Oxidative Coupling of Methane over $La_2O_3/CeO_2$ Nanofiber Fabric Catalysts. ChemCatChem 2017, 9, 4538-4551.
(27) Wu, X.-Y.; Ghoniem, A. F. Mixed Ionic-Electronic Conducting (MIEC) Membranes for Thermochemical Reduction of CO2: A Review. Prog. Energy Combust. Sci. 2019, 74, 1-30.
(28) Dimitrakopoulos, G.; Ghoniem, A. F. A Two-Step Surface Exchange Mechanism and Detailed Defect Transport to Model Oxygen Permeation Through the $La_{0.9}Ca_{0.1}FeO_{3-\delta}$ Mixed-Conductor. J. Membr. Sci. 2016, 510, 209-219.
(29) Dimitrakopoulos, G.; Ghoniem, A. F. Developing a Multistep Surface Reaction Mechanism to Model the Impact of $H_2$ and CO on the Performance and Defect Chemistry of $La_{0.9}Ca_{0.1}FeO_{3-\delta}$ Mixed-Conductors. J. Membr. Sci. 2017, 529, 114-132.
(30) Hunt, A.; Dimitrakopoulos, G.; Kirchen, P.; Ghoniem, A. F. Measuring the Oxygen Profile and Permeation Flux Across an Ion Transport $La_{0.9}Ca_{0.1}FeO_{3-\delta}$ Membrane and the Development and Validation of a Multistep Surface Exchange Model. J. Membr. Sci. 2015, 468, 62-72.
(31) Hunt, A.; Dimitrakopoulos, G.; Ghoniem, A. F. Surface Oxygen Vacancy and Oxygen Permeation Flux Limits of Perovskite Ion Transport Membranes. J. Membr. Sci. 2015, 489, 248-257.
(32) Lee, W.; Han, J. W.; Chen, Y.; Cal, Z.; Yildiz, B. Cation Size Mismatch and Charge Interactions Drive Dopant Segregation at the Surfaces of Manganite Perovskites. J. Am. Chem. Soc. 2013, 135, 7909-7925.
(33) Igenegbai, V. O.; Meyer, R. J.; Linic, S. In Search of Membrane-Catalyst Materials for Oxidative Coupling of Methane: Performance and Phase Stability Studies of Gadolinium-Doped Barium Cerate and the Impact of Zr Doping. Appl. Catal., B 2018, 230, 29-35.
(34) Deibert, W.; Ivanova, M. E.; Baumann, S.; Guillon, O.; Meulenberg, W. A. Ion-Conducting Ceramic Membrane Reactors for High-Temperature Applications. J. Membr. Sci. 2017, 543, 79-97.
(35) Sunarso, J.; Hashim, S. S.; Zhu, N.; Zhou, W. Perovskite Oxides Applications in High Temperature Oxygen Separation, Solid Oxide Fuel Cell and Membrane Reactor: A Review. Prog. Energy Combust. Sci. 2017, 61, 57-77.
(36) Igenegbai, V. O.; Almallahi, R.; Meyer, R. J.; Linic, S. Oxidative Coupling of Methane over Hybrid Membrane/Catalyst Active Centers: Chemical Requirements for Prolonged Lifetime. ACS Energy Lett. 2019, 4, 1465-1470.
(37) Garcia-Fayos, J.; Lobera, M. P.; Balaguer, M.; Serra, J. M. Catalyst Screening for Oxidative Coupling of Methane Integrated in Membrane Reactors. Front. Mater. 2018, 5, 31.
(38) Othman, N. H.; Wu, Z.; Li, K. An Oxygen Permeable Membrane Microreactor With an In-Situ Deposited $Bi_{1.5}Y_{0.3}Sm_{0.2}O_{3-\delta}$ Catalyst for Oxidative Coupling of Methane. J. Membr. Sci. 2015, 488, 182-193.
(39) Tan, X.; Pang, Z.; Gu, Z.; Liu, S. Catalytic Perovskite Hollow Fibre Membrane Reactors for Methane Oxidative Coupling. J. Membr. Sci. 2007, 302, 109-114.
(40) Zheng, Y.; Lin, Y. S. Oxidative Coupling of Methane on Improved Bismuth Oxide Membrane Reactors. AIChE J. 2001, 47, 436-444.
(41) Cao, Z.; Jiang, H.; Luo, H.; Baumann, S.; Meulenberg, W. A.; Voss, H.; Caro, J. Simultaneous Overcome of the Equilibrium Limitations in BSCF Oxygen-Permeable Membrane Reactors: Water Splitting and Methane Coupling. Catal. Today 2012, 193, 2-7.
(42) Bucher, E.; Egger, A.; Caraman, G. B.; Sitte, W. Stability of the SOFC Cathode Material $Ba_{0.5}Sr_{0.5}Co_{0.8}Fe_{0.2}O_{3-\delta}$ in $CO_2$-Containing Atmospheres. J. Electrochem. Soc. 2008, 155, B1218-B1224.
(43) Almar, L.; Störmer, H.; Meffert, M.; Szász, J.; Wankmüller, F.; Gerthsen, D.; Ivers-Tiffée, E. Improved Phase Stability and $CO_2$ Poisoning Robustness of Y-Doped $Ba_{0.5}Sr_{0.5}Co_{0.8}Fe_{0.2}O_{3-\delta}$ SOFC Cathodes at Intermediate Temperatures. ACS Appl. Energy Mater. 2018, 1, 1316-1327.
(44) Zhang, R.; Taskinen, P. Experimental Investigation of Liquidus and Phase Stability in the $BaO-SiO_2$ Binary System. J. Alloys Compd. 2016, 657, 770-776.
(45) Chi, Y.; Li, T.; Wang, B.; Wu, Z.; Li, K. Morphology, Performance and Stability of Multi-Bore Capillary $La_{0.6}Sr_{0.4}Co_{0.2}Fe_{0.8}O_{3-\delta}$ Oxygen Transport Membranes. J. Membr. Sci. 2017, 529, 224-233.
(46) Hardy, J. S.; Coyle, C. A.; Bonnett, J. F.; Templeton, J. W.; Canfield, N. L.; Edwards, D. J.; Mahserejian, S. M.; Ge, L.; Ingram, B. J.; Stevenson, J. W. Evaluation of Cation Migration in Lanthanum Strontium Cobalt Ferrite Solid Oxide Fuel Cell Cathodes via In-Operando X-Ray Diffraction. J. Mater. Chem. A 2018, 6, 1787-1801.
(47) Viitanen, M.; v. Welzenis, R. G.; Brongersma, H. H.; van Berkel, F. P. F. Silica Poisoning of Oxygen Membranes. Solid State Ionics 2002, 150, 223-228.
(48) Perz, M.; Bucher, E.; Gspan, C.; Waldhäusl, J.; Hofer, F.; Sitte, W. Long-Term Degradation of $La_{0.6}Sr_{0.4}Co_{0.2}Fe_{0.8}O_{3-\delta}$ IT-SOFC Cathodes due to Silicon Poisoning. Solid State Ionics 2016, 288, 22-27.
(49) Chen, K.; Jiang, S. P. Surface Segregation in Solid Oxide Cell Oxygen Electrodes: Phenomena, Mitigation Strategies and Electrochemical Properties. Electrochem. Energy Rev. 2020, 3, 730-765.
(50) Palermo, A.; Holgadovazquez, J.; Lee, A.; Tikhov, M.; Lambert, R. Critical Influence of the Amorphous Silica-to-Cristobalite Phase Transition on the Perfor-

(50) mance of Mn/Na$_2$WO$_4$/SiO$_2$ Catalysts for the Oxidative Coupling of Methane. J. Catal. 1998, 177, 259-266.

(51) Arndt, S.; Otremba, T.; Simon, U.; Yildiz, M.; Schubert, H.; Schomäcker, R. Mn—Na$_2$WO$_4$/SiO$_2$ as Catalyst for the Oxidative Coupling of Methane. What is Really Known? Appl. Catal., A 2012, 425-426, 53-61.

(52) Rojac, T.; Bencan, A.; Drazic, G.; Kosec, M.; Damjanovic, D. Piezoelectric Nonlinearity and Frequency Dispersion of the Direct Piezoelectric Response of BiFeO3 Ceramics. J. Appl. Phys. 2012, 112, 064114.

(53) Lv, J.; Wu, J.; Wu, W. Enhanced Electrical Properties of Quenched (1-x)Bi$_{1-y}$Sm$_y$FeO$_3$-xBiScO$_3$ Lead-Free Ceramics. J. Phys. Chem. C 2015, 119, 21105-21115.

(54) Lin, Y. S.; Zeng, Y. Catalytic Properties of Oxygen Semi-permeable Perovskite-Type Ceramic Membrane Materials for Oxidative Coupling of Methane. J. Catal. 1996, 164, 220-231.

(55) Arndt, S.; Simon, U.; Heitz, S.; Berthold, A.; Beck, B.; Görke, O.; Epping, J.-D.; Otremba, T.; Aksu, Y.; Irran, E.; Laugel, G.; Driess, M.; Schubert, H.; Schomäcker, R. Li-Doped MgO From Different Preparative Routes for the Oxidative Coupling of Methane. Top. Catal. 2011, 54, 1266-1285.

(56) Luo, L.; Tang, X.; Wang, W.; Wang, Y.; Sun, S.; Qi, F.; Huang, W. Methyl Radicals in Oxidative Coupling of Methane Directly Confirmed by Synchrotron VUV Photoionization Mass Spectroscopy. Sci. Rep. 2013, 3, 1625.

(57) Schucker, R. C.; Dimitrakopoulos, G.; Derrickson, K.; Kopeć, K. K.; Alahmadi, F.; Johnson, J. R.; Shao, L.; Ghoniem, A. F. Oxidative Dehydrogenation of Ethane to Ethylene in an Oxygen-Ion-Transport-Membrane Reactor: A Proposed Design for Process Intensification. Ind. Eng. Chem. Res. 2019, 58, 7989-7997.

(58) Dimitrakopoulos, G.; Schucker, R. C.; Derrickson, K.; Johnson, J. R.; Kopeć, K. K.; Shao, L.; Alahmadi, F.; Ghoniem, A. F. Hydrogen and Ethylene Production Through Water-Splitting and Ethane Dehydrogenation Using BaFe$_{0.9}$Zr$_{0.1}$O$_{3-\delta}$ Mixed-Conductors. ECS Trans. 2017, 80, 181-190.

(59) Yildiz, M.; Simon, U.; Otremba, T.; Aksu, Y.; Kailasam, K.; Thomas, A.; Schomäcker, R.; Arndt, S. Support Material Variation for the Mn$_x$O$_y$—Na$_2$WO$_4$/SiO$_2$ Catalyst. Catal. Today 2014, 228, 5-14.

(60) Song, J.; Sun, Y.; Ba, R.; Huang, S.; Zhao, Y.; Zhang, J.; Sun, Y.; Zhu, Y. Monodisperse Sr—La$_2$O$_3$ Hybrid Nanofibers for Oxidative Coupling of Methane to Synthesize C$_2$ Hydrocarbons. Nanoscale 2015, 7, 2260-2264.

(61) Huang, P.; Zhao, Y.; Zhang, J.; Zhu, Y.; Sun, Y. Exploiting Shape Effects of La$_2$O$_3$ Nanocatalysts for Oxidative Coupling of Methane Reaction. Nanoscale 2013, 5, 10844-10848.

(62) Schucker, R. C.; J. Derrickson, K.; K. Ali, A.; J. Caton, N. The Effect of Strontium Content on the Activity and Selectivity of Sr-Doped La$_2$O$_3$ Catalysts in Oxidative Coupling of Methane. Appl. Catal., A 2020, 607, 117827.

(63) Babilo, P.; Haile, S. M. Enhanced Sintering of Yttrium-Doped Barium Zirconate by Addition of ZnO. J. Am. Ceram. Soc. 2005, 88, 2362-2368.

(64) Dimitrakopoulos, G.; Ghoniem, A. F.; Yildiz, B. In Situ Catalyst Exsolution on Perovskite Oxides for the Production of CO and Synthesis Gas in Ceramic Membrane Reactors. Sustainable Energy Fuels 2019, 3, 2347-2355.

(65) Watanabe, K.; Takauchi, D.; Yuasa, M.; Kida, T.; Shimanoe, K.; Teraoka, Y.; Yamazoe, N. Oxygen Permeation Properties of Co-Free Perovskite-Type Oxide Membranes Based on BaFe$_{1-y}$Zr$_y$O$_{3-\delta}$. J. Electrochem. Soc. 2009, 156, E81-E85.

(66) Kida, T.; Takauchi, D.; Watanabe, K.; Yuasa, M.; Shimanoe, K.; Teraoka, Y.; Yamazoe, N. Oxygen Permeation Properties of Partially A-Site Substituted BaFeO$_{3-\delta}$ Perovskites. J. Electrochem. Soc. 2009, 156, E187-E191.

(67) Park, C. Y.; Lee, T. H.; Dorris, S. E.; Balachandran, U. A Cobalt-Free Oxygen Transport Membrane, BaFe$_{0.9}$Zr$_{0.1}$O$_{3-\delta}$, and its Application for Producing Hydrogen. Int. J. Hydrogen Energy 2013, 38, 6450-6459.

(68) Wang, J.; Saccoccio, M.; Chen, D.; Gao, Y.; Chen, C.; Ciucci, F. The Effect of A-Site and B-Site Substitution on BaFeO$_{3-\delta}$: An Investigation as a Cathode Material for Intermediate-Temperature Solid Oxide Fuel Cells. J. Power Sources 2015, 297, 511-518.

(69) Geary, T. C.; Adler, S. B. Oxygen Nonstoichiometry and Defect Chemistry of the Mixed Conductor La$_{0.9}$Ca$_{0.1}$FeO$_{3-\delta}$ at Low Oxygen Partial Pressure. Solid State Ionics 2013, 253, 88-93.

(70) Kuhn, M.; Hashimoto, S.; Sato, K.; Yashiro, K.; Mizusaki, J. Oxygen Nonstoichiometry, Thermo-Chemical Stability and Lattice Expansion of La$_{0.6}$Sr$_{0.4}$FeO$_{3-\delta}$. Solid State Ionics 2011, 195, 7-15.

(71) Fleming, P.; Farrell, R. A.; Holmes, J. D.; Morris, M. A. The Rapid Formation of La(OH)$_3$ from La$_2$O$_3$ Powders on Exposure to Water Vapor. J. Am. Ceram. Soc. 2010, 93, 1187-1194.

(72) Neumann, A.; Walter, D. The Thermal Transformation From Lanthanum Hydroxide to Lanthanum Hydroxide Oxide. Thermochim. Acta 2006, 445, 200-204.

(73) Zhu, J.; Gui, Z.; Ding, Y. A Simple Route to Lanthanum Hydroxide Nanorods. Mater. Lett. 2008, 62, 2373-2376.

(74) Ozawa, M.; Onoe, R.; Kato, H. Formation and Decomposition of Some Rare Earth (RE=La, Ce, Pr) Hydroxides and Oxides by Homogeneous Precipitation. J. Alloys Compd. 2006, 408-412, 556-559.

(75) Kim, S. J.; Han, W. K.; Kang, S. G.; Han, M. S.; Cheong, Y. H. Formation of Lanthanum Hydroxide and Oxide via Precipitation. Solid State Phenom. 2008, 135, 23-26.

(76) Jeevanandam, P.; Koltypin, Y.; Palchik, O.; Gedanken, A. Synthesis of Morphologically Controlled Lanthanum Carbonate Particles Using Ultrasound Irradiation. J. Mater. Chem. 2001, 11, 869-873.

(77) Shirsat, A. N.; Ali, M.; Kaimal, K. N. G.; Bharadwaj, S. R.; Das, D. Thermochemistry of La$_2$O$_2$CO$_3$ Decomposition. Thermochim. Acta 2003, 399, 167-170.

(78) Hou, Y.-H.; Han, W.-C.; Xia, W.-S.; Wan, H.-L. Structure Sensitivity of La$_2$O$_2$CO$_3$ Catalysts in the Oxidative Coupling of Methane. ACS Catal. 2015, 5, 1663-1674.

(79) Chase, M. W. NIST-JANAF Thermochemical Tables, 4th ed; Part I, Al-Co, Journal of Physical and Chemical Reference Data, Monograph No. 9; American Institute of Physics and the American Chemical Society, 1998.

(80) Morss, L. R.; Edelstein, N. M.; Fuger, J. The Chemistry of the Actinide and Transactinide Elements, 4th ed; Springer; Volume 1-6, 2010.

(81) Konings, R. J. M.; Beneš, O.; Kovacs, A.; Manara, D.; Sedmidubský, D.; Gorokhov, L.; Iorish, V. S.;

Yungman, V.; Shenyayskaya, E.; Osina, E. The Thermodynamic Properties of the f-Elements and their Compounds. Part 2. The Lanthanide and Actinide Oxides. J. Phys. Chem. Ref. Data 2014, 43, 013101.
(82) Liu, Z.; Ho Li, J. P.; Vovk, E.; Zhu, Y.; Li, S.; Wang, S.; van Bavel, A. P.; Yang, Y. Online Kinetics Study of Oxidative Coupling of Methane over $La_2O_3$ for Methane Activation: What Is Behind the Distinguished Light-off Temperatures. ACS Catal. 2018, 8, 11761-11772.
(83) Dimitrakopoulos, G.; Ghoniem, A. F. Role of Gas-Phase and Surface Chemistry in Methane Reforming Using a $La_{0.9}Ca_{0.1}FeO_{3-\delta}$ Oxygen Transport Membrane. Proc. Combust. Inst. 2017, 36, 4347-4354.
(84) Kirchen, P.; Apo, D. J.; Hunt, A.; Ghoniem, A. F. A Novel Ion Transport Membrane Reactor for Fundamental Investigations of Oxygen Permeation and Oxy-Combustion Under Reactive Flow Conditions. Proc. Combust. Inst. 2013, 34, 3463-3470.
(85) Song, J.; Qiu, Z.; Gao, J.; Tan, X.; Sunarso, J.; Wang, S.; Liu, S. $CO_2$ Erosion of $BaCo_{0.85}Bi_{0.05}Zr_{0.1}O_{3-\delta}$ Perovskite Membranes Under Oxygen Permeating Conditions. Sep. Purif. Technol. 2018, 207, 133-141.
(86) Balachandran, U.; Dorris, S. E.; Emerson, J. E.; Lee, T. H.; Lu, Y.; Park, C. Y.; Picciolo, J. J. Hydrogen Production by Water Dissociation Using Ceramic Membranes—Annual Report for FY 2010. ANL-11/07; Argonne National Labs, Feb. 7, 2011.
(87) Prakash, B.; Chakraverty, S. Realization of Atomically Flat Steps and Terraces Like Surface of $SrTiO_3$ (001) Single Crystal by Hot Water Etching and High Temperature Annealing. Solid State Commun. 2015, 213-214, 28-30.
(88) Sánchez, F.; Ocal, C.; Fontcuberta, J. Tailored Surfaces of Perovskite Oxide Substrates for Conducted Growth of Thin Films. Chem. Soc. Rev. 2014, 43, 2272-2285.
(89) Lacombe, S.; Zanthoff, H.; Mirodatos, C. Oxidative Coupling of Methane over Lanthana Catalysts. J. Catal. 1995, 155, 106-116.
(90) Lunsford, J. H. The Catalytic Oxidative Coupling of Methane. Angew. Chem., Int. Ed. Engl. 1995, 34, 970-980.
(91) Stansch, Z.; Mleczko, L.; Baerns, M. Comprehensive Kinetics of Oxidative Coupling of Methane over the $La_2O_3$/CaO Catalyst. Ind. Eng. Chem. Res. 1997, 36, 2568-2579.
(92) Choudhary, V. R.; Uphade, B. S.; Mulla, S. A. R. Coupling of Endothermic Thermal Cracking with Exothermic Oxidative Dehydro¬genation of Ethane to Ethylene Using a Diluted $SrO/La_2O_3$ Catalyst. Angew. Chem., Int. Ed. 1995, 34, 665-666.
(93) Hayek, N. S.; Khlief, G. J.; Horani, F.; Gazit, O. M. Effect of Reaction Conditions on the Oxidative Coupling of Methane over Doped $MnO_x$—$Na_2WO_4/SiO_2$ Catalyst. J. Catal. 2019, 376, 25-31.
(94) Werny, M. J.; Wang, Y.; Girgsdies, F.; Schlögl, R.; Trunschke, A. Fluctuating Storage of the Active Phase in a Mn—$Na_2WO_4/SiO_2$ Catalyst for the Oxidative Coupling of Methane. Angew. Chem., Int. Ed. 2020, 59, 14921-14926.
(95) Wang, S.; Li, S.; Dixon, D. A. Mechanism of Selective and Complete Oxidation in $La_2O_3$-Catalyzed Oxidative Coupling of Methane. Catal. Sci. Technol. 2020, 10, 2602-2614.
(96) Choudhary, V. R.; Rane, V. H. Oxidative Coupling of Methane over $La_2O_3$. Influence of Catalyst Preparation on Surface Properties and Steady and Oscillating Reaction Behaviour. J. Chem. Soc., Faraday Trans. 1994, 90, 3357-3365.
(97) Ito, T.; Wang, J.; Lin, C. H.; Lunsford, J. H. Oxidative Dimerization of Methane over a Lithium-Promoted Magnesium Oxide Catalyst. J. Am. Chem. Soc. 1985, 107, 5062-5068.
(98) Wang, J. X.; Lunsford, J. H. Evidence for the Thermal Generation of Superoxide Ions on Lanthanum Oxide ($La_2O_3$). J. Phys. Chem. 1986, 90, 3890-3891.
(99) Palmer, M. S.; Neurock, M.; Olken, M. M. Periodic Density Functional Theory Study of the Dissociative Adsorption of Molecular Oxygen over $La_2O_3$. J. Phys. Chem. B 2002, 106, 6543-6547.
(100) Xu, J.; Zhang, Y.; Xu, X.; Fang, X.; Xi, R.; Liu, Y.; Zheng, R.; Wang, X. Constructing $La_2B_2O_7$ (B=Ti, Zr, Ce) Compounds with Three Typical Crystalline Phases for the Oxidative Coupling of Methane: The Effect of Phase Structures, Superoxide Anions, and Alkalinity on the Reactivity. ACS Catal. 2019, 9, 4030-4045.

Other embodiments are within the scope of the following claims.

What is claimed is:

1. A method of making a ceramic membrane comprising:
dissolving a barium salt, an iron salt, and a zirconium salt in a solvent to form a precursor solution;
adjusting the pH of the precursor solution to form a mixture;
drying the mixture to form an ash;
calcining the ash to form a perovskite oxide; and
distributing a lanthanum oxide catalyst on a surface of the perovskite oxide to form the ceramic membrane;
wherein the perovskite oxide has the formula $BaBO_{3-\delta}$, wherein B is a mixture of Fe and Zr.

2. The method of claim 1, wherein the precursor solution includes citric acid and a chelating agent.

3. The method of claim 2, wherein the chelating agent is ethylenediaminetetraacetic acid.

4. The method of claim 3, wherein the ash is calcined at 800° C. to 1000° C.

5. The method of claim 1, further comprising sintering the perovskite oxide at 1250° C. or less.

6. The method of claim 1, wherein $\delta$ is 0 to 0.6.

7. The method of claim 6, wherein the perovskite oxide has a unit cell lattice constant of 4.022 Å or greater.

8. The method of claim 6, wherein the perovskite oxide is $BaFe_{0.9}Zr_{0.1}O_{3-\delta}$.

9. The method of claim 6, wherein the perovskite oxide is $BaFe_{0.9}Zr_{0.1}O^{2.56}$.

10. The method of claim 6, wherein the perovskite oxide is made by a wet chemical process.

11. The method of claim 6, wherein the distributed lanthanum oxide catalyst is substantially free of other metals.

12. The method of claim 1, wherein the mixture of Fe and Zr is 2 to 15 mol % Zr.

* * * * *